US012559448B2

(12) United States Patent
Gunnoe et al.

(10) Patent No.: US 12,559,448 B2
(45) Date of Patent: Feb. 24, 2026

(54) METHODS FOR FUNCTIONALIZATION HYDROCARBONS

(71) Applicants: UNIVERSITY OF VIRGINIA PATENT FOUNDATION, Charlottesville, VA (US); THE TRUSTEES OF PRINCETON UNIVERSITY, Princeton, NJ (US); CALIFORNIA INSTITUTE OF TECHNOLOGY, Pasadena, CA (US)

(72) Inventors: Thomas B. Gunnoe, Palmyra, VA (US); John T. Groves, Princeton, NJ (US); William A. Goddard, III, Pasadena, CA (US)

(73) Assignees: University of Virgina Patent Foundation, Charlottesville, VA (US); The Trustees of Princeton University, Princeton, NJ (US); California Institute of Technology, Pasadena, CA (US)

( * ) Notice: Subject to any disclaimer, the term of this patent is extended or adjusted under 35 U.S.C. 154(b) by 1113 days.

(21) Appl. No.: 17/438,091

(22) PCT Filed: Mar. 13, 2020

(86) PCT No.: PCT/US2020/022707

§ 371 (c)(1),
(2) Date: Sep. 10, 2021

(87) PCT Pub. No.: WO2020/186195

PCT Pub. Date: Sep. 17, 2020

(65) Prior Publication Data

US 2022/0185748 A1 Jun. 16, 2022

Related U.S. Application Data

(60) Provisional application No. 62/817,594, filed on Mar. 13, 2019.

(51) Int. Cl.
C07C 67/035 (2006.01)
C07C 17/10 (2006.01)
(Continued)

(52) U.S. Cl.
CPC ............ C07C 67/035 (2013.01); C07C 17/10 (2013.01); C07C 29/095 (2013.01); C07C 201/08 (2013.01)

(58) Field of Classification Search
None
See application file for complete search history.

(56) References Cited

U.S. PATENT DOCUMENTS 1,591,984 A 7/1926 Krause et al.
2,866,830 A 12/1958 Dunn, Jr. et al.
(Continued)

OTHER PUBLICATIONS

Hein ("Bacterially mediated diagenetic origin for chert-hosted manganese deposits in the Franciscan Complex, California Coast Ranges", Geology(15) 1987, p. 722-726) (Year: 1987).*
(Continued)

Primary Examiner — Amy C Bonaparte
(74) Attorney, Agent, or Firm — Thomas | Horstemeyer, LLP

(57) ABSTRACT

In one aspect, the disclosure relates to a method for functionalizing hydrocarbons. In a further aspect, the method involves heating a hydrocarbon with a composition having an acid and an oxidant. In other aspects, the composition can further include an iodine-based compound and/or a compound having formula $A_aX_n$. In any of these aspects, the oxidant can be regenerated in situ or in a separate regeneration step. Also disclosed are functionalized hydrocarbons produced by the disclosed method. This abstract is intended
(Continued)

as a scanning tool for purposes of searching in the particular art and is not intended to be limiting of the present disclosure.

21 Claims, 33 Drawing Sheets

(51) Int. Cl.
*C07C 29/09* (2006.01)
*C07C 201/08* (2006.01)

(56) References Cited

U.S. PATENT DOCUMENTS

| | | | | |
|---|---|---|---|---|
| 3,173,962 | A | 3/1965 | Carroll et al. | |
| 3,267,161 | A | 8/1966 | Ukaji et al. | |
| 4,207,268 | A | 6/1980 | Sze et al. | |
| 5,099,084 | A | 3/1992 | Stauffer | |
| 5,306,855 | A | 4/1994 | Periana et al. | |
| 6,452,058 | B1 | 9/2002 | Schweizer et al. | |
| 2016/0145188 | A1* | 5/2016 | Gunnoe | C10L 1/02 568/885 |
| 2017/0152207 | A1* | 6/2017 | Gunnoe | C07C 29/00 |

OTHER PUBLICATIONS

Huang ("Thermochemical oxidation of methane by manganese oxides in hydrothermal sediments" Communications Earth & Environment, 2023, p. 224) (Year: 2023).*

Hu ("Thermochemical oxidation of methane induced by high-valence metal oxides in a sedimentary basin" Nature Communications, 2018, p. 5131) (Year: 2018).*

Chen ("Manganese oxide catalyzed methane partial oxidation in trifluoroacetic acid: Catalysis and kinetic analysis" Catalysis Today, 140, 2008, p. 157-161) (Year: 2008).*

Pubchem (Density of Trifluoroacetic Acid, downloaded from https://pubchem.ncbi.nlm.nih.gov/compound/Trifluoroacetic-acid#section=Density&fullscreen=true on Nov. 14, 2024) (Year: 2024).*

Guntlin ("Nanocrystalline FeF3 and MF2 (M=Fe, Co, and Mn) from metal trifluoroacetates and their Li(Na)-ion storage properties", J. Mater. Chem. A, 2017, p. 7387, including Supporting Information p. S1-S37) (Year: 2017).*

Jung ("Development of novel Pd and Pt catalysts for efficient conversion of methane to methanol", ACS Spring 2017, abstract) (Year: 2017).*

Walling et al., "Some Solvent and Structural Effects in Free Radical Chlorination," Journal of the American Chemical Society, Mar. 1959, vol. 81, No. 6, pp. 1485-1489.

Wang et al., "Acetic acid synthesis from methane by non-synthesis gas process," Journal of Molecular Catalysis A: Chemistry, 2005, vol. 225, pp. 65-69.

Wang et al., "Model Iron Phosphate Catalysts for the Oxy-Bromination of Methane," Catalysis Letters, Aug. 2014, vol. 144, pp. 1384-1392.

Wang et al., "Natural gas from shale formation—the evolution, evidences and challenges of shale gas revolution in United States," Renewable and Sustainable Energy Reviews, Feb. 2014, vol. 30, pp. 1-28.

Wang et al., "Structural requirements of manganese oxides for methane oxidation: XAS spectroscopy and transition-state studies," Applied Catalysis B: Environmental, 2018, vol. 229, pp. 52-62.

Wang et al., "Structure and phase analysis of one-pot hydrothermally synthesized FePO4-SBA-15 as an extremely stable catalyst for harsh oxy-bromination of methane," Applied Catalysis A: General, 2013, vol. 453, pp. 235-243.

Webb et al., "Catalytic Oxy-Functionalization of Methane and Other Hydrocarbons: Fundamental Advancements and New Strategies," ChemSusChem, 2011, vol. 4, pp. 37-49.

Webster-Gardiner et al., "Arene C—H activation using Rh(I) catalysts supported by bidentate nitrogen chelates," Catalysis Science & Technology, 2015, vol. 5, pp. 96-100.

Webster-Gardiner et al., "Electrophilic Rh1 catalysts for arene H/D exchange in acidic media: Evidence for an electrophilic aromatic substitution mechanism," Journal of Molecular Catalysis A: Chemical, 2017, vol. 426, pp. 381-388.

Wittcoff et al., Industrial Organic Chemicals, 3rd ed., Hoboken, NJ, John Wiley & Sons, 2012, p. 459.

Zakaria et al., "Direct conversion technologies of methane to methanol: an overview," Renewable and Sustainable Energy Reviews, 2016, vol. 65, pp. 250-261.

Zefirov et al., "Oxidatively Assisted Nucleophilic Substitution of Iodine in Alkyl Iodides by Nucleofugic Anions," Journal of Organic Chemistry, 1985, vol. 50, No. 11, pp. 1872-1876.

Zhdankin et al., "Chemistry of Polyvalent Iodine," Chemical Reviews, Nov. 2008, vol. 108, No. 12, pp. 5299-5358.

Zhdankin, Viktor V., "Hypervalent iodine(III) reagents in organic synthesis," Arkivoc, Feb. 2009, vol. 2009, Issue 1, pp. 1-62.

Zhou et al., "Synergistic Gold-Bismuth Catalysis for Non-Mercury Hydrochlorination of Acetylene to Vinyl Chloride Monomer," ACS Catalysis, Sep. 2014, vol. 4, Issue 9, pp. 3112-3116.

Zichitella et al., "Catalytic Oxychlorination versus Oxybromination for Methane Functionalization," ACS Catalysis, Mar. 2017, vol. 7, Issue 3, pp. 1805-1817.

Fu et al., "Rhodium Bis(quinolinyl)benzene Complexes for Methane Activation and Functionalization," Chemistry A European Journal, 2015, vol. 21, pp. 1286-1293.

Jiang et al., "Pore Surface Engineering with Controlled Loadings of Functional Groups via Click Chemistry in Highly Stable Metal-Organic Frameworks," Journal of the American Chemical Society, 2012, vol. 134, pp. 14690-14693.

Gerken, J. B.; Stahl, S. S., High-potential electrocatalytic 02 reduction with nitroxyl/NOx mediators: Implications for fuel cells and aerobic oxidation catalysis. ACS Cent. Sci. 2015, 1, 234-243.

Gang, X.; Zhu, Y.; Birch, H.; Hjuler, H. A.; Bjerrum, N. J. lodine as Catalyst for the Direct Oxidation of Methane to Methyl Sulfates in Oleum. Appl. Catal., A 2004, 261, 91-98.

Fu, R.; Nielsen, R. J.; Goddard, W. A. III; Fortman, G. C.; Gunnoe, T. B. ACS Catal. 2014, 4, 4455-4465.

Fortman, G. C.; Boaz, N. C.; Munz, D.; Konnick, M. M.; Periana, R. A.; Groves, J. T.; Gunnoe, T. B., Selective Monooxidation of Light Alkanes Using Chloride and lodate. J. Am. Chem. Soc. 2014, 136, 8393-8401.

Fokin, A. A.; Schreiner, P. R. Selective Alkane Transformations via Radicals and Radical Cations: Insights into the Activation Step from Experiment and Theory. Chem. Rev. 2002, 102, 1551-1593.

Fekl, U.; Goldberg, K. I. Adv. Inorg. Chem. 2003, 54, 259-320.

Fattahi, A.; Mccarthy, R. E.; Ahmad, M. R.; Kass, S. R. Why Does Cyclopropane Have the Acidity of an Acetylene but the Bond Energy of Methane? J. Am. Chem. Soc. 2003, 125, 11746-11750.

Donchak, V. A.; Voronov, S. A.; Yur'ev, R. S. New Synthesis of Tert-Butyl Peroxycarboxylates. Russ. J. Org. Chem. 2006, 42, 487-490.

Day, J. C.; Lindstrom, M. J.; Skell, P. S. Succinimidyl Radical as a Chain Carrier. Mechanism of Allylic Bromination. J. Am. Chem. Soc. 1974, 96, 5616-5617.

Davidson, R. I.; Kropp, P. J. Oxidatively Assisted Nucleophilic Substitution/Elimination of Alkyl Iodides in Alcoholic Media. A Further Study. J. Org. Chem. 1982, 47, 1904-1909.

Crabtree, R.H. Aspects of Methane Chemistry. Chem. Rev. 1995, 95, 987-1007.

Coseri, S. Phthalimide-N-Oxyl (PINO) Radical, a Powerful Catalytic Agent: Its Generation and Versatility Towards Various Organic Substrates. Catal. Rev.: Sci. Eng. 2009, 51, 218- 292.

Chepaikin, E. G. Russ. Chem. Rev. 2011, 80, 363-396.

Cheng, W.-H.; Kung, H. H. Methanol Production and Use; Marcel Dekker: New York, NY, 1994; pp. 283-317.

Chen, W.; Kocal, J. A.; Brandvold, T. A.; Bricker, M. L.; Bare, S. R.; Broach, R. W.; Greenlay, N.; Popp, K.; Walenga, J. T.; Yang, S.S.; Low, J. J., Manganese oxide catalyzed methane partial oxidation in trifluoroacetic acid: Catalysis and kinetic analysis. Catal. Today 2009, 140, 157-161.

(56) References Cited

OTHER PUBLICATIONS

Chapter 15.7: Fossil Fuels. In General Chemistry for Engineering; Halpern, J.; Sinex, S.; Johnson, S.; Eds.; Prince George's Community College: Largo, MD, 2016.
Chan, B.; Easton, C. J.; Radom, L. Outcome-Changing Effect of Polarity Reversal in Hydrogen-Atom-Abstraction Reactions. J. Phys. Chem. A 2015, 119, 3843-3847.
Cambie, R. C.; Chambers, D.; Lindsay, B. G.; Rutledge, P. S.; Woodgate, P. D. Oxidative Displacement of Hypervalent Iodine from Alkyl lodides. J. Chem. Soc., Perkin Trans. 1 1980, 0, 822-827.
C. P. Guntlin, T. Zund, K. V. Kravchyk, M. Worle, M. I. Bodnarchuk, M. V. Kovalenko, J. Mater. Chem. A 2017, 5, 7383-7393.
Brooks, D. Shale gas revolution. New York Times, Nov. 3, 2011, p. A31.
Breed, A.; Doherty, M. F.; Gadewar, S.; Grosso, P.; Lorkovic, I. M.; McFarland, E. W.; Weiss, M. Natural Gas Conversion to Liquid Fuels in a Zone Reactor. Catal. Today 2005, 106, 301-304.
BP Statistical Review of World Energy 2014; BP: London, 2014.
Blanksby, S. J.; Ellison, G. B. Bond Dissociation Energies of Organic Molecules. Acc. Chem. Res. 2003, 36, 255-263.
Bering, L.; Antonchick, A. P. Selective Transition-Metal-Free Vicinal Cis-Dihydroxylation of Saturated Hydrocarbons. Chem. Sci. 2017, 8, 452-457.
Benson, S. W. III—Bond Energies. J. Chem. Ed. 1965, 42, 502.
Bell, H. C.; Kalman, J. R.; Pinhey, J. T.; Sternhell, S. Aust. J. Chem., 1979, 32, 1521-1530.
Barton, D. H. R.; Martell, A. E.; Sawyer, D. T. In The Activation of Dioxygen and Homogeneous Catalytic Oxidation, Fifth International Symposium on the Activation of Dioxygen and Homogeneous Catalytic Oxidation, College Station, TX, Springer Science and Business Media, LLC: College Station, TX, 1993.
Arndtsen, B. A.; Bergman, R. G.; Mobley, T. A.; Peterson, T. H. Selective Intermolecular Carbon-Hydrogen Bond Activation by Synthetic Metal Complexes in Homogeneous Solution. Acc. Chem. Res. 1995, 28, 154-162.
Aglulin, A.G. Kinet. Catal. 2009, 50, 427-434.
Koshino, N.; Cai, Y.; Espenson, J. H. Kinetic Study of the Phthalimide N-Oxyl (PINO) Radical in Acetic Acid. Hydrogen Abstraction from C—H Bonds and Evaluation of O—H Bond Dissociation Energy of N-Hydroxyphthalimide. J. Phys. Chem. A 2003, 107, 4262-4267.
Konnick, M. M.; Hashiguchi, B. G.; Devarajan, D.; Boaz, N. C.; Gunnoe, T. B.; Groves, J. T.; Ess, D. H.; Periana, R. A. Electrophilic C—H Functionalization of Methane, Ethane and Propane by a Perfluoroarene lodine(III) Complex in Carboxylic Acid Media. Angew. Chem., Int. Ed. 2014, 53, 10490-10494.
Kao, L. C.; Hutson, A. C.; Sen, A. J. Am. Chem. Soc. 1991, 113, 700-701.
Kalman, S. E.; Munz, D.; Fortman, G. C.; Boaz, N. C.; Groves, J. T.; Gunnoe, T. B. Partial Oxidation of Light Alkanes by Periodate and Chloride Salts. Dalton Trans. 2015, 44, 5294- 5298.
Jones, C. J.; Taube, D.; Ziatdinov, V. R.; Periana, R. A.; Nielsen, R. J.; Oxgaard, J.; Goddard III, W. A. Selective Oxidation of Methane to Methanol Catalyzed, with C—H Activation, by Homogeneous, Cationic Gold. Angew. Chem., Int. Ed. 2004, 116, 4726-4729.
Jaronsinska, M.; Lubkowski, K.; Sosnicki, J. G.; Michalkiewicz, B. Application of Halogens as Catalysts of CH4 Esterification. Catal. Lett. 2008, 126, 407-412.
Hook, S. C. W.; Saville, B. The Trapping of Carbon Radicals. The Competition of Oxygen and lodine for the 1,1-Diphenylethyl Radical. J. Chem. Soc., Perkin Trans. 2 1975, 589-593.
Hermans, I.; Jacobs, P.; Peeters, J. Autoxidation Catalysis with N-Hydroxyimides: Mor•• Reactive Radicals or Just More Radicals? Phys. Chem. Chem. Phys. 2007, 9, 686-690.
He, J.; Xu, T.; Wang, Z.; Zhang, Q.; Deng, W.; Wang, Y. Transformation of Methane to Propylene: A Two-Step Reaction Route Catalyzed by Modified CeO2 Nanocrystals and Zeolites. Angew. Chem., Int. Ed. 2012, 51, 2438-2442.
Hashiguchi, B. G.; Konnick, M. M.; Bischof, S. M.; Gustafson, S. J.; Devarajan, D.; Gunsalus, N.; Ess, D. H.; Periana, R. A. Main-Group Compounds Selectively Oxidize Mixtures of Methane, Ethane, and Propane to Alcohol Esters. Science 2014, 343, 1232-1237.
Gunsalus, N. J.; Koppaka, A.; Park, S. H.; Bischof, S. M.; Hashiguchi, B. G.; Periana, R.A. Homogeneous Functionalization of Methane. Chem. Rev. 2017, 117, 8497-8520.
Goldshlegger, N. F.; Tyabin, M. B.; Shilov, A. E.; Shteinman, A. A. Zh. Fiz. Khim. 1969, 43,2174-2175.
Goldshlegger, N. F.; Eskova, V. V.; Shilov, A. E.; Shteinman, A. A. Zh. Fiz. Khim. 1972, 46, 1353-1354.
Goldberg, K. I.; Goldman, A. S. Large-Scale Selective Functionalization of Alkanes. Acc. Chem. Res. 2017, 50, 620-626.
Olah, G. A.; Goeppert, A.; Prakash, G. K. S. Beyond Oil and Gas: The Methanol Economy, Wiley-VCH Verlag GmbH & Co. KGaA, Weinheim, Germany: 2009; p. 179.
National Renewable Energy Laboratory. Subcontract Report NREL/SR-510-39943: Equipment Design and Cost Estimation for Small Modular Biomass Systems, Synthesis Gas Cleanup, and Oxygen Separation Equipment. http://www.nrel.gov/docs/fy06osti/39943.pdf (accessed Jan. 29, 2017).
Munz, D.; Webster-Gardiner, M. S.; Fu, R.; Strassner, T.; Goddard, W. A. III; Gunnoe, T. B. ACS Catal. 2015, 5, 769-775.
Mosher, M. W.; Estes, G. W. Free-Radical Halogenations. Chlorination of Alkanes by •• Chlorophthalimide. J. Am. Chem. Soc. 1977, 99, 6928-6932.
Michalkiewicz, B.; Jaronsinska, M.; tukasiewicz, I. Kinetic Study on Catalytic Methane Esterification in Oleum Catalyzed by Iodine. Chem. Eng. J. 2009, 154, 156-161.
Michalkiewicz, B. Methane Oxidation to Methyl Bisulfate in Oleum at Ambient Pressure in the Presence of Iodine as a Catalyst. Appl. Catal., A 2011, 394, 266-268.
Mezyk, S. P.; Madden, K. P. Arrhenius Parameter Determination for the Reaction of Methyl Radicals with lodine Species in Aqueous Solution. J. Phys. Chem. 1996, 100, 9360-9364.
McFarland, E. Unconventional Chemistry for Unconventional Natural Gas. Science 2012, 338, 340-342.
Martens, J. A.; Bogaerts, A.; De Kimpe, N.; Jacobs, P.A.; Marin, G.; Rabaey, K.; Saeys, M.; Verhelst, S. The Chemical Route to a Carbon Dioxide Neutral World. ChemSusChem 2017, 10, 1039-1055.
Marchaj, A.; Kelley, D. G.; Bakac, A.; Espenson, J. H. Kinetics of the Reactions between Alkyl Radicals and Molecular Oxygen in Aqueous Solution. J. Phys. Chem. 1991, 95, 4440-4441.
Magistro, A. J.; Nicholas, P. P.; Carroll, R. T., Oxychlorination of ethylene at high temperatures. J. Org. Chem. 1969, 34 (2), 271-273.
Macdonald, T. L.; Narasimhan, N.; Burka, L. T. Chemical and Biological Oxidation of Organohalides. J. Am. Chem. Soc. 1980, 102, 7760-7765.
Lin, R.; Ding, Y.; Gong, L.; Li, J.; Chen, W.; Yan, L.; Lu, Y. Oxidative Bromination of Methane on Silica-Supported Non-Noble Metal Oxide Catalysts. Appl. Catal., A. 2009, 353, 87-92.
Lin, R.; Ding, Y.; Gong, L.; Dong, W.; Wang, J.; Zhang, T. Efficient and Stable Silica. Supported Iron Phosphate Catalysts for Oxidative Bromination of Methane. J. Catal. 2010, 272, 65-73.
Lin, R.; Amrute, A. P.; Perez-Ramirez, J. Halogen-Mediated Conversion of Hydrocarbons to Commodities. Chem. Rev. 2017, 117, 4182-4247.
Leyva-Perez, A.; C6mbita-Merchan, D.; Cabrero-Antonino, J. R.; Al-Resayes, S. A.; Corma, A., Oxyhalogenation of activated arenes with nanocrystalline ceria. ACS Catal. 2013, 3 (2), 250-258.
Lersch, M.; Tilset, M. Chem. Rev. 2005, 105, 2471-2526.
Labinger, J. A. Selective Alkane Oxidation: Hot and Cold Approaches to a Hot Problem. J. Mol. Catal. A: Chem. 2004, 220, 27-35.
Podkolzin, S. G.; Stangland, E. E.; Jones, M. E.; Peringer, E.; Lercher, J. A. Methyl Chloride Production from Methane over Lanthanum-Based Catalysts. J. Am. Chem. Soc. 2007, 129, 2569-2576.
Pieters, W. J. M.; Conner, W. C.; Carlson, E. J. The Oxyhydrochlorination of Methane on Fumed Silica-Based Cu(I), K, La Catalysts: I. Catalyst Synthesis. Appl. Catal. 1984, 11, 35-48.
Periana, R. A.; Taube, D. J.; Evitt, E. R.; Loffler, D. G.; Wentrcek, P.R.; Voss, G.; Masuda, T. A Mercury-Catalyzed, High-Yield System for the Oxidation of Methane to Methanol. Science 1993, 259, 340-343.

(56) References Cited

OTHER PUBLICATIONS

Periana, R. A.; Mirinov, O.; Taube, D. J.; Gamble, S. High Yield Conversion of Methane to Methyl Bisulfate Catalyzed by Iodine Cations. Chem Commun. 2002, 2376-2377.
Paunovic, V.; Zichitella, G.; Moser, M.; Amrute, A. P.; Perez-Ramirez, Catalyst Design for Natural-Gas Upgrading through Oxybromination Chemistry. J. Nat. Chem. 2016, 8, 803-809.
Pachauri, R. K.; Reisinger, A. The Fourth Assessment Report of the Intergovernmental Panel on Climate Change; Working Group 1: Geneva, Switzerland, 2007, Chapter 2.
Owen, J. S.; Labinger, J. A.; Bercaw, J. E. Kinetics and Mechanism of Methane, Methanol, and Dimethyl Ether C—H Activation with Electrophilic Platinum Complexes. J. Am. Chem. Soc. 2006, 128, 2005-2016.
Schwach, P.; Pan, X.; Bao, X. Direct Conversion of Methane to Value-Added Chemicals over Heterogeneous Catalysts: Challenges and Prospects. Chem. Rev. 2017, 117, 8497-8520.
Schnoor, J. L. Shale Gas and Hydrofracturing. Environ. Sci. Tech. 2012, 46, 4686.
Scharfe, M.; Lira-Parada, P.A.; Paunovic, V.; Moser, M.; Amrute, A. P.; Perez-Ramirez, J., Oxychlorination-dehydrochlorination chemistry on bifunctional ceria catalysts for intensified vinyl chloride production. Angew. Chem. Int. Ed. 2016, 55 (9), 3068-3072.
Scharfe, M.; Capdevila-Cortada, M.; Kondratenko, V. A.; Kontratenko, E. V.; Colussi, S.; Trovarelli, A.; Lopez, N.; Perez-Ramirez, J., Mechanism of ethylene oxychlorination on ceria. ACS Catal. 2018, 8 (4), 2651-2663.
Sakakura, A.; Kawajiri, K.; Ohkubo, T.; Kosugi, Y.; Ishihara, K. Widely Useful DMA•• Catalyzed Esterification under Auxiliary Base- and Solvent-Free Conditions. J. Am. Chem. Soc. 2007, 129, 14775-14779.
Rueda-Becerril, M.; Chatalova Sazepin, C.; Leung, J.C. T.; Okbinoglu, T.; Kennepohl, P.; Paquin, J.-F.; Sammis, G. M. Fluorine Transfer to Alkyl Radicals. J. Am. Chem. Soc. 2012, 134, 4026-4029.
Rozanov, V. N.; Gvozd, E. V.; Kernerman, V. A.; Svetlanov, E. B.; Trushechkina, M.A.; Treger, Y. A. Kinet. Catal. 1989, 30, 148-154.
Rosen, M. A.; Scott, D. S. Energy and Exergy Analyses of a Production Process for Methanol from Natural Gas. Int. J. Hydrogen Energy 1988, 13, 617-623.
Strassner, T.; Ahrens, S.; Muehlhofer, M.; Munz, D.; Zeller, A., Cobalt-Catalyzed Oxidation of Methane to Methyl Trifluoroacetate by Dioxygen. Eur. J. Inorg. Chem. 2013, 2013 (21), 3659-3663.
Stauffer, J. E. Process for the Chlorination of Methane. World Patent 9008117A1, Jul. 26, 1990.
Solymosi, F.; Jaky, K. Stability of Ammonium Halates in the Solid State: Kinetic Study of the Thermal Decomposition of Ammonium Iodate. J. Inorg. Nucl. Chem. 1971, 33, 2829-2838.
Smith, G. W.; Williams, H. D. Some Reactions of Adamantane and Adamantane Derivatives. J. Org. Chem. 1961, 26, 2207-2212.
Shilov, A. E.; Shul'pin, G. B. Activation and Catalytic Reactions of Saturated Hydrocarbons in the Presence of Metal Complexes; Kluwer Academic Publishers: Dordrecht, 2000; pp. 259-317.
Shilov, A. E.; Shul'pin, G. B. Activation and Catalytic Reactions of Alkanes in Solutions of Metal Complexes. Russ. Chem. Rev. 1987, 56, 442-464.
Shalygin, A.; Paukshtis, E.; Kovalyov, E.; Bal'zhinimaev, B. Light Olefins Synthesis from C1-C2 Paraffins via Oxychlorination Processes. Front. Sci. Eng. 2013, 7, 279-288.
Sen, A. Catalytic Functionalization of Carbon-Hydrogen and Carbon-Carbon Bonds in Protic Media. Acc. Chem. Res. 1998, 31, 550-557.
Schwartz, N. A.; Boaz, N. C.; Kalman, S. E.; Zhuang, T.; Goldberg, J.M.; Fu, R.; Nielsen, R. J.; Goddard III, W. A.; Groves, J. T.; Gunnoe, T. B., Mechanism of Hydrocarbon Functionalization by and Iodate/Chloride System: The Role of Ester Protection. ACS Catal. 2018, 8, 3138-3149.
Wang, X.; Liu, Y.; Zhang, Y.; Zhang, T.; Chang, H.; Zhang, Y.; Jiang, L., Structural requirements of manganese oxides for methane oxidation: XAS spectroscopy and transition state studies. Appl. Catal. B 2018, 229, 52-62.
Wang, R.; Lin, R.; Ding, Y.; Liu, J.; Wang, J.; Zhang, T. Structure and Phase Analysis of One-Pot Hydrothermally Synthesized FePO4-SBA-15 as an Extremely Stable Catalyst for Harsh Oxy-Bromination of Methane. Appl. Catal., A. 2013, 453, 235-243.
Wang, R.; Lin, R.; Ding, Y.; Liu, J. Model Iron Phosphate Catalysts for the Oxy-Bromination of Methane. Catal. Lett. 2014, 144, 1384-1392.
Wang, Q.; Chen, X.; Jha, A. N.; Rogers, H. Natural Gas from Shale Formation—The Evolution, Evidences and Challenges of Shale Gas Revolution in United States. Renewable Sustainable Energy Rev. 2014, 30, 1-28.
Wang, K. X.; Xu, H.F.; Li, W. S.; Zhou, X. P. Acetic Acid Synthesis from Methane by Non• Synthetic Gas Process. J. Mol. Catal. A: Chem. 2005, 225, 65-69.
Walling, C.; Mayahi, M. F. Some Solvent and Structural Effects in Free Radical Chlorination. J. Am. Chem. Soc. 1959, 81, 1485-1489.
Tschuikow-Roux, E.; Paddison, S. Bond Dissociation Energies and Radical Heats of Formation in CH3Cl, CH2Cl2, CH3Br, CH2Br2, CH2FCl, and CHFCl2. Int. J. Chem. Kinet. 1987, 19, 15-24.
Tedder, J.M. Which Factors Determine the Reactivity and Regioselectivity of Free Radical Substitution and Addition Reactions? Angew. Chem., Int. Ed. 1982, 21, 401-410.
Taylor, C. E.; Noceti, R. P.; Schehl, R. R. Direct Conversion of Methane to Liquid Hydrocarbons through Chlorocarbon Intermediates. Stud. Surf. Sci. Catal. 1988, 36, 483-489.
Tabushi, I.; Hamuro, J.; Oda, R. Free-Radical Substitution on Adamantane. J. Am. Chem. Soc. 1967, 89, 7127-7129.
Zhdankin, V. V.; Stang, P. J. Chemistry of Polyvalent Iodine. Chem. Rev. 2008, 108, 5299- 5358.
Zhdankin, V. V. Hypervalent lodine(III) Reagents in Organic Synthesis. Arkivoc 2009, 1-62. (2974-3034).
Zefirov, N. S.; Zhdankin, V. V.; Makhon'kova, G. V.; Dan'kov, Y. V.; Koz'min, A. S. Oxidatively Assisted Nucleophilic Substitution of Iodine in Alkyl lodides by Nucleofugic Anions. J. Org. Chem. 1985, 50, 1872-1876.
Zakaria, Z.; Kamarudin, S. K. Direct Conversion Technologies of Methane to Methanol: An Overview. Renewable Sustainable Energy Rev. 2016, 65, 250-261.
Wittcoff, H. A.; Reuben, B. G.; Plotkin, J. S. Industrial Organic Chemicals. John Wiley & Sons: Hoboken, NJ, 2012, p. 459.
Webster-Gardiner, M. S.; Piszel, P. E.; Fu, R.; Chen, J.; McKeown, B. A.; Nielsen, R. J.; Goddard, W. A. III; Gunnoe, T. B. J. Mol. Catal. A: Chem. 2017, 426B, 381-388.
Webster-Gardiner, M. S.; Fu, R.; Fortman, G. C.; Nielsen, R. J.; Gunnoe, T. B.; Goddard, W. A. III. Catal. Sci. Technol. 2015, 5, 96-100; d. Fu, R.; O'Reilly, M. E.; Nielsen, R. J.; Goddard, W. A. III; Gunnoe, T. B. Chem. Eur. J. 2015, 21, 1286-1293.
Webb, J. R.; Solano, T.; Gunnoe, T. B. Catalytic Oxy-Functionalization of Methane and Other Hydrocarbons: Fundamental Advancements and New Strategies. ChemSusChem 2011, 4, 37-49.
Zichitella, G.; Paunovic, V.; Amrute, A. P.; Perez-Ramirez, J. Catalytic Oxychlorination versus Oxybromination for Methane Functionalization. ACS Catal. 2017, 7, 1805-1817.
Zhou, K.; Wang, W.; Zhao, Z.; Luo, G.; Miller, J. T.; Wong, M. S.; Wei, F., Synergistic gol•• bismuth catalysis for non-mercury hydrochlorination of acetylene to vinyl chloride monomer. ACS Catal. 2014, 4 (9), 3112-3116.
Liu, Z.; Huang, L.; Li, W. S.; Yang, F.; Au, C. T.; Zhou, X. P. Higher Hydrocarbons from Methane Condensation Mediated by HBr. J. Mol. Catal. A: Chem. 2007, 273, 14-20.
Koval, I. V. N-Halosuccinimides in Organic Synthesis and in Chemistry of Natural Compounds. Russ. J. Org. Chem. 2002, 38, 301-337.
Conley, B. L.; Tenn, W. J.; Young, K. J. H.; Ganesh, S. K.; Meier, S. K.; Ziatdinov, V. R.; Mironov, O.; Oxgaard, J.; Gonzales, J.; Goddard III, W. A.; Periana, R. A. Design and Study of Homogeneous Catalysts for the Selective, Low Temperature Oxidation of Hydrocarbons. J. Mol. Catal. A: Chem. 2006, 251, 8-23.

* cited by examiner

METHODS FOR FUNCTIONALIZATION HYDROCARBONS

CROSS REFERENCE TO RELATED APPLICATIONS

This application claims priority upon U.S. provisional application Ser. No. 62/817,594 filed on Mar. 13, 2019. This application is hereby incorporated by reference in its entirety.

STATEMENT REGARDING FEDERALLY SPONSORED RESEARCH OR DEVELOPMENT

This invention was made with U.S. Government support under grant number DE-AC07-051D14517 awarded by the Department of Energy. The U.S. government has certain rights in the invention.

BACKGROUND

Natural gas is a naturally-occurring gaseous mixture composed chiefly of methane that is generally found in the same places as petroleum. However, methane is a gas with a very low boiling point of −161.5° C., making it difficult to liquefy, and consequently expensive to store and transport. Because natural gas sells for a much lower price than petroleum on the world market, it is often uneconomical to harvest. And because it is also a potent greenhouse gas with 72 times the climate change potential of carbon dioxide, release into the atmosphere can have significantly deleterious environmental effects. It has been estimated that 140 billion cubic meters of natural gas are flared annually, representing a colossal waste of energy (enough to power half of Africa).

Much effort has been expended towards partially oxidizing methane to methanol onsite. As a liquid under standard conditions and a common chemical feedstock, methanol is both easier to store and transport, and also more valuable than methane. An industrial process that is frequently used is called steam-methane reformation (SMR), in which a mixture of methane and steam is passed through a nickel catalyst at high temperatures and pressures to form synthesis gas (syngas, carbon monoxide and dihydrogen), which is then recombined in a second catalytic process to form methanol. Unfortunately, this process is both highly energy and capital intensive, and it is generally not feasible to be located near remote extraction sites. Another strategy for methane functionalization is methane oxychlorination, which involves the catalyzed reaction of methane with HCl and $O_2$ to form methyl chloride and water. The products can further react to produce methanol and regenerate HCl. Unfortunately, this process produces a large amount of overoxidized byproducts such as methylene chloride, chloroform, and carbon tetrachloride. In fact, a common limitation of radical based mechanisms such as oxychlorination is the fact that the C—H bond of methane, 104 kcal/mol, is stronger than that of methanol (96 kcal/mol) or methyl chloride (100 kcal/mol), leading to abundant overoxidized side products that have reduced value.[

In the 1960s, it was discovered that platinum salts in aqueous HCl solution could activate methane under mild conditions, producing methyl chloride (and consequently methanol by hydrolysis) through an electrophilic two-electron C—H activation mechanism. For this process, Pt(IV) was used as the stoichiometric oxidant. In the ensuing decades, much work has been done to improve catalyst stability, find less expensive alternatives to platinum, and use dioxygen as the stoichiometric terminal oxidant. One of the most promising developments is the Catalytica process, in which methane in oleum solution ($H_2SO_4/SO_3$) is oxidized to methyl bisulfate via diverse late-transition metals such as Pt, Pd, Hg, and Au. In all of these cases, the reaction is selective for methyl bisulfate production, often with negligible over-oxidation. This has been attributed to the presence of the electron withdrawing group —$OSO_3H$ which serves as a protecting group, removing electron density from the methyl C—H bond and hence making over-oxidation by electrophilic catalysts slower. Importantly, it is the combination of an electrophilic catalyst and the electron-withdrawing group —$OSO_3H$ that reduces the reactivity of methyl bisulfate. Currently, the chief drawback of the Catalytica family of methane oxidation systems is the use of superacidic media such as oleum, which must be constantly replenished due to $H_2O$ being produced by the reaction, rendering cost-effective product extraction very difficult.

It would be advantageous to have a process for conversion of natural gas to liquid for storage and transportation purposes. It would further be advantageous if that process could be extended to functionalize other hydrocarbons. It would be particularly desirable if the process could take place under less acidic environments than currently known processes, and if the process used inexpensive reagents, including oxidants that can be regenerated. It would further be desirable if the process operated with selectivity and could be carried out under relatively mild temperature conditions. The present disclosure satisfies these needs.

SUMMARY

In accordance with the purpose(s) of the present disclosure, as embodied and broadly described herein, the disclosure, in one aspect, relates to a method for functionalizing hydrocarbons. In one aspect, the method involves heating a hydrocarbon with a composition having an acid and an oxidant. In other aspects, the composition can further include an iodine-based compound and/or a compound having formula $A_aX_n$. In any of these aspects, the oxidant can be regenerated in situ or in a separate regeneration step. Also disclosed are functionalized hydrocarbons produced by the disclosed method.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

Conditions: $CH_4$ (300 psi), $MnO_2$ (1.1 mmol), HTFA (8 mL), 180° C., 1 h. Error bars denote standard deviations based on three experiments.

Figure 10:
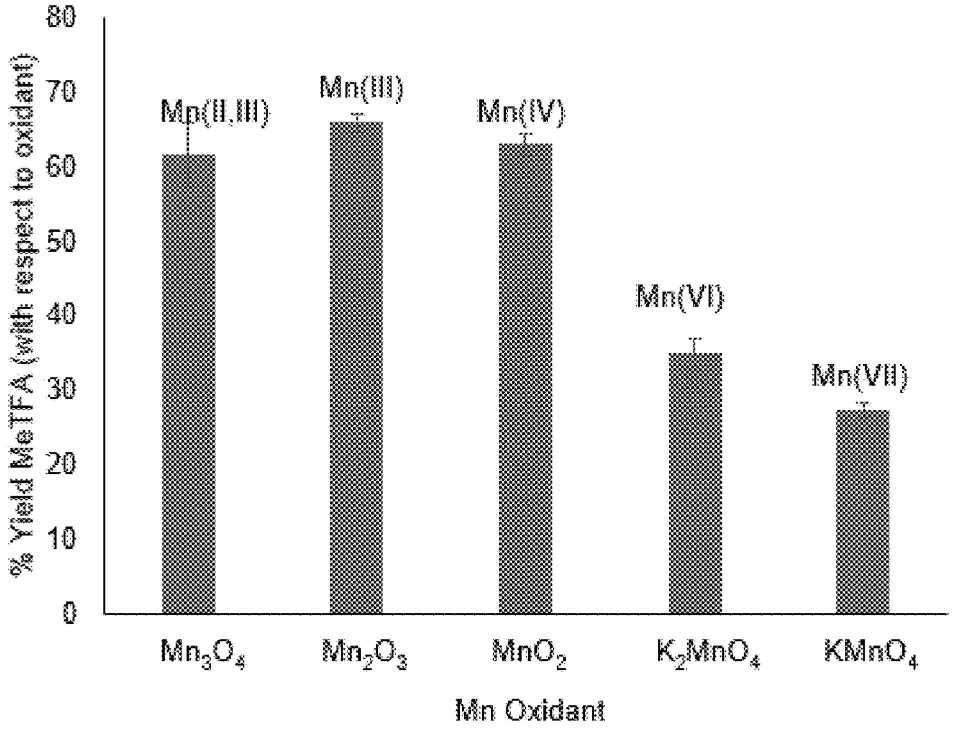

FIG. 10 shows screening of Mn oxidants for methane functionalization. Conditions: $CH_4$ (300 psi), Mn source (1.1 mmol), $I_2$ (0.15 mmol), HTFA (8 mL), 180° C., 1 h. Error bars denote standard deviations based on three experiments. Above the bars are the oxidation states of manganese in each oxidant.

Figure 11:
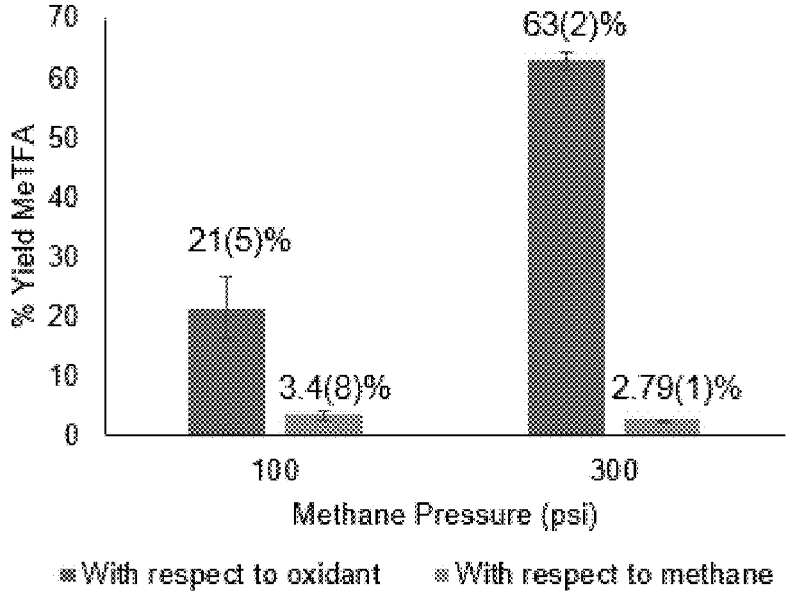

FIG. 11 shows methane functionalization with $MnO_2$/$I_2$ as a function of methane pressure. Conditions: $CH_4$ (100 or 300 psi), $MnO_2$ (1.1 mmol), $I_2$ (0.15 mmol), HTFA (8 mL), 180° C., 1 h. Error bars denote standard deviations based on three experiments.

Figure 12:
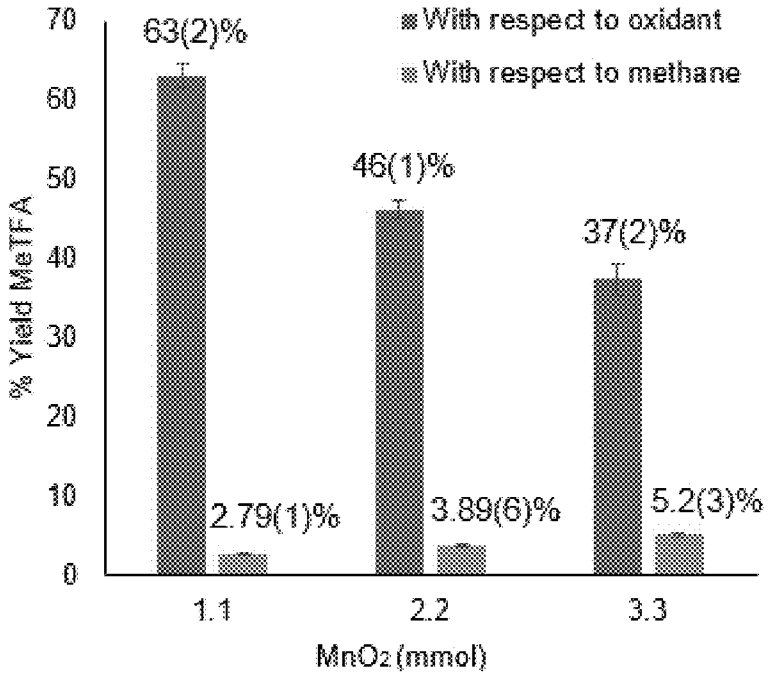

FIG. 12 shows methane functionalization with $MnO_2$/$I_2$ as a function of $MnO_2$ loading. Conditions: $CH_4$ (300 psi), $MnO_2$ (1.1-3.3 mmol), $I_2$ (0.15 mmol), HTFA (8 mL), 180° C., 1 h. Error bars denote standard deviations based on three experiments.

Figure 13:
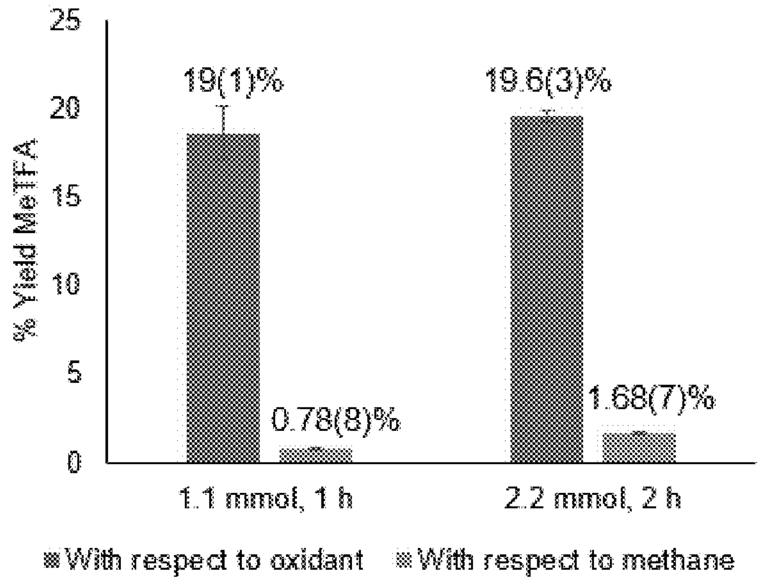

FIG. 13 shows methane functionalization with $M(OAc)_3 \cdot 2H_2O/I_2$ as a function of 12 loading. Conditions: $CH_4$ (300 psi), $Mn(OAc)_3 \cdot 2H_2O$ (1.1 or 2.2 mmol), $I_2$ (0.15 mmol), HTFA (8 mL), 180° C., 1 or 2 h. Error bars denote standard deviations based on three experiments.

Figure 14:
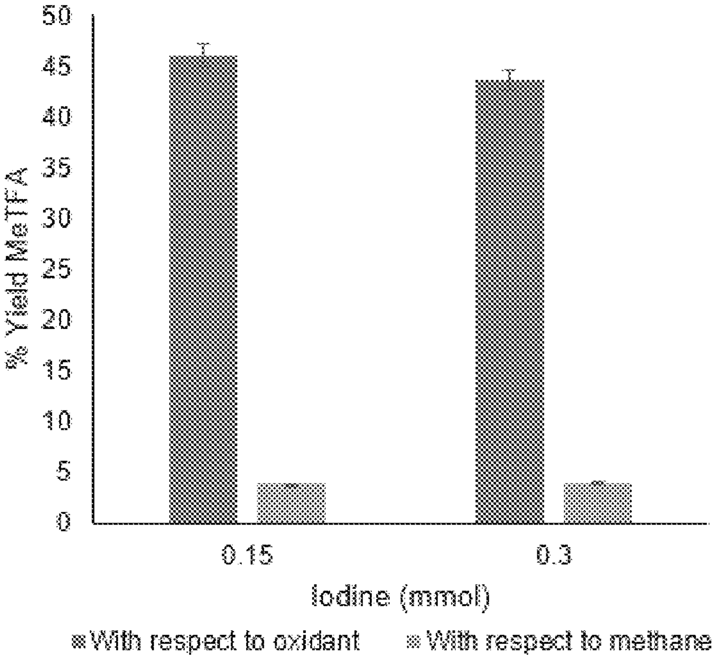

FIG. 14 shows methane functionalization with $MnO_2$/$I_2$ as a function of 12 loading. Conditions: $CH_4$ (300 psi), $MnO_2$ (2.2 mmol), $I_2$ (0.15 or 0.3 mmol), HTFA (8 mL), 180° C., 1 h. Error bars denote standard deviations based on three experiments.

Figure 15:
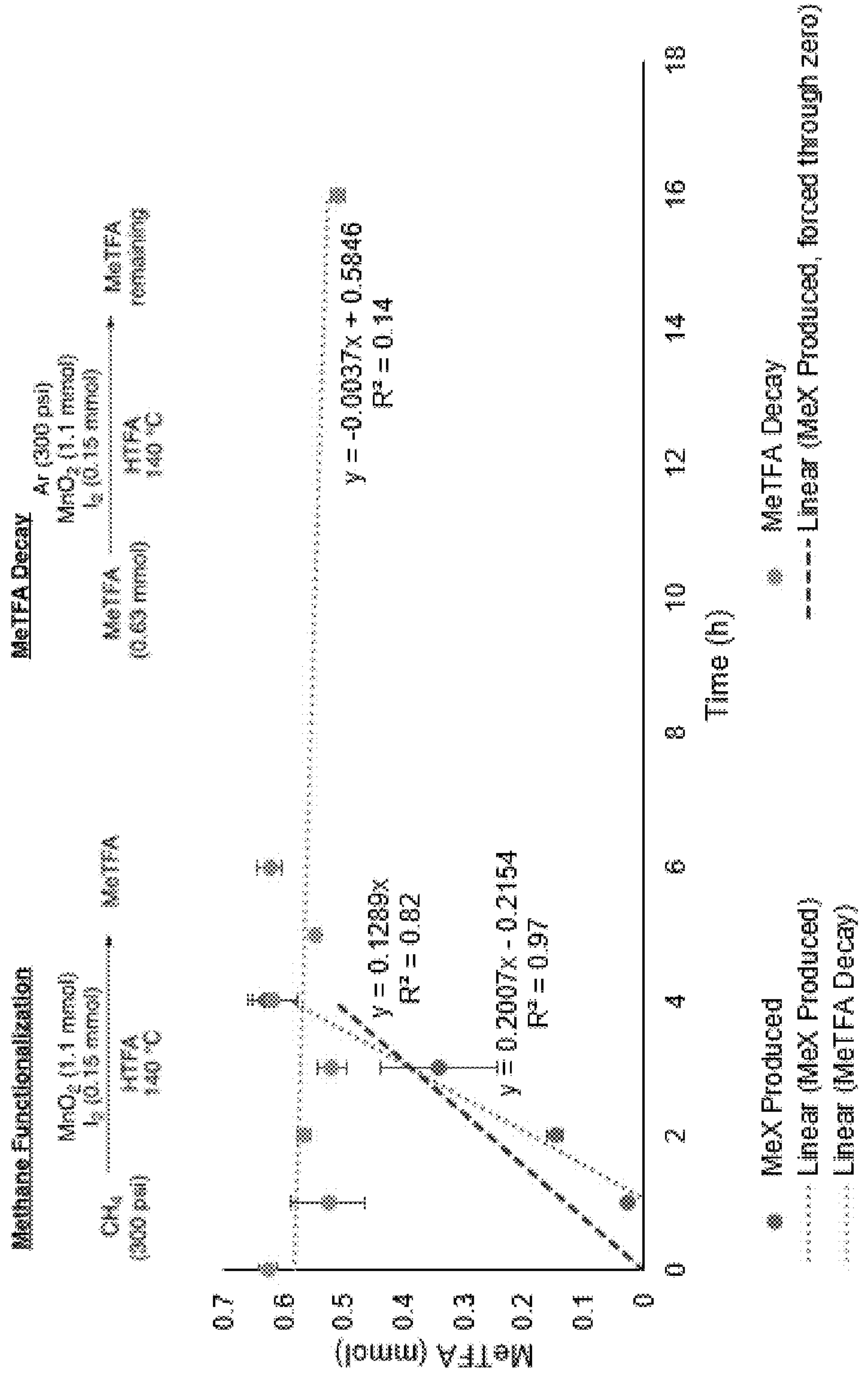

FIG. 15 shows methane functionalization versus MeTFA decay using $MnO_2$/$I_2$. Methane functionalization conditions: $CH_4$ (300 psi), $MnO_2$ (1.1 mmol), $I_2$ (0.15 mmol), HTFA (8 mL), 140° C. MeTFA decay conditions: MeTFA (0.63 mmol), Ar (300 psi), $MnO_2$ (1.1 mmol), $I_2$ (0.15 mmol), HTFA (8 mL), 140° C. Error bars denote standard deviations based on three experiments.

Figure 16:
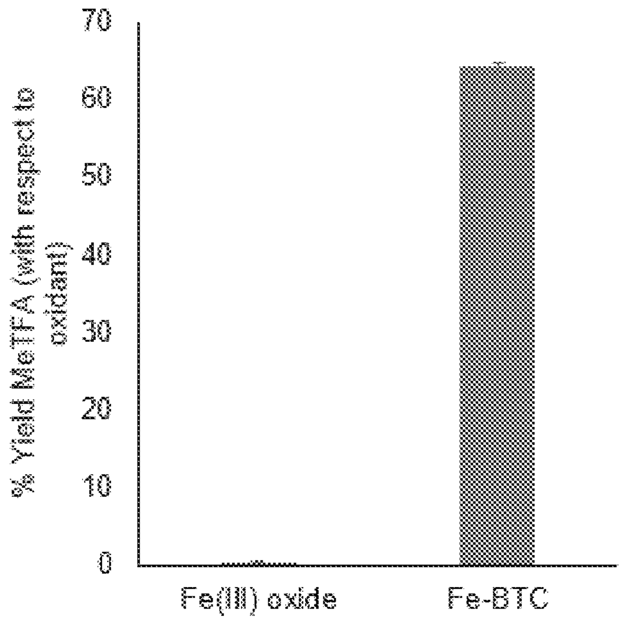

FIG. 16 shows methane functionalization using iron-based oxidants with KCl in HTFA. Conditions: $CH_4$ (300 psi), $Fe_2O_3$ or Fe-BTC (iron 1,3,5-benezetricarboxylate, 1.1 mmol), HTFA (8 mL), 180° C., 1 h. Error bars denote standard deviations based on three experiments.

Figure 17:
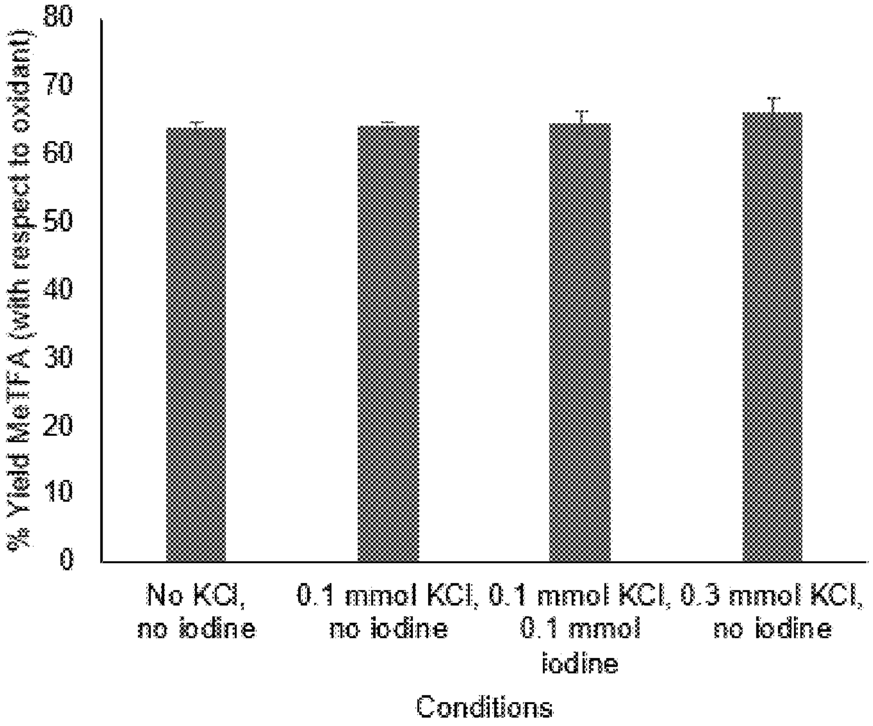

FIG. 17 shows additive screening using Fe-BTC for methane functionalization. Conditions: $CH_4$ (300 psi), Fe-BTC (1.1 mmol), KCl (0-0.3 mmol), $I_2$ (0-0.1 mmol), HTFA (8 mL), 180° C., 1 h. Error bars denote standard deviations based on three experiments.

Figure 18:
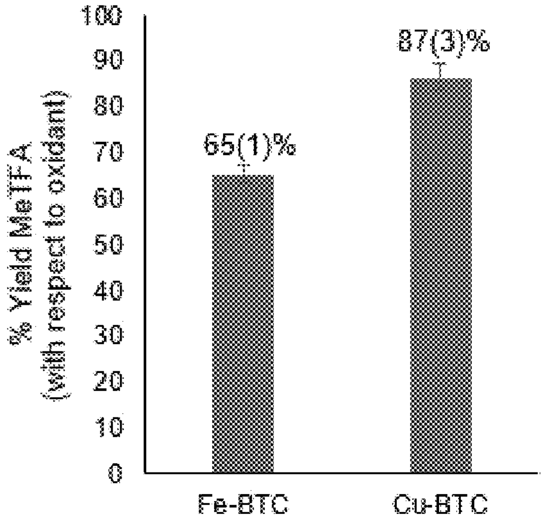

FIG. 18 shows comparison of Fe-BTC and Cu-BTC for the partial oxidation of methane to MeTFA. Conditions: $CH_4$ (300 psi), Cu-BTC or Fe-BTC (0.1 mmol), HTFA (8 mL), 180° C., 1 h. All reactions were set up under ambient atmosphere.

Figure 19:
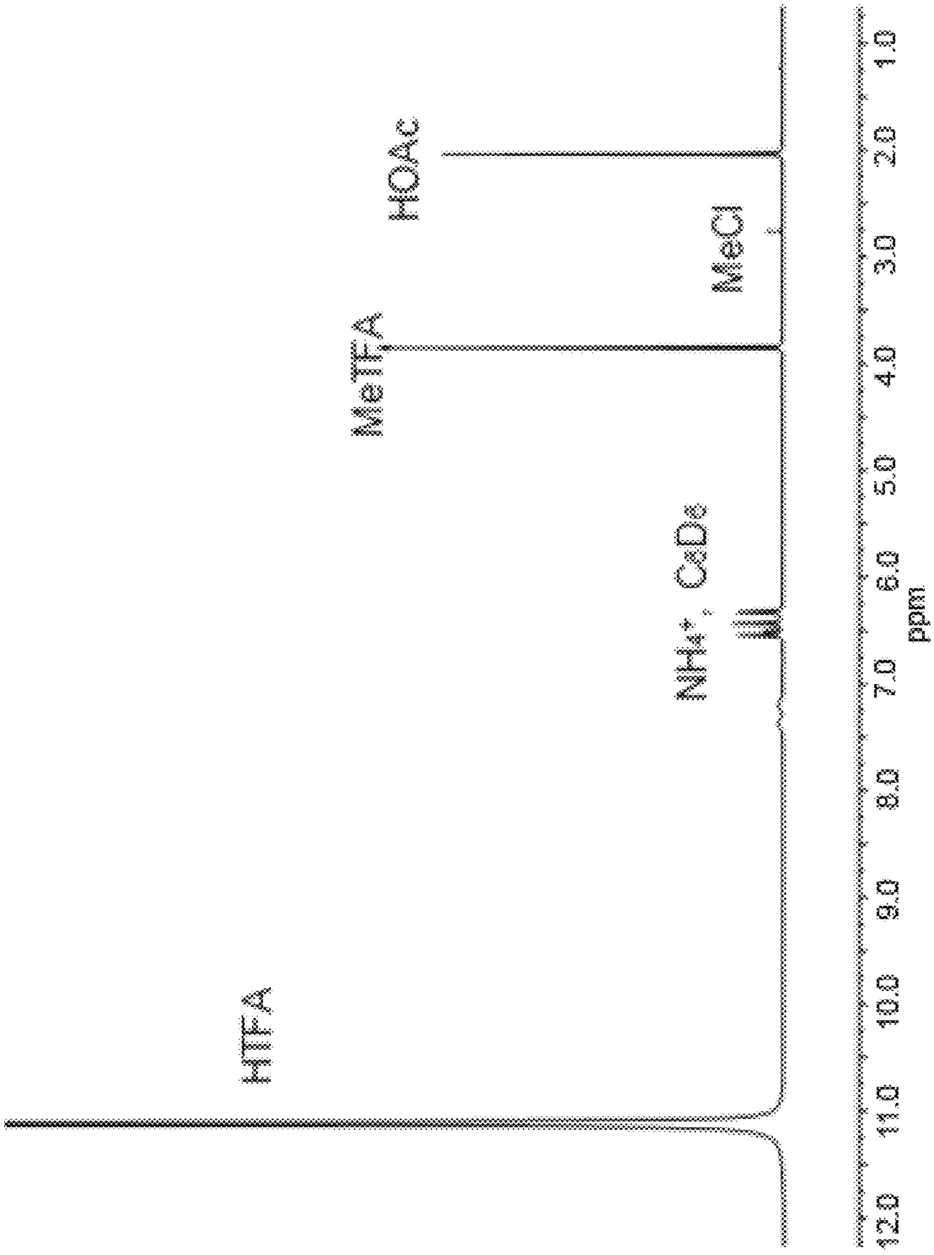

FIG. 19 shows a representative $^1H$ NMR spectrum of methane functionalization with KCl/$NH_4IO_3$ in HTFA. Conditions: $CH_4$ (300 psi), KCl (0.1 mmol), $NH_4IO_3$ (1.1 mmol), HTFA (8 mL), 180° C., 1 h. HOAc (0.35 mmol) was added as an internal standard.

Figure 20:
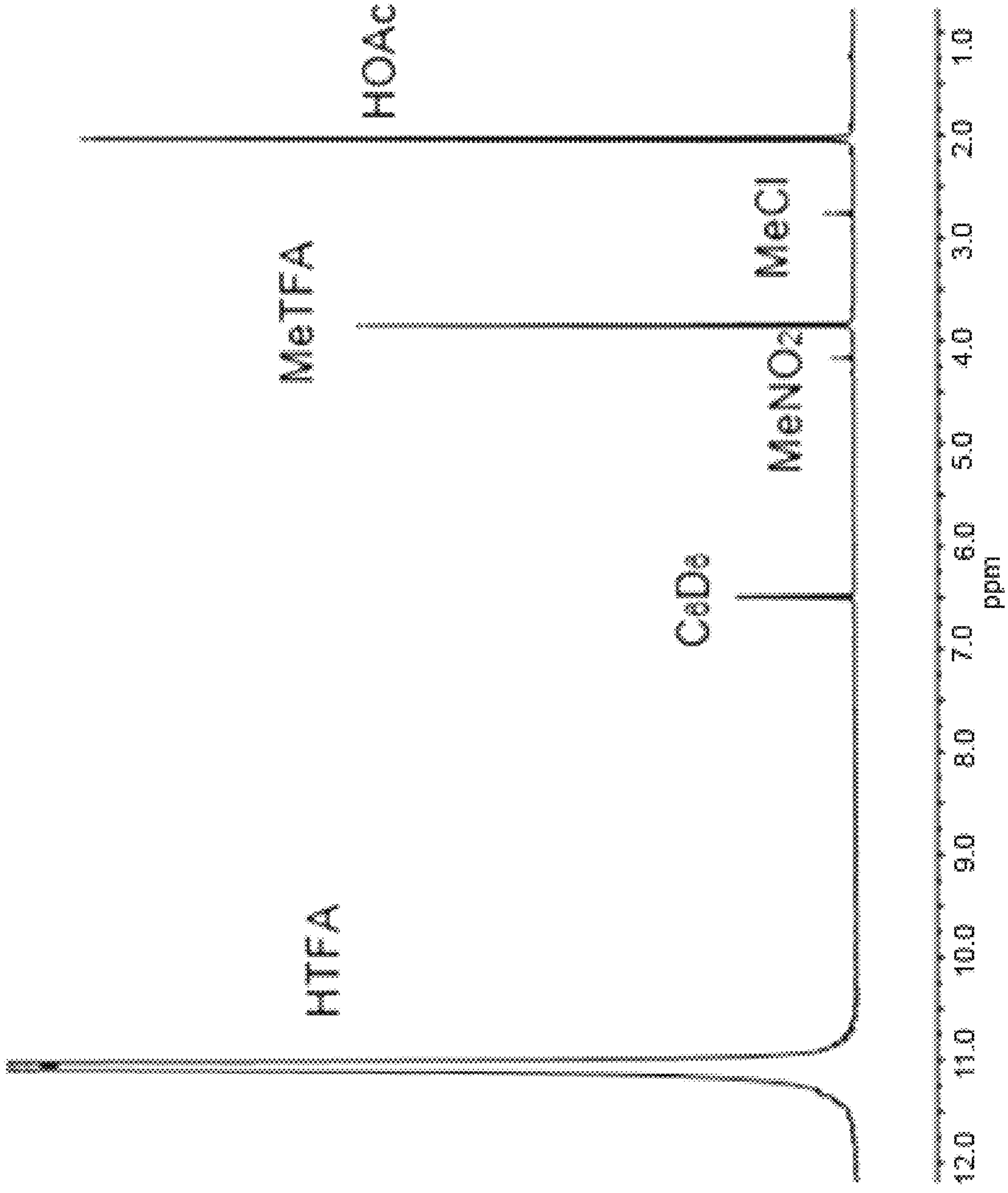

FIG. 20 shows a representative $^1H$ NMR spectrum of methane functionalization with KCl/$NH_4NO_3$/$I_2$ in HTFA. Conditions: $CH_4$ (300 psi), KCl (0.1 mmol), $NH_4NO_3$ (1.1 mmol), $I_2$ (0.1 mmol), HTFA (8 mL), 180° C., 2 h. HOAc (0.35 mmol) was added as an internal standard.

Figure 21:
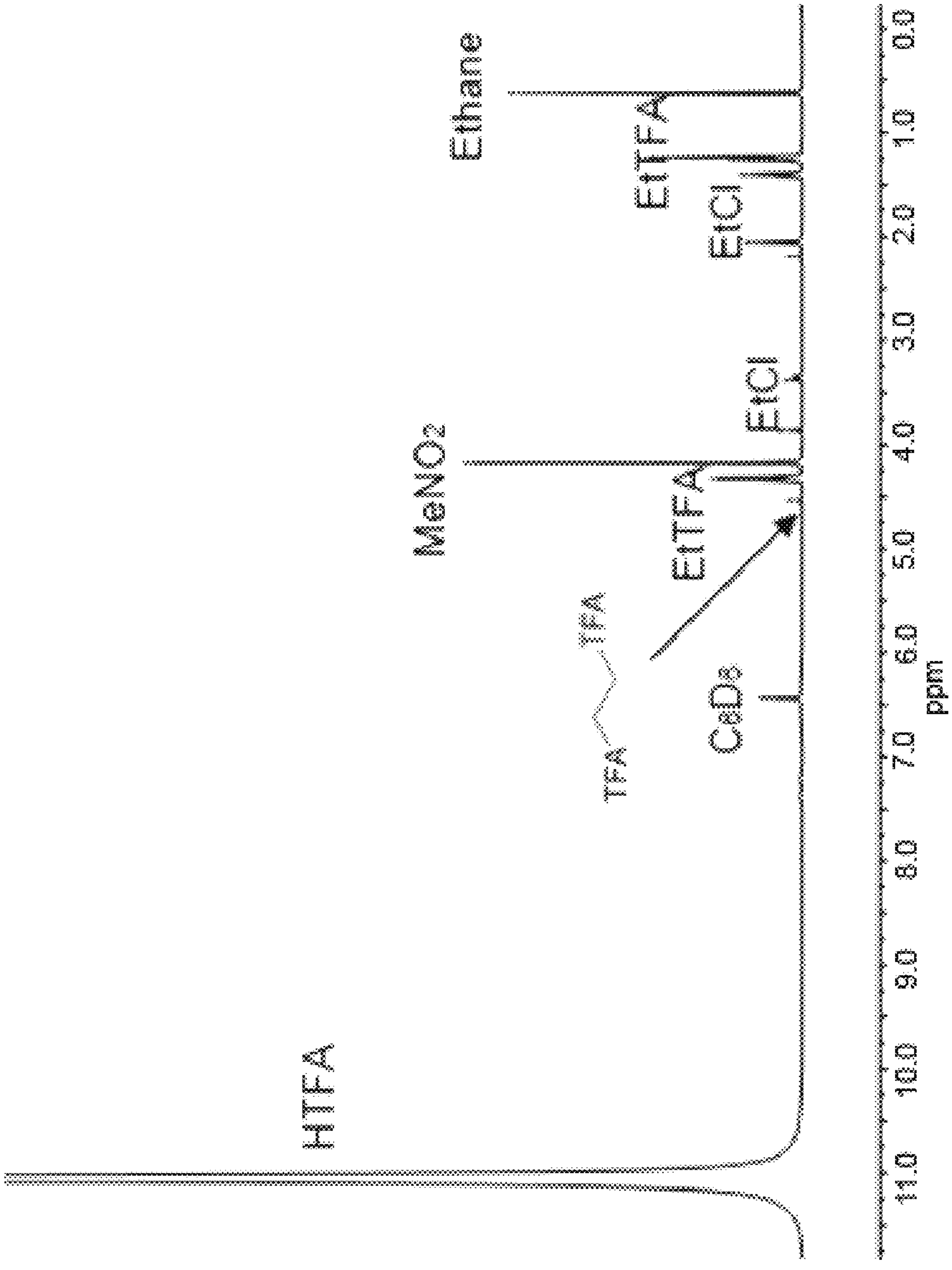

FIG. 21 shows a representative $^1H$ NMR spectrum of ethane functionalization with KCl/$NH_4NO_3$ in HTFA. Conditions: $CH_3CH_3$ (300 psi), KCl (0.1 mmol), $NH_4NO_3$ (1.1 mmol), HTFA (8 mL), 180° C., 2 h. Nitromethane (0.37 mmol) added as an internal standard.

Figure 22:
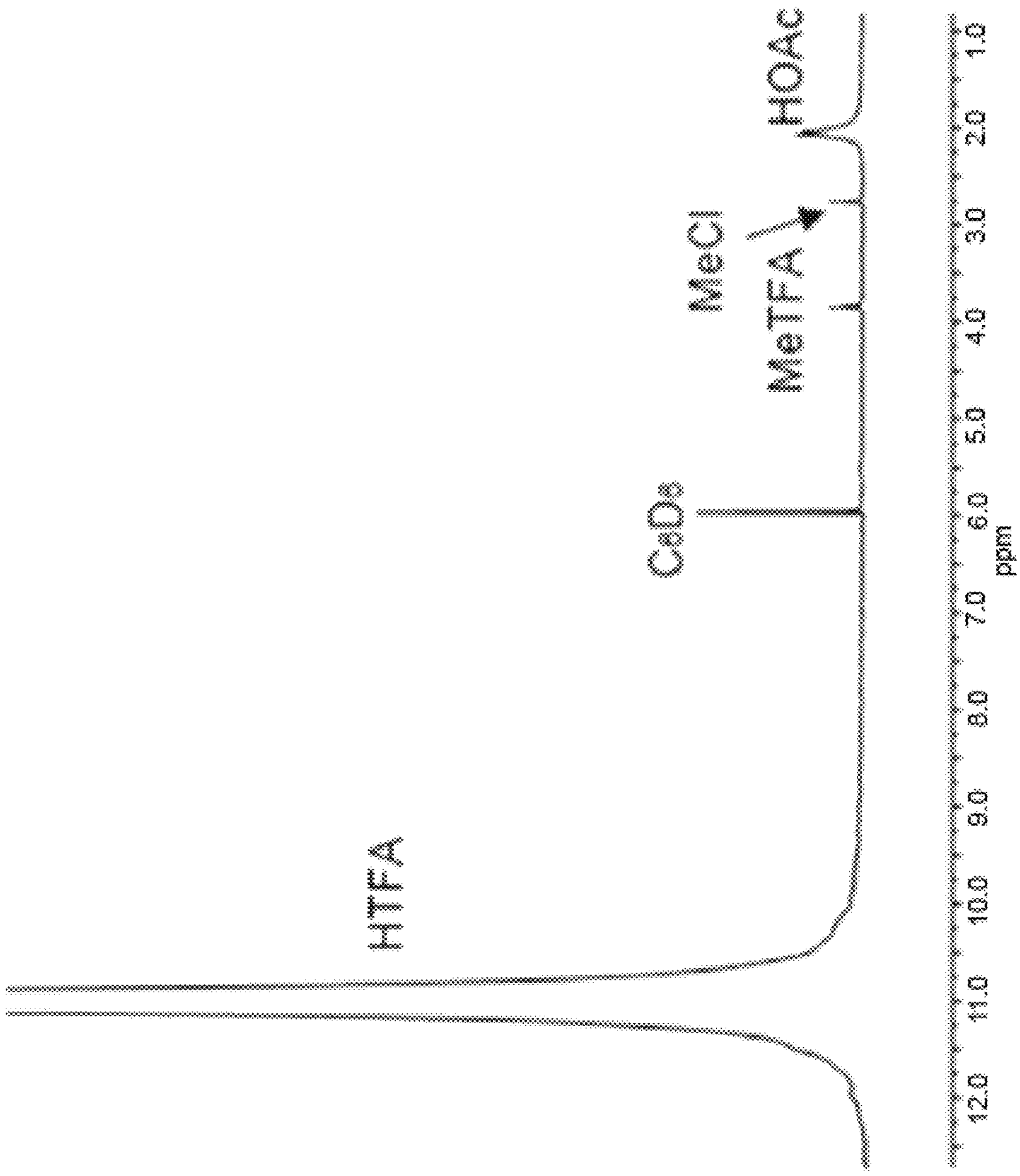

FIG. 22 shows a representative $^1H$ NMR spectrum of methane functionalization with KCl/$NaBiO_3$ in HTFA. Conditions: $CH_4$ (300 psi), KCl (0.1 mmol), $NH_4NO_3$ (1.1 mmol), HTFA (8 mL), 180° C., 1 h. HOAc (0.35 mmol) was added as an internal standard.

Figure 23:
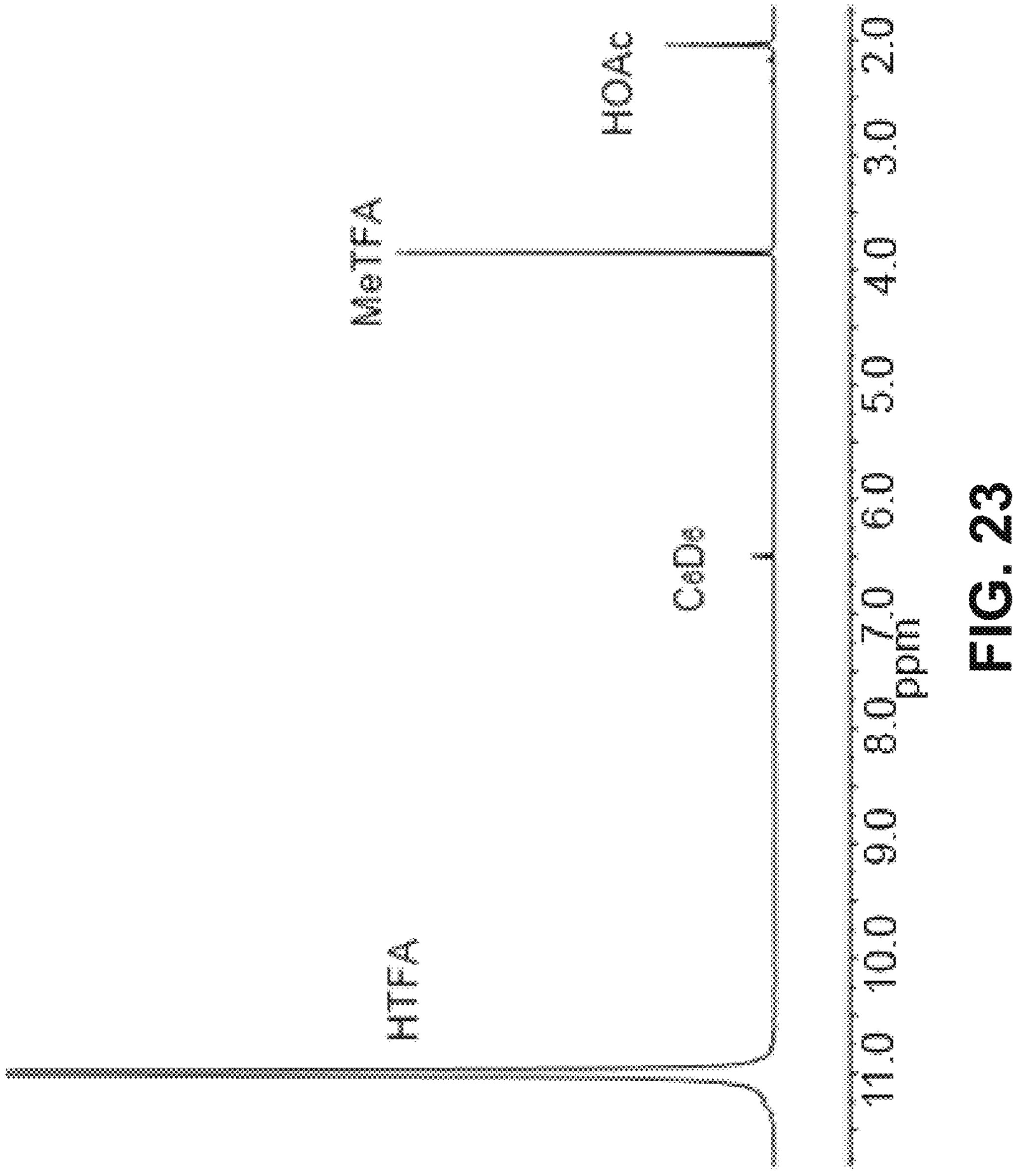

FIG. 23 shows a representative $^1H$ NMR spectrum of MeTFA decay in the presence of $NaBiO_3$. Conditions: argon (300 psi), MeTFA (0.65 mmol), KCl (0.1 mmol), $NH_4NO_3$ (1.1 mmol), HTFA (8 mL), 80° C., 2 h. HOAc (0.35 mmol) was added as an internal standard.

Figure 24:
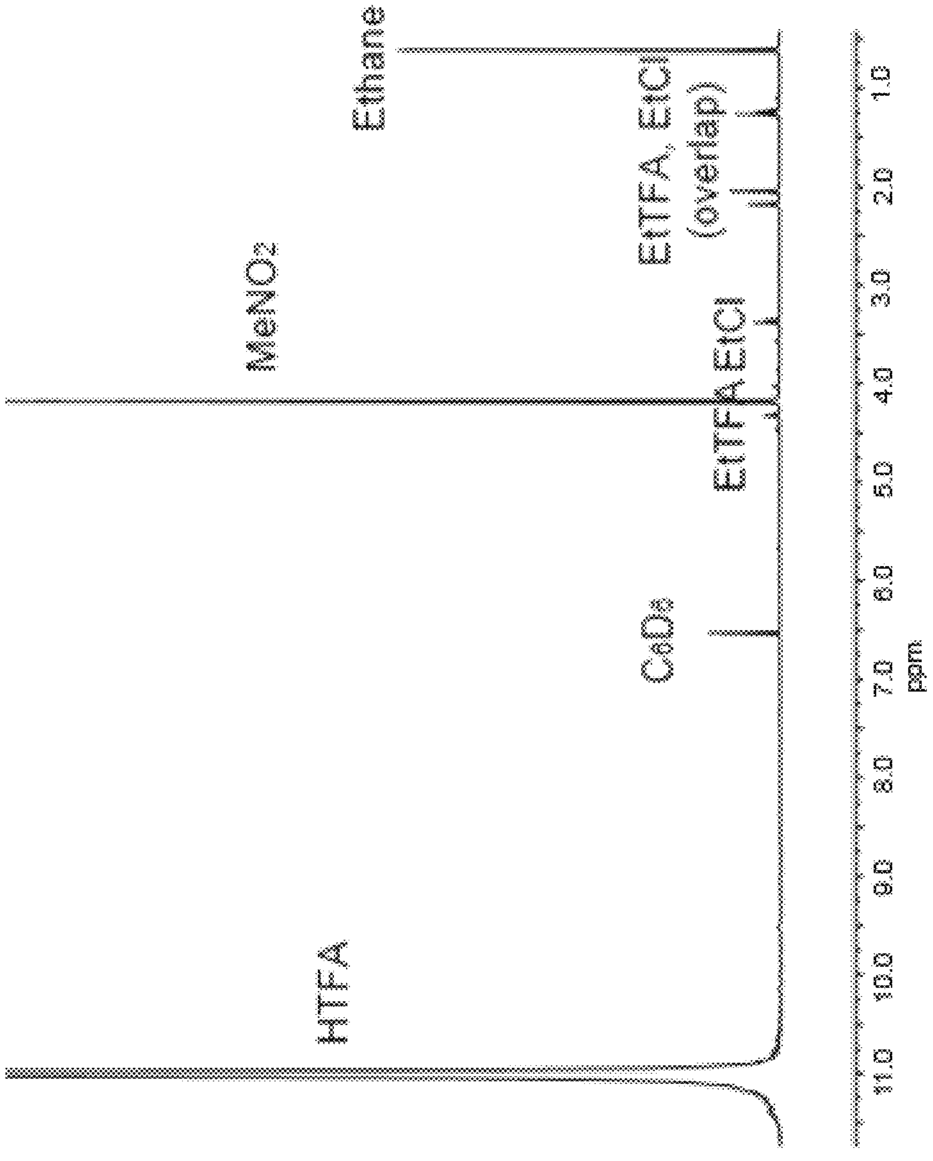

FIG. 24 shows a representative $^1H$ NMR spectrum of ethane functionalization with KCl/$NaBiO_3$ in HTFA. Conditions: $CH_4$ (300 psi), KCl (0.1 mmol), $NaBiO_3$ (1.1 mmol), HTFA (8 mL), 80° C., 2 h. Nitromethane (0.37 mmol) was added as an internal standard.

Figure 25:
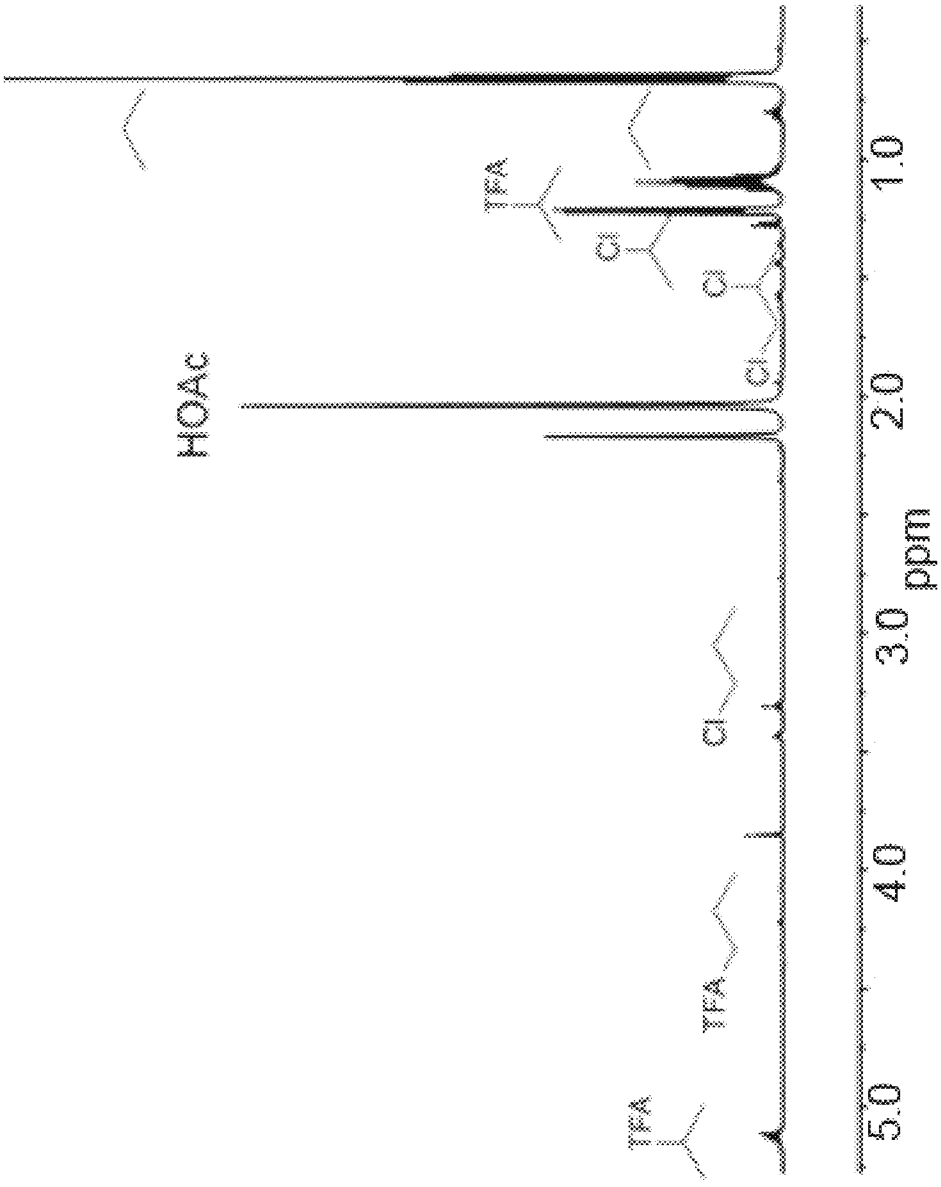

FIG. 25 shows a representative $^1H$ NMR spectrum of propane functionalization with KCl/$NaBiO_3$ in HTFA. Conditions: $CH_4$ (300 psi), KCl (0.1 mmol), $NaBiO_3$ (1.1 mmol), HTFA (8 mL), 80° C., 2 h. HOAc (0.35 mmol) was added as an internal standard.

Figure 26:
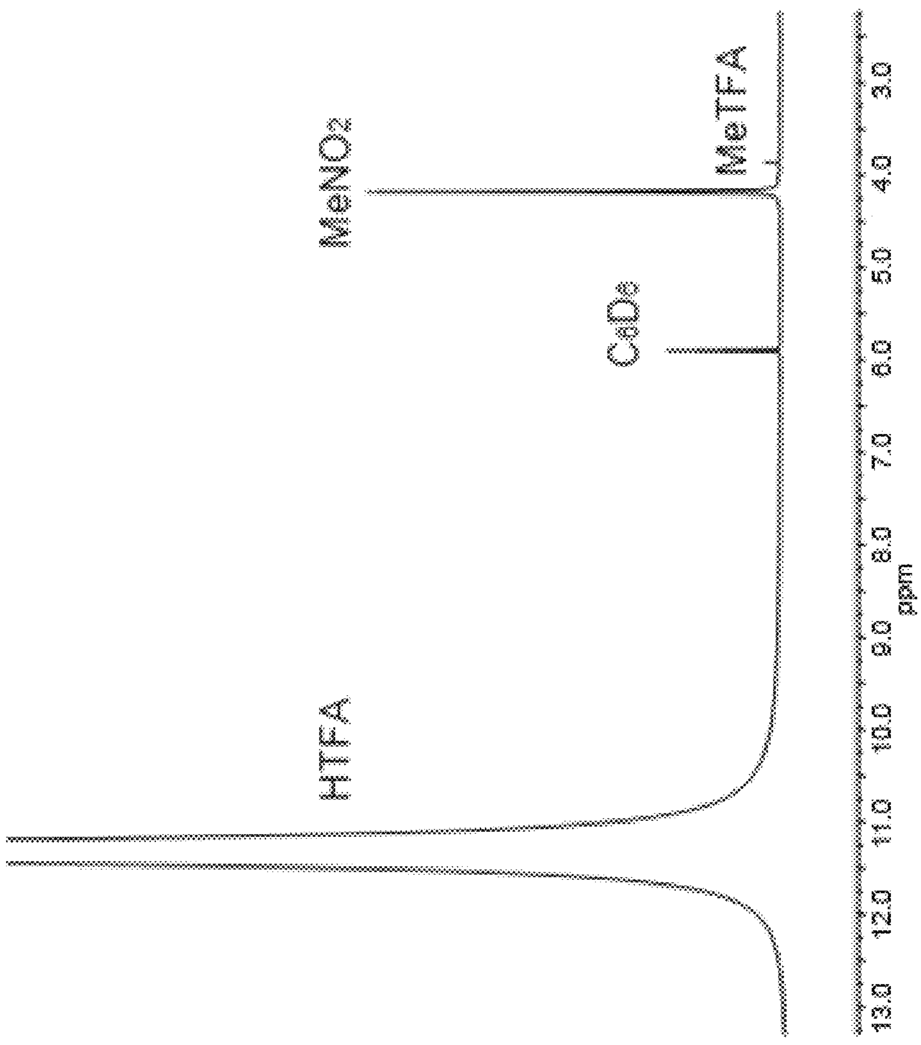

FIG. 26 shows a representative $^{1}H$ NMR spectrum of methane functionalization with $KCl/CeO_2$. Conditions: $CH_4$ (300 psi), KCl (0.1 mmol), $CeO_2$ (1.1 mmol), HTFA (8 mL), 180° C., 1 h. Nitromethane (0.37 mmol) was added as an internal standard.

Figure 27:
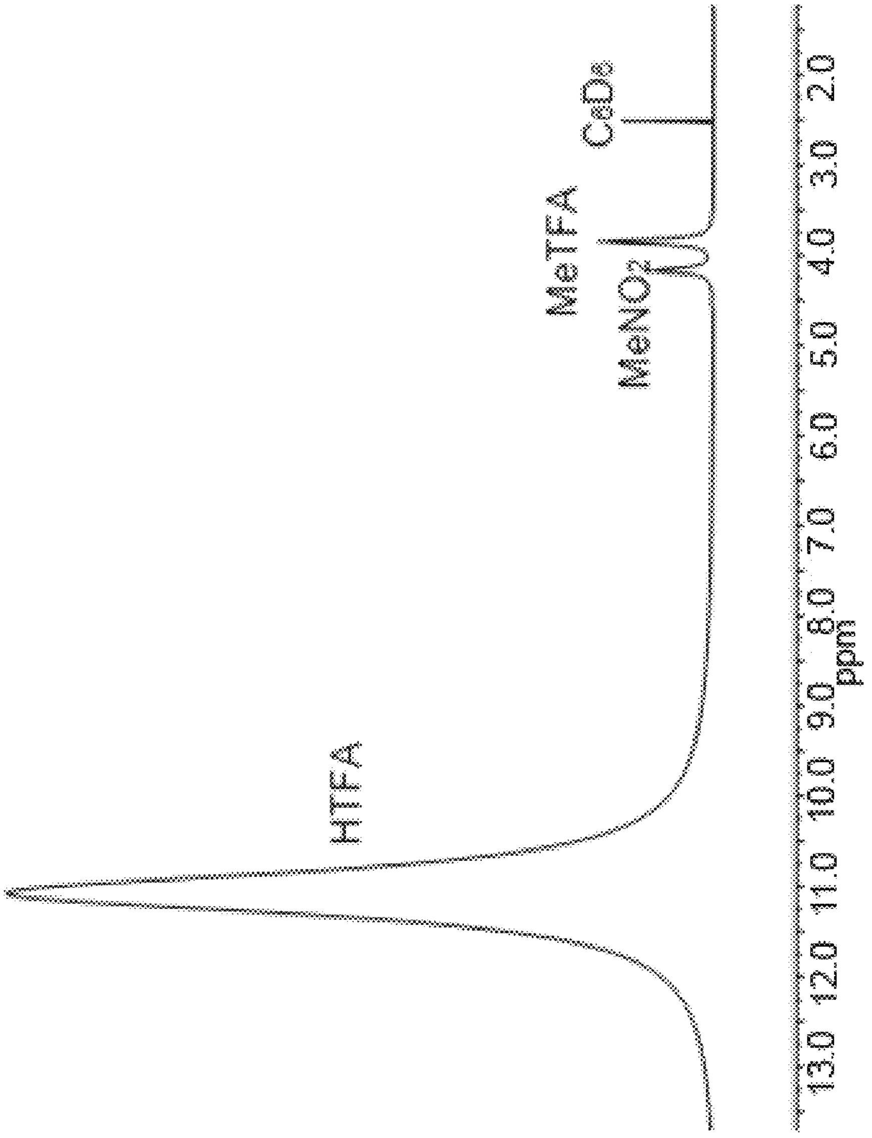

FIG. 27 shows a representative $^{1}H$ NMR spectrum of methane functionalization with $MnO_2/I_2$ in the absence of KCl. Conditions: $CH_4$ (300 psi), $MnO_2$ (1.1 mmol), $I_2$ (0.1 mmol), HTFA (8 mL), 180° C., 1 h. Nitromethane (0.3 mmol) was added as an internal standard.

Figure 28:
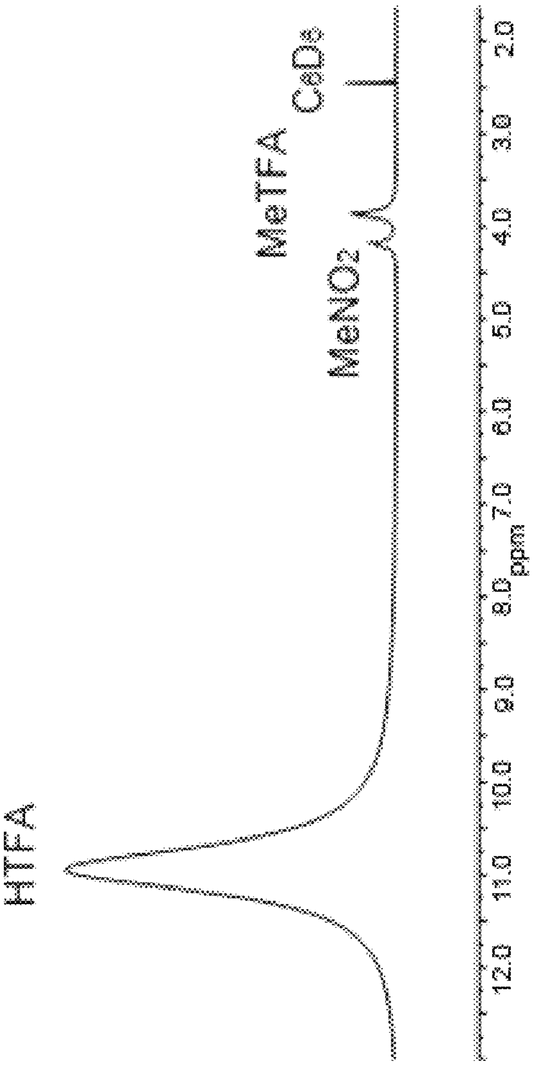

FIG. 28 shows a representative $^{1}H$ NMR spectrum of methane functionalization with $KCl/MnO_2/I_2$. Conditions: $CH_4$ (300 psi), KCl (0.1 mmol), $MnO_2$ (1.1 mmol), $I_2$ (0.1 mmol), HTFA (8 mL), 180° C., 1 h. Nitromethane (0.37 mmol) was added as an internal standard.

Figure 29:
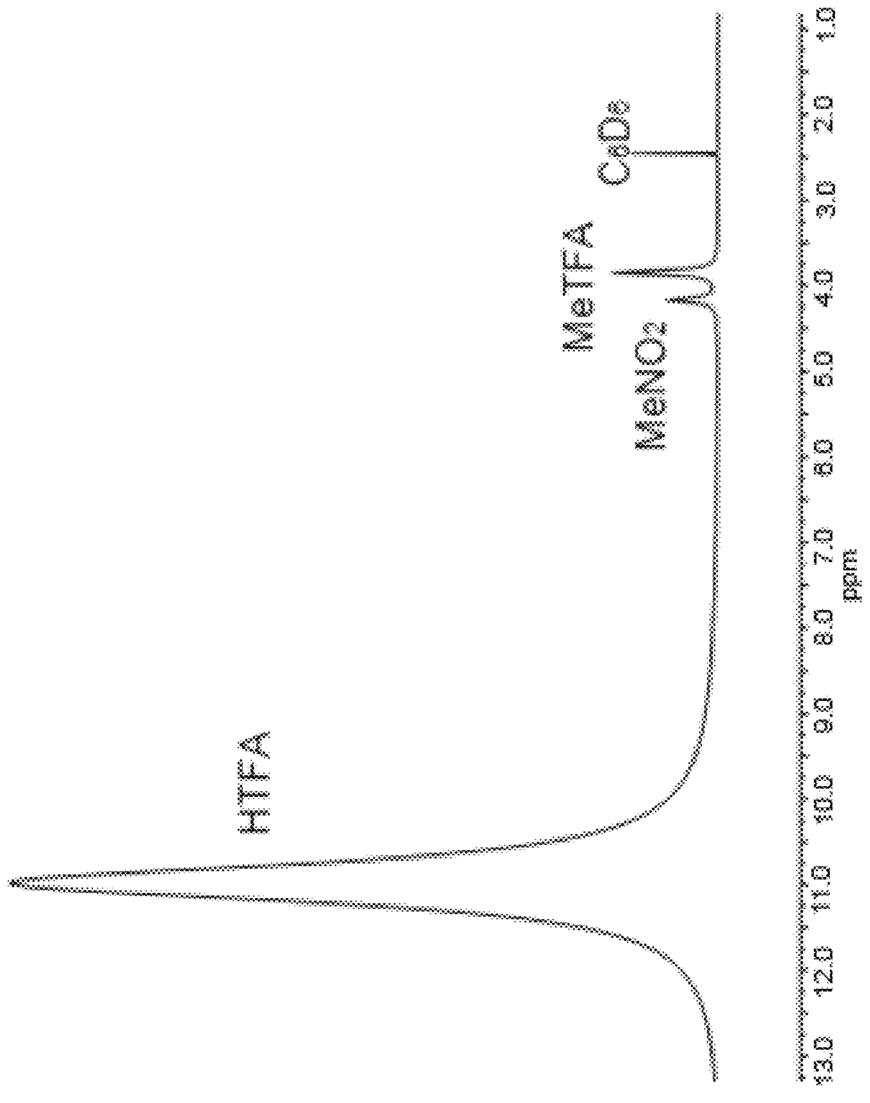

FIG. 29 shows a representative $^{1}H$ NMR spectrum of methane functionalization with $MnO_2/I_2$. Conditions: $CH_4$ (300 psi), $MnO_2$ (1.1 mmol), $I_2$ (0.15 mmol), HTFA (8 mL), 180° C., 1 h. Nitromethane (0.37 mmol) was added as an internal standard.

Figure 30:
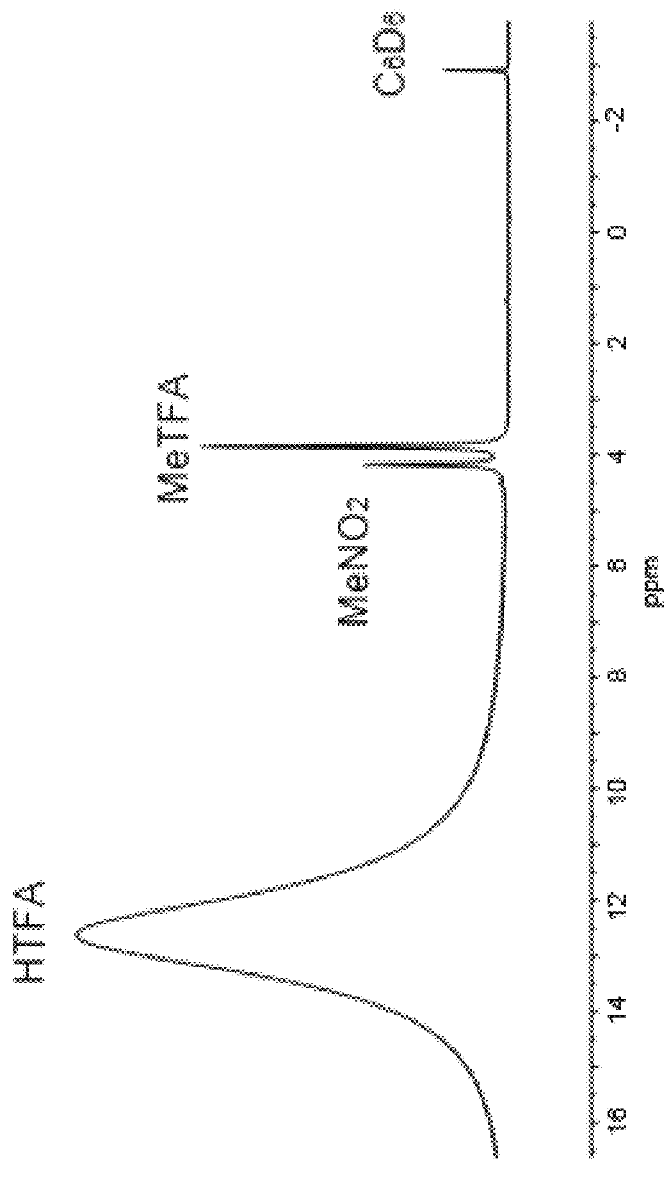

FIG. 30 shows a representative $^{1}H$ NMR spectrum of methane functionalization with $Mn_2O_3/I_2$. Conditions: $CH_4$ (300 psi), $Mn_2O_3$ (1.1 mmol), $I_2$ (0.15 mmol), HTFA (8 mL), 180° C., 1 h. Nitromethane (0.37 mmol) was added as an internal standard.

Figure 31:
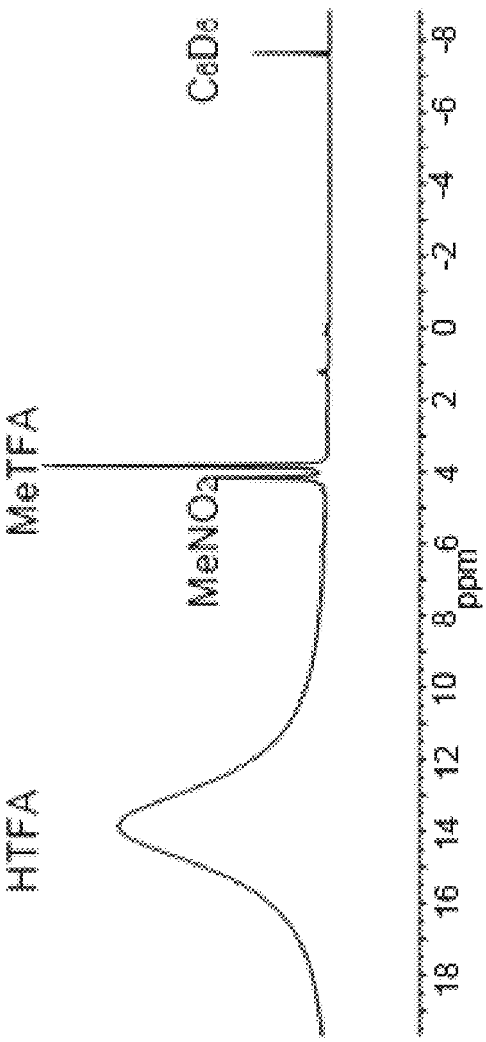

FIG. 31 shows a representative $^{1}H$ NMR spectrum of methane functionalization with $Mn_3O_4/I_2$. Conditions: $CH_4$ (300 psi), $Mn_3O_4$ (1.1 mmol), $I_2$ (0.15 mmol), HTFA (8 mL), 180° C., 1 h. Nitromethane (0.37 mmol) was added as an internal standard.

Figure 32:
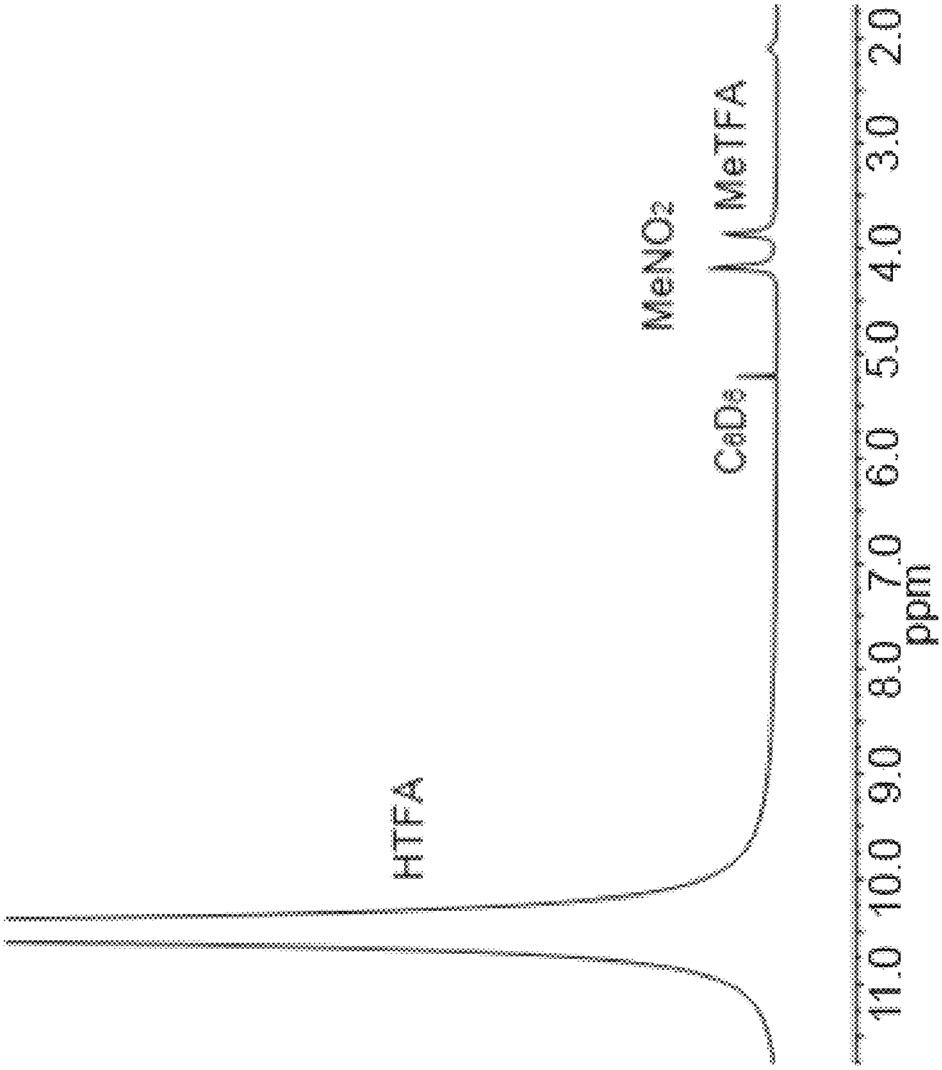

FIG. 32 shows a representative $^{1}H$ NMR spectrum of methane functionalization with $KMnO_4/I_2$. Conditions: $CH_4$ (300 psi), $KMnO_4$ (1.1 mmol), $I_2$ (0.15 mmol), HTFA (8 mL), 180° C., 1 h. Nitromethane (0.37 mmol) was added as an internal standard.

Figure 33:
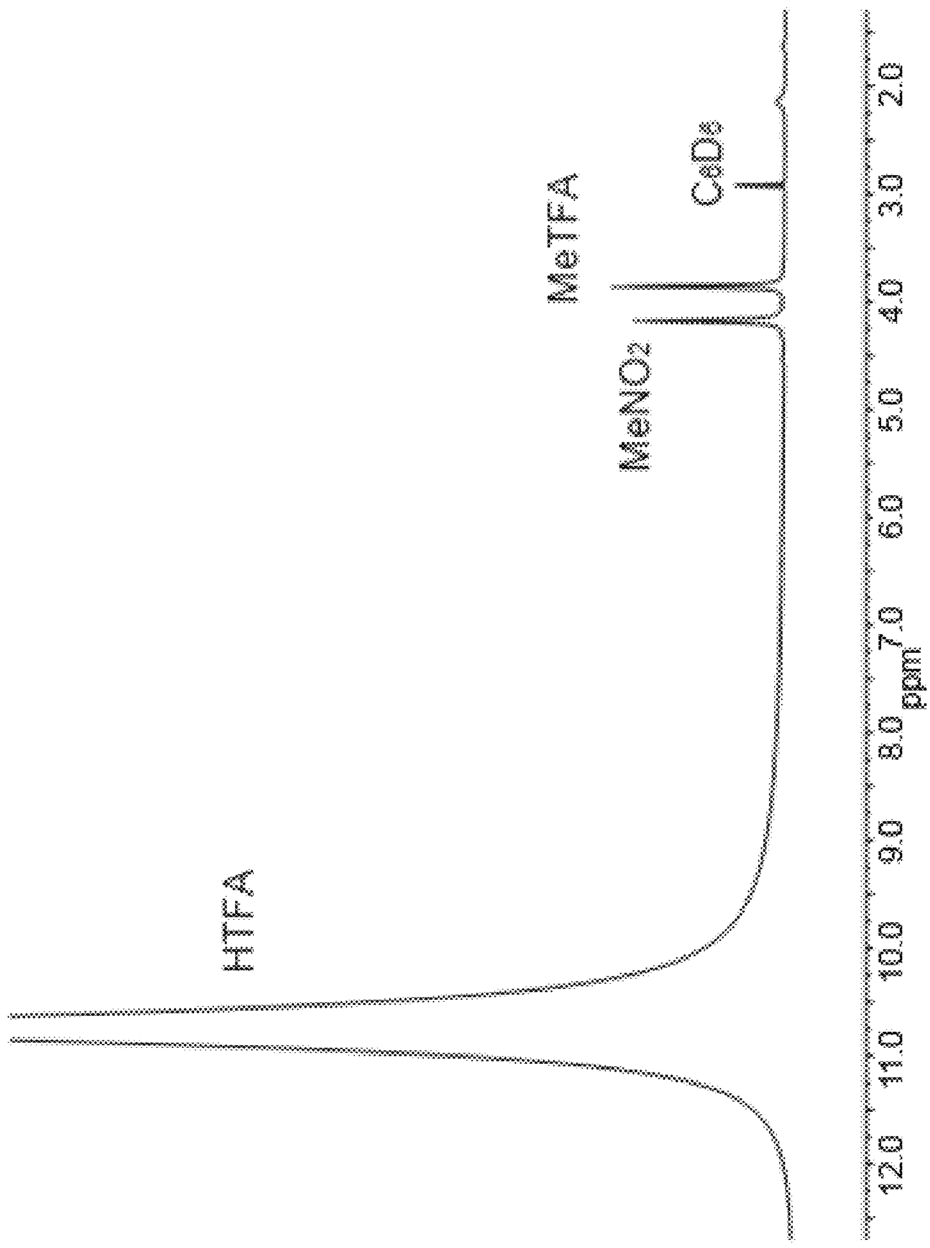

FIG. 33 shows a representative $^{1}H$ NMR spectrum of methane functionalization with $K_2MnO_4/I_2$. Conditions: $CH_4$ (300 psi), $K_2MnO_4$ (1.1 mmol), $I_2$ (0.15 mmol), HTFA (8 mL), 180° C., 1 h. Nitromethane (0.37 mmol) was added as an internal standard.

Figure 34:
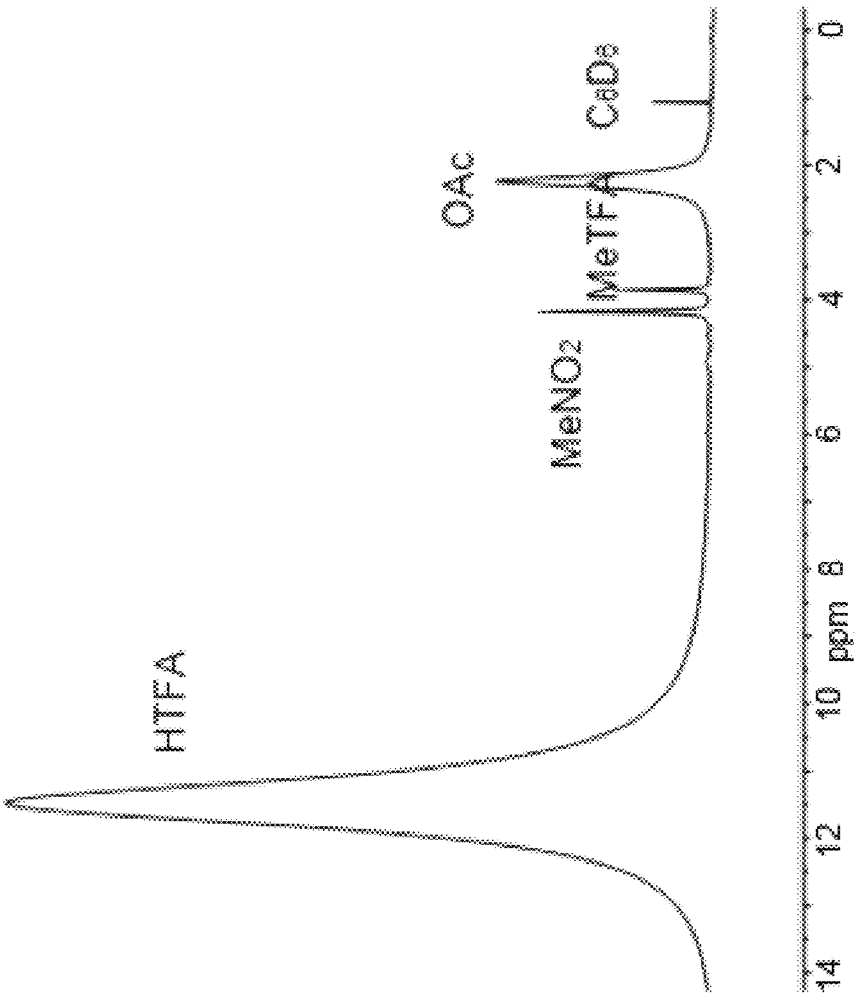

FIG. 34 shows a representative $^{1}H$ NMR spectrum of methane functionalization with $Mn(OAc)_3 \cdot 2H_2O/I_2$. Conditions: $CH_4$ (300 psi), $Mn(OAc)_3 \cdot 2H_2O$ (1.1 mmol), $I_2$ (0.15 mmol), HTFA (8 mL), 180° C., 1 h. Nitromethane (0.37 mmol) was added as an internal standard.

Figure 35:
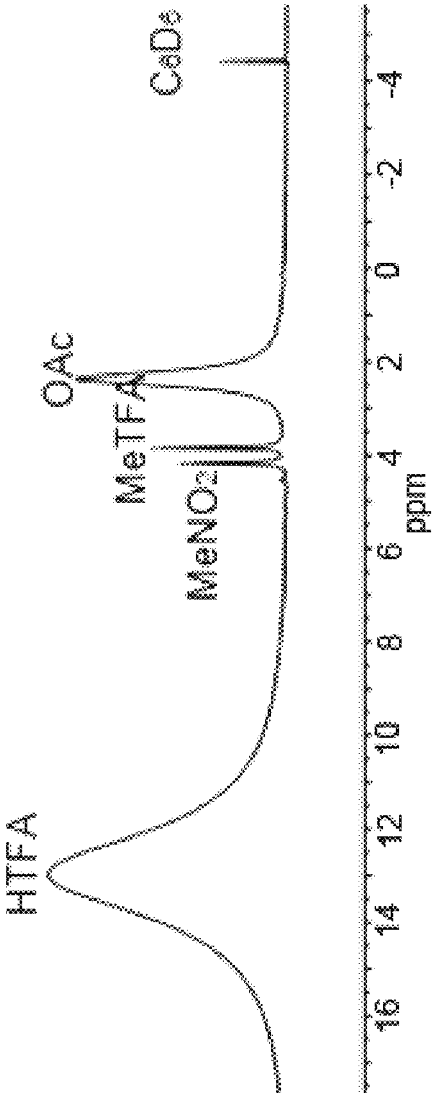

FIG. 35 shows a representative $^{1}H$ NMR spectrum of methane functionalization with $Mn(OAc)_3 \cdot 2H_2O/I_2$. Conditions: $CH_4$ (300 psi), $Mn(OAc)_3 \cdot 2H_2O$ (2.2 mmol), $I_2$ (0.15 mmol), HTFA (8 mL), 180° C., 2 h. Nitromethane (0.37 mmol) was added as an internal standard.

Figure 36:
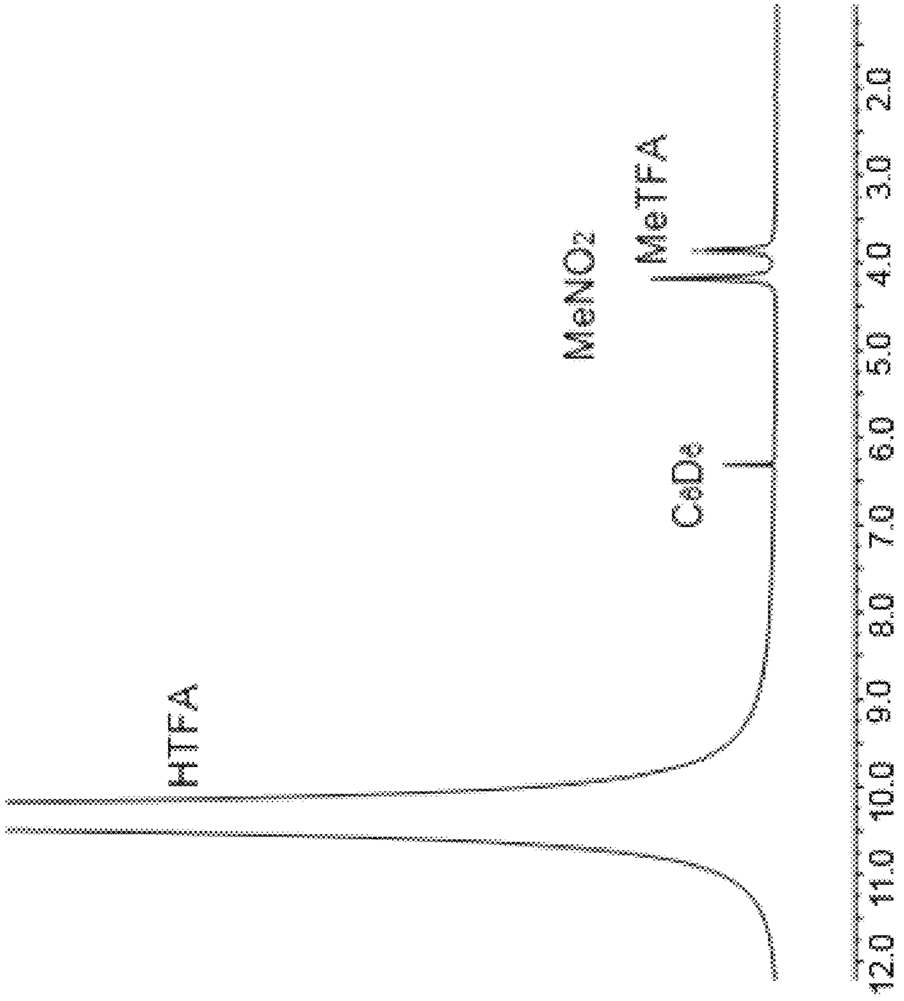

FIG. 36 shows a representative $^{1}H$ NMR spectrum of MeTFA decay in the presence of $MnO_{2/2}$. Conditions: MeTFA (0.63 mmol), Ar (300 psi), $MnO_2$ (1.1 mmol), $I_2$ (0.15 mmol), HTFA (8 mL), 140° C., 2 h. Nitromethane (0.37 mmol) was added as an internal standard.

Figure 37:
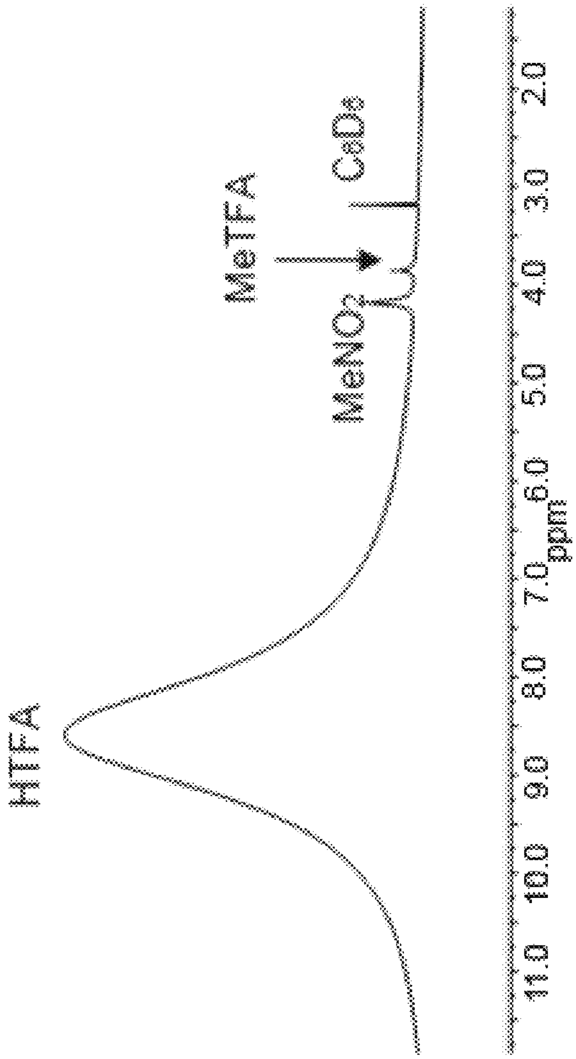

FIG. 37 shows a representative $^{1}H$ NMR spectrum of methane functionalization with $MnO_2/I_2$ in dilute HTFA. Conditions: $CH_4$ (300 psi), $MnO_2$ (1.1 mmol), $I_2$ (0.15 mmol), HTFA/$H_2O$ (7:1 v/v), 180° C., 1 h. Nitromethane (0.37 mmol) was added as an internal standard.

Figure 38:
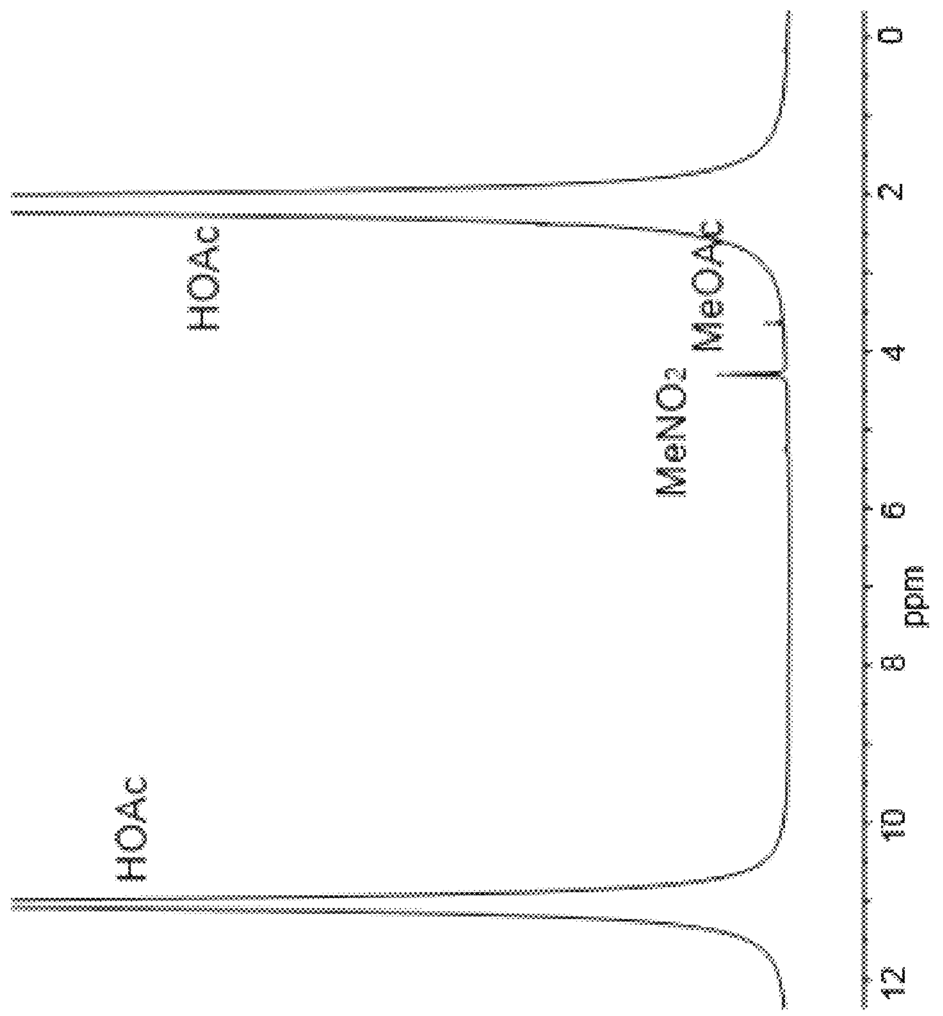

FIG. 38 shows a representative $^{1}H$ NMR spectrum of methane functionalization with $MnO_2/I_2$ in HOAc. Conditions: $CH_4$ (300 psi), $MnO_2$ (1.1 mmol), $I_2$ (0.15 mmol), HOAc (8 mL), 180° C., 1 h. Nitromethane (0.37 mmol) was added as an internal standard.

Figure 39:
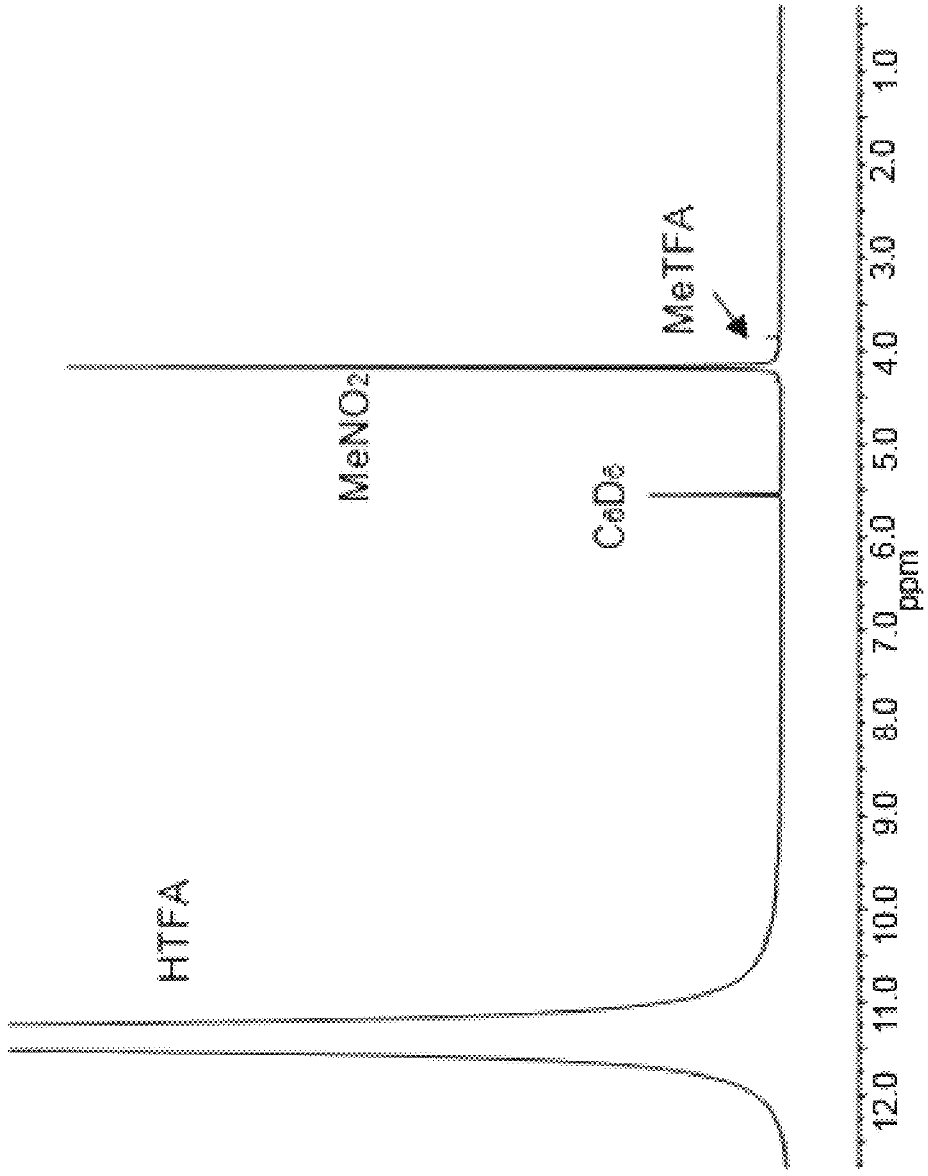

FIG. 39 shows a representative $^{1}H$ NMR spectrum of methane functionalization with $KCl/Fe_2O_3$ in HTFA. Conditions: $CH_4$ (300 psi), KCl (0.1 mmol), $Fe_2O_3$ (1.1 mmol), HTFA (8 mL), 180° C., 1 h. Nitromethane (0.37 mmol) was added as an internal standard.

Figure 40:
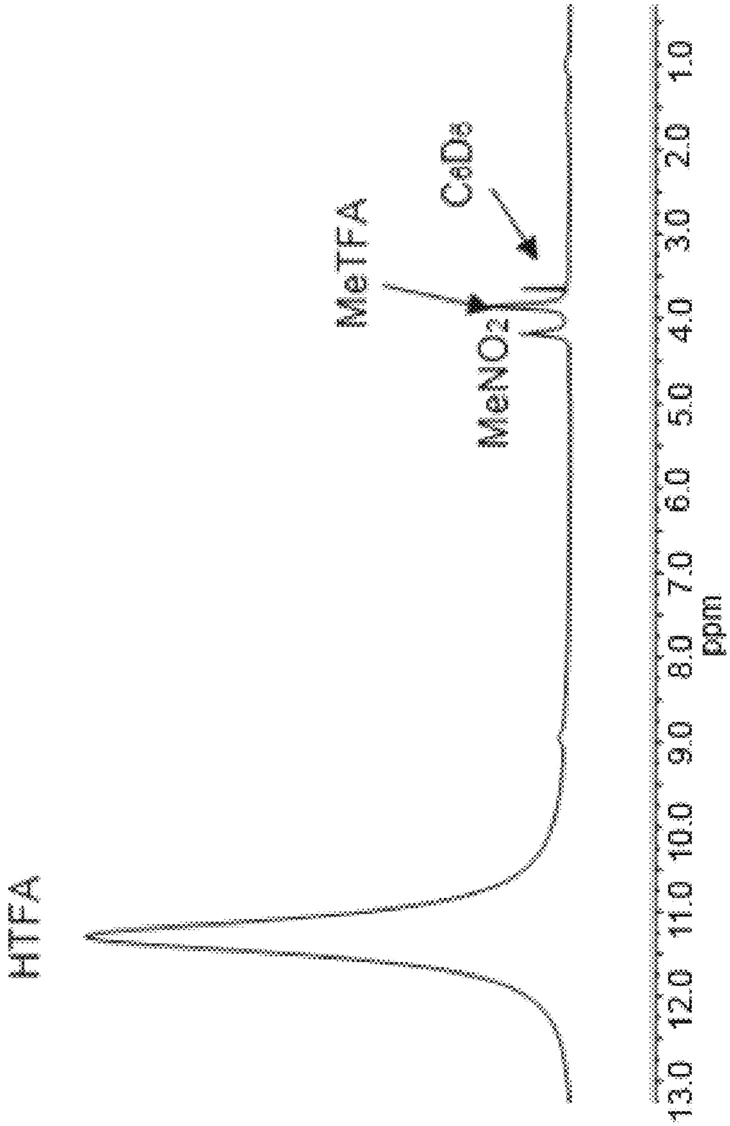

FIG. 40 shows a representative $^{1}H$ NMR spectrum of methane functionalization with KCl/Fe-BTC in HTFA. Conditions: $CH_4$ (300 psi), KCl (0.1 mmol), Fe-BTC (1.1 mmol), HTFA (8 mL), 180° C., 1 h. Nitromethane (0.37 mmol) was added as an internal standard.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of.

As used in the specification and the appended claims, the singular forms "a," "an" and "the" include plural referents unless the context clearly dictates otherwise. Thus, for example, reference to "an iodine-based compound," "an oxidant," or "an acid," includes, but is not limited to, combinations of two or more such iodine-based compounds, oxidants, or acids, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the term "effective amount" refers to an amount that is sufficient to achieve the desired modification of a physical property of the composition or material. For example, an "effective amount" of an oxidant refers to an amount that is sufficient to achieve the desired improvement in the property modulated by the formulation component, e.g. achieving the desired level of hydrocarbon functionalization. The specific level in terms of wt % in a composition required as an effective amount will depend upon a variety of factors including the amount and type of hydrocarbon to be functionalized, amount and type of iodine-based compound, if present, amount and type of compound having the formula $A_aX_n$, if present, and temperature of the reaction vessel.

As used herein, the terms "optional" or "optionally" means that the subsequently described event or circumstance can or cannot occur, and that the description includes instances where said event or circumstance occurs and instances where it does not.

As used herein the terms "weight percent," "wt %," and "wt. %," which can be used interchangeably, indicate the percent by weight of a given component based on the total weight of the composition, unless otherwise specified. That is, unless otherwise specified, all wt % values are based on the total weight of the composition. It should be understood that the sum of wt % values for all components in a disclosed composition or formulation are equal to 100.

References in the specification and concluding claims to parts by weight of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

The term "hydroxyl" or "hydroxy" as used herein is represented by the formula-OH.

The term "alkoxy" as used herein is represented by the formula-OR, where R is an unsubstituted or substituted alkyl group as defined herein.

The term "carboxylic acid" as used herein is represented by the formula —C(O)OH.

The term "ester" as used herein is represented by the formula —OC(O)R, where R is an unsubstituted or substituted alkyl group as defined herein.

The term "ether" as used herein is represented by the formula -$A^1OA^2$, where $A^1$ and $A^2$ are each an unsubstituted or substituted alkyl group as defined herein.

The terms "halo," "halogen" or "halide," as used herein can be used interchangeably and refer to F, Cl, Br, or I.

As used herein, "functionalized" refers to the replacement of one or more hydrogen atoms in the hydrocarbon with a functional group. In one aspect, the functional group is a hydroxyl group, alkoxy group, ester group, or ether group. In another aspect, the functional group is a halide group. In some aspects, the hydrocarbons can be "monofunctionalized," where a single hydrogen in the hydrocarbon is replaced with a functional group. (e.g., the formation of methanol from methane or of ethanol from ethane). In other aspects, the methods described herein can produce a mixture of monofunctionalized hydrocarbons (e.g., MeOH and MeCl).

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

Unless otherwise specified, temperatures referred to herein are based on atmospheric pressure (i.e. one atmosphere).

Methods for Producing Functionalized Hydrocarbons

In one aspect, disclosed herein is a method for producing a functionalized hydrocarbon. In a further aspect, the method includes the steps of mixing a hydrocarbon with a composition, wherein the composition includes an acid and an oxidant. The methods described herein are advantageous because they inexpensive catalysts I.e., oxidants) and they can be adapted to provide selectively monofunctionalized products. The methods described herein also use weaker acids than methods currently employed (and avoids the use of superacids). Finally, the methods described herein are fast and can operate at lower temperatures than current processes. Provided below are the components and conditions for performing the methods described herein.

Acids

In one aspect, the acid can be trifluoroacetic acid, triflic acid, trifluoromethyl phosphonic acid, hexafluorobutyric acid, sulfuric acid, acetic acid, methanesulfonic acid, phosphoric acid, or any combination thereof.

In one aspect, the acid can be trifluoroacetic acid (HTFA). In another aspect, the acid can be used as a solvent. Further in this aspect, the acid is present in an excess amount compared to the other components of the composition and/or the hydrocarbon. Still further in this aspect, the components of the composition and/or the hydrocarbon are soluble in the acid.

In any of these aspects, the composition can be substantially free of superacid. In one aspect, the acid can be used neat (i.e., not mixed with a co-solvent). In other aspects, the acid can be mixed with water or an organic solvent.

Oxidants

In one aspect, the oxidant comprises a manganese compound, a lead compound, a cerium compound, an iron compound, a bismuth compound, a copper compound, a nitrate, or any combination thereof.

In one aspect, the manganese compound comprises a $Mn^{II}$ compound, a $Mn^{III}$ compound, a $Mn^{IV}$ compound, or any combination thereof. In one aspect, the $Mn^{II}$ compound can be $Mn_2(TFA)_4(HTFA)_4$. In another aspect, the $Mn^{III}$ compound can be $Mn(TFA)_3$. In still another aspect, the $Mn^{IV}$ compound can be $MnO_2$.

In one aspect, the lead compound comprises a $Pb^{IV}$ compound. In another aspect, the $Pb^{IV}$ compound can be $PbO_2$, $Pb(TFA)_4$, or a combination thereof.

In one aspect, the cerium compound comprises a $Ce^{IV}$ compound. In another aspect, the $Ce^{IV}$ compound can be $CeO_2$.

In one aspect, the iron compound comprises a $Fe^{III}$ compound. In another aspect, the $Fe^{III}$ compound can be $Fe_2O_3$, iron 1,3,5-benzenetricarboxylate (Fe-BTC), or a combination thereof.

In one aspect, the bismuth compound comprises a $Bi^{V}$ compound. In another aspect, the bismuth oxide compound can be represented by the formula $YBiO_3$, wherein Y can be selected from hydrogen, lithium, sodium, potassium, ammonium ($NH_4^+$), alkylammonium, phosphonium ($PH_4^+$), alkylphosphonium, arylphosphonium, trimethyl sulfonium ($[S(CH_3)_3]^+$), or a combination thereof.

In one aspect, the copper compound comprises a $Cu^{II}$ compound. In another aspect, the $Cu^{II}$ compound can be copper 1,3,5-benzenetricarboxylate (Cu-BTC).

In another aspect, the nitrate can be represented by the formula $ZNO_3$, wherein Z can be selected from hydrogen, lithium, sodium, potassium, ammonium ($NH_4^+$), alkylammonium, phosphonium ($PH_4^+$), alkylphosphonium, arylphosphonium, trimethyl sulfonium ($[S(CH_3)_3]^+$), or a combination thereof.

Iodine-Based Compounds

In one aspect, in the method disclosed herein, the compositions for functionalizing hydrocarbons can further include iodine, an iodine-based compound, or a combination thereof. In a further aspect, the iodine-based compound can include iodate, periodate, iodine oxide, iodosyl ($IO^+$), a trivalent iodine compound, or any combination thereof.

In a further aspect, the iodine-based compound can be represented by the formula $Q(IO_3)_p$, wherein Q can be selected from hydrogen, lithium, sodium, potassium, beryllium, magnesium, calcium, strontium, barium, a transition metal, aluminum, gallium, thallium, indium, tin, sulfur, ammonium ($NH_4^+$), alkylammonium, phosphonium ($PH_4^+$), alkylphosphonium, arylphosphonium, trimethyl sulfonium ($[S(CH_3)_3]^+$), or a combination thereof, and wherein p can be from 1 to 5. In some aspects, p is 1, 2, 3, 4, or 5.

In still another aspect, the iodine-based compound can be selected from: $KIO_3$, $Ca(IO_3)_2$, $Ba(IO_3)_2$, $Cu(IO_3)_2$, $NH_4IO_3$, $H_5IO_6$, $KIO_4$, $NaIO_4$, $NH_4IO_4$, $I(TFA)_3$, $I_2O_5$, $[IO]^+$, $[IO_2]^+$, or any combination thereof.

In one aspect, the molar ratio of oxidant to iodine or iodine-based compound, when present, is from about 1:1 to about 30:1, or is about 1:1, 2:1, 3:1, 4:1, 5:1, 6:1, 7:1, 8:1, 9:1, 10:1, 15:1, 20:1, 25:1, or 30:1, or a combination of any of the foregoing values, or a range encompassing any of the foregoing values.

Compounds Having Formula $A_aX_n$

In one aspect, in the method disclosed herein, the composition for functionalizing hydrocarbons can also include a compound having formula $A_aX_n$. Further in this aspect, A can be hydrogen, lithium, sodium, potassium, beryllium, magnesium, calcium, strontium, barium, a transition metal, aluminum, gallium, thallium, indium, tin, sulfur, ammonium ($NH_4^+$), alkylammonium, phosphonium ($PH_4^+$), alkylphosphonium, arylphosphonium, trimethyl sulfonium ($[S(CH_3)_3]^+$), or a combination thereof. In a further aspect, X can be chlorine. In still another aspect, subscript "a" represents an oxidation state of X and subscript "n" represents an oxidation state of A.

In one aspect, the compound having formula $A_aX_n$ can be HCl, NaCl, KCl, $CaCl_2$), LiCl, $ZnCl_2$, $BeCl_2$, $MgCl_2$, $PCl_3$, $NH_4Cl$, $CCl_4$, $CHCl_3$, a transition metal chloride, a main group metal chloride, an organochloride, or any combination thereof.

In one aspect, the molar ratio of oxidant to compound having formula $A_aX_n$ is from about 1:1 to about 30:1, or is about 1:1, 2:1, 3:1, 4:1, 5:1, 6:1, 7:1, 8:1, 9:1, 10:1, 15:1, 20:1, 25:1, or 30:1, or a combination of any of the foregoing values, or a range encompassing any of the foregoing values.

In any of these aspects, the compound having formula $A_aX_n$ can act as a catalyst.

Hydrocarbon

The term "hydrocarbon" as used herein includes any saturated organic molecule consisting only of carbon and hydrogen. In one aspect, the hydrocarbon used herein can be any linear or branched alkane having from 1 to 24 carbon atoms including, but not limited to, methane, ethane, propane, butane, pentane, hexane, heptane, or octane. In another aspect, the hydrocarbon is an unsubstituted cycloalkane having from 3 to 20 carbon atoms such as, cyclopentane, cyclohexane, cycloheptane, cyclooctane, adamantane, and related compounds. In one aspect, the cycloalkane can be substituted with one or more alkyl groups as defined herein.

In one aspect, the hydrocarbon used herein can be provided in the form of a gas such as, for example, methane, ethane, or propane. In a further aspect, when the hydrocarbon is provided in the form of a gas, it is added to a reaction vessel at a pressure of from 50 to 500 psi, or from 100 to 300 psi, or at about 50, 100, 150, 200, 250, 300, 350, 400, 450, or about 500 psi, or a combination of any of the foregoing values, or a range encompassing any of the foregoing values. In one aspect, the hydrocarbon is methane at a pressure of 300 psi. In another aspect, the hydrocarbon is propane at a pressure of 100 psi.

In one aspect, in the method disclosed herein, the hydrocarbon can be monofunctionalized during performance of the method. In another aspect, the hydrocarbon can be a linear or branched alkane, a substituted or unsubstituted cycloalkane, or a combination thereof.

In a further aspect, conversion of a hydrocarbon to a functionalized hydrocarbon can produce a yield of greater than 50%, 60%, 70%, 80%, 90%, 95%, or 99%. In one aspect, in the process disclosed herein, hydrocarbon conversion is essentially complete.

In yet another aspect, the functionalized hydrocarbon can be methyl trifluoroacetate ester, methyl acetate, methanol, chloromethane, iodomethane, dimethylcarbonate, 1,2-dichloroethane, 1,2-diiodoethane, 1,2-dichloropropane, 1,3-dichloropropane, 1,2-iodopropane, 1,3-diiodopropane ethyl trifluoroacetate ester, ethyl acetate, ethanol, ethyl chloride, ethyl iodide, ethylene glycol, ethylene esters, propyl trifluoroacetate ester, propyl acetate, propanol, propyl chloride, propyl iodide, propylene glycol, propylene esters, or a combination thereof. In some aspects, when the functionalized product incorporates a group that is not a hydroxyl group, the functionalized product can be hydrolyzed to produce a free alcohol and regenerate the functionalization source.

Reaction Conditions

In one aspect, in the method disclosed herein, the composition and hydrocarbon can be mixed and heated at a temperature of from about 100° C. to about 300° C., or at about 100, 120, 140, 160, 180, 200, 220, 240, 260, 280, or about 300° C., or a combination of any of the foregoing values, or a range encompassing any of the foregoing values. In one aspect, the composition and hydrocarbon are heated at about 180° C.

In one aspect, the reactions disclosed herein are carried out for from about 30 minutes to about 12 hours, or for about 0.5, 1, 1.5, 2, 2.5, 3, 4, 5, 6, 7, 8, 9, 10, 11, or about 12 hours, or a combination of any of the foregoing values, or a range encompassing any of the foregoing values.

In any of the above aspects, the various reactants can be added to the reaction vessel in any order, such as, for example, simultaneously, sequentially, or in batches of several components at a time.

In one aspect, the acid, oxidant, and other optional components can be added (e.g., separately, mixed prior to introduction and then added, or simultaneously added) to a reaction vessel to form a first mixture and then the hydrocarbon can be added to the reaction vessel. In one aspect, the reaction vessel can be pressurized with a gas sufficient to provide an internal pressure of about 103 kPa (15 psi) to 10343 kPa (1500 psi) or about 240 kPa (35 psi) to 5516 kPa (800 psi) using a pressure system. In an embodiment, the gas used to obtain this pressure are methane, ethane, propane, butane, carbon dioxide, nitrogen, helium, argon, neon, carbon monoxide, hydrogen, oxygen, air, the hydrocarbon itself, or mixtures thereof. In an embodiment, the pressure system can include pumps, valves, metering gauges, computer system, and the like to accomplish flowing gas into and out of the vessel.

In one aspect, the reaction vessel can be heated to a temperature of about 100° C. to about 300° C., or at about 100, 120, 140, 160, 180, 200, 220, 240, 260, 280, or about 300° C., or a combination of any of the foregoing values, or a range encompassing any of the foregoing values using a temperature system. In one aspect, the temperature system can include heating elements and a computer system to control the heat within the vessel. The temperature can be maintained over a period of about 10 minutes to 5 days or 20 minutes to 5 hours in order to contact the hydrocarbon with the oxidant, acid, and optional components to generate a mixture including the functionalized. The reaction vessel can include a system to mix the contents within the vessel.

Separation and Purification

In one aspect, following completion of the method disclosed herein, the functionalized hydrocarbon can be separated from the oxidant and/or other components present in the composition. In a further aspect, this can be accomplished by known means including, but not limited to, distillation, evaporation, extraction, adsorption, diffusion through a membrane, and combinations thereof. In some aspects, further purification can be performed to achieve a desired or necessary level of purity for the functionalized hydrocarbon for any intended or anticipated further uses.

In another aspect, the oxidant can be immobilized in the reaction vessel used herein, e.g. on a solid surface or a macroscopic particle, thereby allowing separation of the functionalized hydrocarbon by means such as, for example, decantation or filtration.

Oxidant Regeneration

In one aspect, the method disclosed herein involves regeneration of the oxidant, such that the oxidant can be re-used in another cycle of the method disclosed herein. In a further aspect, the oxidant can be regenerated in situ when used in catalytic amounts. In an alternative aspect, the reaction can be performed according to the method disclosed herein with the oxidant in a stoichiometric amount, followed by a second step wherein the oxidant is regenerated. In either of these aspects, the oxidant can be regenerated by an oxidizing regeneration reagent such as, for example, hydrogen peroxide, molecular oxygen, nitric acid, a halogen, air, or a combination thereof. In an alternative aspect, a voltage can be applied to spent (i.e., reduced) oxidant to regenerate the oxidizing capacity of the oxidant. In any of the above aspects, regeneration of the oxidant can take place in the same reactor or in a different reactor (e.g., a parallel reactor) from the reactor in which the disclosed method takes place. In any of these aspects, the process can be conducted in a batch mode or a continuous mode.

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

Exemplary Aspects

Aspect 1: A method comprising mixing a hydrocarbon with a composition comprising an acid and an oxidant comprising a manganese compound, a lead compound, a cerium compound, an iron compound, a bismuth compound, a copper compound, a nitrate, or any combination thereof to produce a functionalized hydrocarbon.

Aspect 2: The aspect of claim 1, wherein the manganese compound comprises a $Mn^{II}$ compound, a $Mn^{III}$ compound, a $Mn^{IV}$ compound, or any combination thereof.

Aspect 3: The aspect of claim 1, wherein the manganese compound comprises $Mn_2(TFA)_4(HTFA)_4$.

Aspect 4: The aspect of claim 1, wherein the manganese compound comprises $Mn(TFA)_3$.

Aspect 5: The aspect of claim 1, wherein the manganese compound comprises $MnO_2$.

Aspect 6: The aspect of claim 1, wherein the lead compound comprises a $Pb^{IV}$ compound.

Aspect 7: The aspect of claim 1, wherein the lead compound comprises $PbO_2$, $Pb(TFA)_4$, or a combination thereof.

Aspect 8: The aspect of claim 1, wherein the cerium compound comprises a $Ce^{IV}$ compound.

Aspect 9: The aspect of claim 1, wherein the cerium compound comprises $CeO_2$.

Aspect 10: The aspect of claim 1, wherein the iron compound comprises a FeII compound.

Aspect 11: The aspect of claim 1, wherein the iron compound comprises $Fe_2O_3$, iron 1,3,5-benzenetricarboxylate (Fe-BTC), or a combination thereof.

Aspect 12: The aspect of claim 1, wherein the bismuth compound comprises a $Bi^{V}$ compound.

Aspect 13: The aspect of claim 1, wherein the bismuth compound is $YBiO_3$, wherein Y is hydrogen, lithium, sodium, potassium, ammonium ($NH_4^+$), alkylammonium, phosphonium ($PH_4^+$), alkylphosphonium, arylphosphonium, or trimethyl sulfonium ($[S(CH_3)_3]^+$).

Aspect 14: The aspect of claim 1, wherein the copper compound comprises a $Cu^{II}$ compound.

Aspect 15: The aspect of claim 1, wherein the copper compound comprises copper 1,3,5-benzenetricarboxylate (Cu-BTC).

Aspect 16: The aspect of claim 1, wherein the nitrate is $ZNO_3$, wherein Z is hydrogen, lithium, sodium, potassium, ammonium ($NH_4^+$), alkylammonium, phosphonium ($PH_4^+$), alkylphosphonium, arylphosphonium, or trimethyl sulfonium ($[S(CH_3)_3]^+$).

Aspect 17: The method in any one of aspects 1 to 16, wherein the acid comprises trifluoroacetic acid, triflic acid, trifluoromethyl phosphonic acid, hexafluorobutyric acid, sulfuric acid, acetic acid, methanesulfonic acid, phosphoric acid, or any combination thereof.

Aspect 18: The method in any one of aspects 1 to 17, wherein the composition further comprises iodine, an iodine-based compound, or a combination thereof.

Aspect 19: The aspect of claim 18, wherein the iodine-based compound comprises iodate, periodate, iodine oxide, iodosyl ($IO^+$), trivalent iodine compound, or any combination thereof.

Aspect 20: The aspect of claim 18, wherein the iodine-based compound is $Q(IO_3)_p$, wherein Q is hydrogen, lithium, sodium, potassium, beryllium, magnesium, calcium, strontium, barium, transition metals, aluminum, gallium, thallium, indium, tin, sulfur, ammonium ($NH_4^+$), alkylammonium. phosphonium ($PH_4^+$), alkylphosphonium, arylphosphonium, and trimethyl sulfonium ($[S(CH_3)_3]^+$), wherein p is from 1 to 5.

Aspect 21: The method of aspect 18, wherein the iodine-based compound is selected from the group consisting of: $KIO_3$, $Ca(IO_3)_2$, $Ba(IO_3)_2$, $Cu(IO_3)_2$, $NH_4IO_3$, $H_5IO_6$, $KIO_4$, $NaIO_4$ and $NH_4IO_4$, $I(TFA)_3$, $I_2O_5$, $[IO]^+$, $[IO_2]^+$, and any combination thereof.

Aspect 22: The method in any one aspects 18 to 21, wherein the molar ratio of the oxidant to the iodine or iodine-based compound is from 1:1 to 30:1.

Aspect 23: The method in any one of aspects 1 to 22, wherein the composition further comprises $A_aX_n$, wherein A is hydrogen, lithium, sodium, potassium, beryllium, magnesium, calcium, strontium, barium, transition metals, aluminum, gallium, thallium, indium, tin, sulfur, ammonium ($NH_4^+$), alkylammonium. phosphonium ($PH_4^+$), alkylphosphonium, arylphosphonium, or trimethyl sulfonium ($[S(CH_3)_3]^+$) and a combination thereof, wherein X is chlorine, wherein subscript "a" is an oxidation state of X and subscript "n" is an oxidation state of A.

Aspect 24: The method of aspect 23, wherein $A_aX_n$ is HCl, NaCl, KCl, $CaCl_2$), LiCl, $ZnCl_2$, $BeCl_2$, $MgCl_2$, $PCl_3$, $NH_4Cl$, $CCl_4$, $CHCl_3$, transition metal chlorides, main group metal chlorides or organochlorides, or any combination thereof.

Aspect 25: The method of aspect 23 or 24, wherein the molar ratio of the oxidant to $A_aX_n$ is from 1:1 to 10:1.

Aspect 26: The method of aspect 1, wherein the composition comprises $Mn_2(TFA)_4(HTFA)_4$, $Mn(TFA)_3$, or $MnO_2$ and triflouroacetic acid.

Aspect 27: The method of aspect 26, wherein the composition further comprises (i) iodine or an iodine-based compound, (ii) ACI, wherein A is lithium, sodium, potassium, or a combination of (i) and (ii).

Aspect 28: The method of aspect 1, wherein the composition comprises $PbO_2$ or $Pb(TFA)_4$, triflouroacetic acid.

Aspect 29: The method of aspect 28, wherein the composition further comprises (i) iodine or an iodine-based compound, (ii) ACI, wherein A is lithium, sodium, potassium, or a combination of (i) and (ii).

Aspect 30: The method of aspect 1, wherein the composition comprises $CeO_2$ and triflouroacetic acid.

Aspect 31: The method of aspect 30, wherein the composition further comprises (i) iodine or an iodine-based compound, (ii) ACI, wherein A is lithium, sodium, potassium, or a combination of (i) and (ii).

Aspect 32: The method of aspect 1, wherein the composition comprises triflouroacetic acid and $YBiO_3$, wherein Y is lithium, sodium, potassium, or ammonium ($NH_4^+$).

Aspect 33: The method of aspect 32, wherein the composition further comprises (i) iodine or an iodine-based compound, (ii) ACI, wherein A is lithium, sodium, potassium, or a combination of (i) and (ii).

Aspect 34: The method of aspect 1, wherein the composition comprises triflouroacetic acid and $ZNO_3$, wherein Z is hydrogen, lithium, sodium, potassium, or ammonium ($NH_4^+$).

Aspect 35: The method of aspect 34, wherein the composition further comprises (i) iodine or an iodine-based compound, (ii) ACI, wherein A is lithium, sodium, potassium, or a combination of (i) and (ii).

Aspect 36: The method in any one of aspects 1 to 35, wherein the hydrocarbon and composition are heated at a temperature of from about 100° C. to about 300° C.

Aspect 37: The method in any one of aspects 1 to 36, wherein the hydrocarbon comprises a linear or branched alkane or a substituted or unsubstituted cycloalkane.

Aspect 38: The method in any one of aspects 1 to 36, wherein the hydrocarbon comprises methane Aspect 39: The method in any one of aspects 1 to 38, wherein the hydrocarbon is monofunctionalized.

Aspect 40: The method in any one of aspects 1 to 39, wherein the oxidant is regenerated during the functionalization of the hydrocarbon or after the hydrocarbon is functionalized.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1: Nitrate Oxidants

Figure 1:
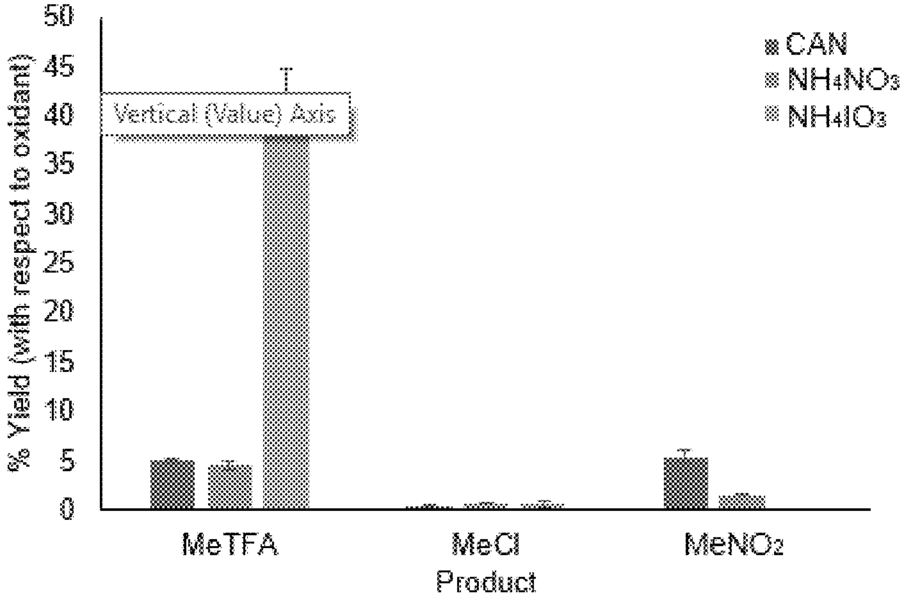
FIG. 1 shows functionalization of methane with KCl and ceric ammonium nitrate (CAN), $NH_4NO_3$, or $NH_4IO_3$. Conditions: $CH_4$ (300 psi), KCl (0.1 mmol), oxidant (1.1 mmol; CAN, $NH_4NO_3$, $NH_4IO_3$), HTFA (8 mL), 180° C., 1 h. Error bars denote standard deviations based on at least three experiments.

The combination of KCl and cerium ammonium nitrate (CAN) resulted in the formation of ~5% yield of both MeTFA and $MeNO_2$ after reaction at 180° C. for 1 h, whereas >40% yield of MeTFA was obtained under those conditions with $NH_4IO_3$ (FIG. 1). The formation of $MeNO_2$ under these conditions was confirmed by spiking a reaction mixture with a known standard and taking a $^1H$ NMR spectrum. Although the use of CAN resulted in lower yields of functionalized product relative to iodate, methane functionalization was observed. To test if the use of cerium (IV) was necessary or if a simple nitrate salt would suffice, $NH_4NO_3$ was studied. Methane was also partially oxidized using $NH_4NO_3$ (FIG. 1). The yield of MeTFA was similar to that with CAN, while the yield of $MeNO_2$ decreased. Minimal amounts of MeCl were also observed with CAN, $NH_4NO_3$ and $NH_4IO_3$ under these conditions. Given that $NH_4NO_3$ exhibited a similar performance to CAN, the use of nitrate as a stoichiometric oxidant was examined further.

Figure 2:
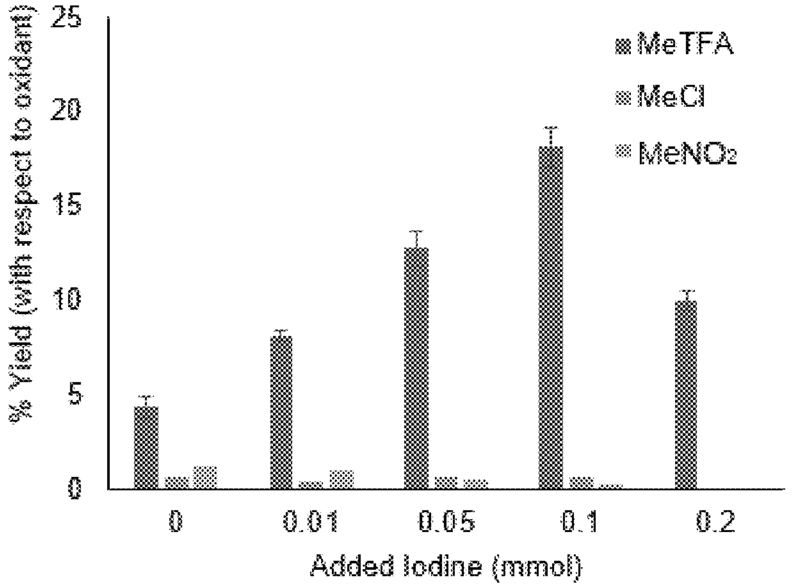
FIG. 2 shows functionalization of methane with KCl/$NH_4NO_3$ as a function of added iodine. Conditions: $CH_4$ (300 psi), KCl 0.1 mmol), $NH_4NO_3$ (1.1 mmol), $I_2$ (0-0.2 mmol), HTFA (8 mL), 180° C., 2 h. Error bars denote standard deviations based on at least three experiments.

With $NH_4NO_3$, the addition of iodine resulted in significantly higher yields of MeTFA, with an increase from 4.4 (6) % yield in the absence of iodine to 18 (1) % yield with 0.1 mmol of iodine (FIG. 2). Similar to the OxE process with iodate, there is a point at which the addition of a larger amount of iodine results in decreased yields. Under the conditions studied using ammonium nitrate (FIG. 2), the addition of 0.2 mmol of iodine resulted in a MeTFA yield of 10.0 (5) % with respect to oxidant, whereas 18 (1) % yield was observed when 0.1 mmol of iodine was added. This decrease in yield is potentially a result of iodine radicals trapping intermediates required for methane functionalization.

Figure 3:
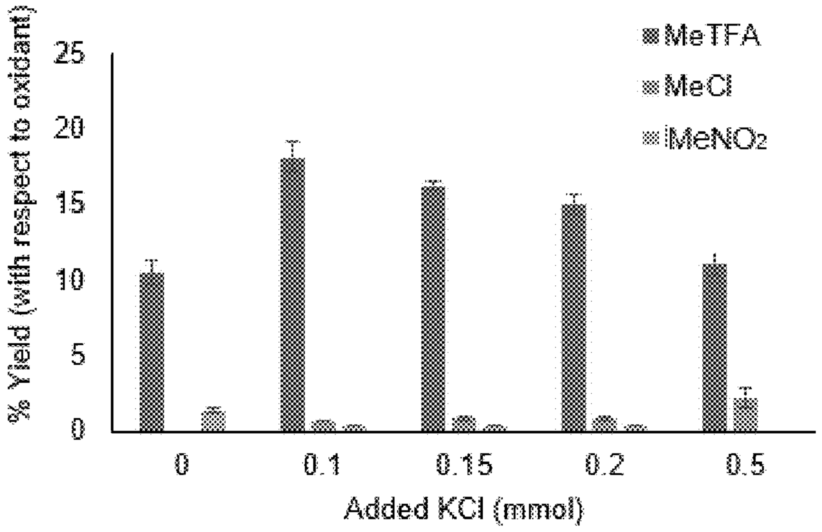
FIG. 3 shows functionalization of methane with $NH_4NO_3$/$I_2$ as a function of added chloride. Conditions: $CH_4$ (300 psi), KCl (0-0.5 mmol), $NH_4NO_3$ (1.1 mmol), $I_2$ (0.1 mmol), HTFA (8 mL), 180° C., 2 h. Error bars denote standard deviations based on at least three experiments.

To study the effect of added chloride on the reaction with $NH_4NO_3$, a variety of chloride loadings were tested, from 0 to 0.5 mmol (FIG. 3). In the absence of chloride, the MeTFA yield decreased to 10.5 (8) % from 18 (1) % with 0.1 mmol of added KCl. With >0.1 mmol of KCl, yields of functionalized products were similar or slightly less than with 0.1 mmol. When using 0.5 mmol of KCl, the yield of MeCl increased slightly, as was observed in the OxE process with iodate.7 Extending the reaction time with optimized chloride and iodine loadings resulted in ~25% total yield of MeX (X=TFA, Cl, $NO_2$) (Scheme 1).

Scheme 1. Methane functionalization under optimized conditions with KCl, $NH_4NO_3$ and $I_2$.

$CH_4$ (300 psi) → [KCl (0.1 mmol), $NH_4NO_3$ (1.1 mmol), $I_2$ (0.1 mmol); HTFA, 180° C., 4 h] → MeTFA 23.8(7)% + MeCl 0.64% + $MeNO_2$ 0.32%

(% yield relative to nitrate)

Conditions: $CH_4$ (300 psi), KCl (0.1 mmol), $NH_4NO_3$ (1.1 mmol), $I_2$ (0.1 mmol), HTFA (8 mL), 180° C., 4 h. Yields are based on three experiments with a standard deviation shown for MeTFA. The yields of MeCl and $MeNO_2$ were identical for all three trials.

Figure 4:
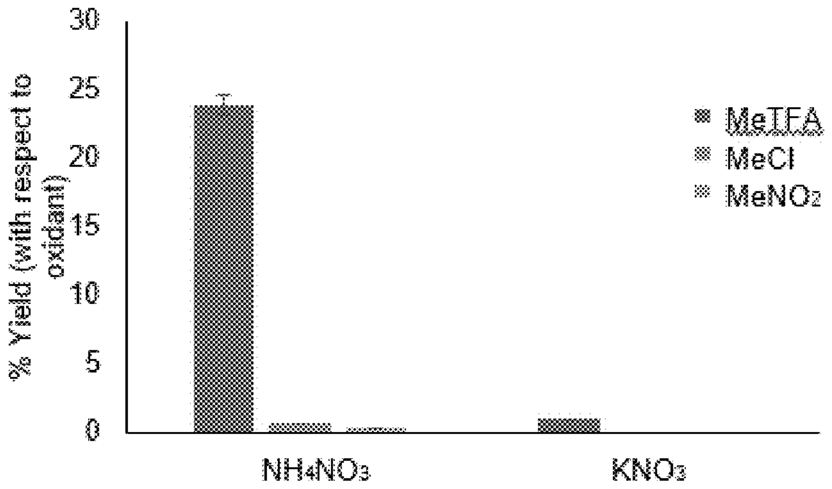
FIG. 4 shows comparison of methane functionalization with $NH_4NO_3$ versus $KNO_3$ under optimized conditions. Conditions: $CH_4$ (300 psi), KCl (0.1 mmol), $NH_4NO_3$ or $KNO_3$ (1.1 mmol), 12 (0.1 mmol), HTFA (8 mL), 180° C., 4 h. Error bars denote standard deviations based on at least three experiments.

The trend observed with iodate where yields with $KIO_3$ are lower than those with $NH_4IO_3$ is also seen with nitrate oxidants (FIG. 4). The effect is more pronounced with nitrate oxidants. With iodate, the yield of MeTFA was about ~50% lower with $KIO_3$ compared to $NH_4IO_3$, while only minimal amounts of MeTFA are obtained when $KNO_3$ is used (FIG. 4).

$NH_4NO_3$ was also tested as an oxidant for ethane functionalization (Scheme 2). This served to demonstrate the potential scope of reactivity of $NH_4NO_3$ and provided further evidence for the formation of $RNO_2$ from RH (R=Me, Et) when nitrates were used as the oxidant. Spiking a reaction mixture with a known standard of nitroethane supported the conclusion that it was generated during the reaction. When using methane as the substrate, spiking the resulting reaction mixture with nitromethane was also consistent with the its formation. Thus, $MeNO_2$ and $EtNO_2$ were concluded to be functionalization products from the reactions with methane and ethane, respectively. Yields relative to nitrate for ethane functionalization are higher than those observed with methane under similar conditions, with ~40% total yield of EtX (X=TFA, $NO_2$) (Scheme 18). The simple nitrate oxidant is selective for the partial oxidation of both methane and ethane, indicating the ability of oxidants other than iodine oxides to be successful in the OxE reaction without deleterious effects with respect to over-oxidation.

Scheme 2. Ethane functionalization under optimized conditions with KCl and $NH_4NO_3$.

$CH_3CH_3$ (300 psi) → [KCl (0.1 mmol), $NH_4NO_3$ (1.1 mmol); HTFA, 180° C., 2 h] → EtTFA 29(2)% + $EtNO_2$ 11.1(6)%

(% yield relative to nitrate)

Conditions: $CH_4$ (300 psi), KCl (0.1 mmol), $NH_4NO_3$ (1.1 mmol), HTFA (8 mL), 180° C., 2 h. Yields and standards deviations based on three experiments are shown.

Example 2: Bismuth Oxidants

Figure 5:
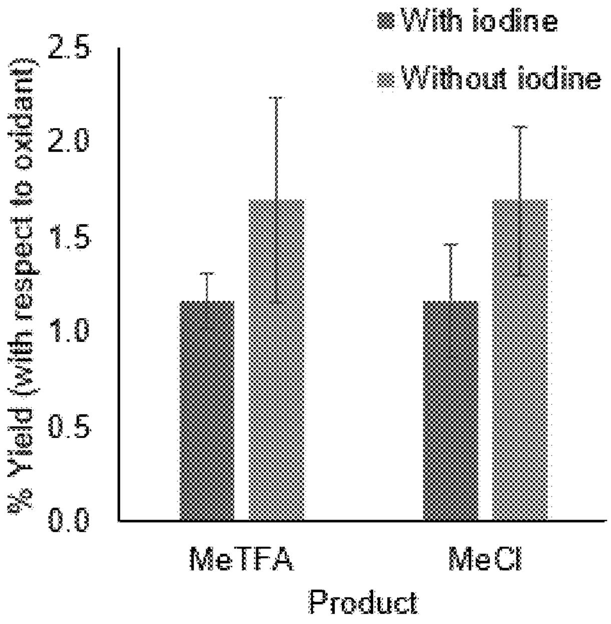
FIG. 5 shows functionalization of methane as a function of added iodine with KCl/$NaBiO_3$. Conditions: $CH_4$ (300 psi), KCl (0.1 mmol), $NaBiO_3$ (1.1 mmol), $I_2$ (if added, 0.05 mmol), HTFA (8 mL), 180° C., 1 h. Error bars denote standard deviations based on three experiments.

For initial screening, sodium bismuth oxide ($NaBiO_3$) was examined. Under the standard set of conditions examined for the nitrate oxidants (see above), $NaBiO_3$ results in slightly lower yields of MeX (X=TFA, Cl) than were observed for the nitrates (FIG. 5, orange). In contrast to the nitrate study, the addition of 0.05 mmol of iodine resulted in somewhat lower average yields of MeX, though yields remain statistically identical to those observed in the absence of added iodine (FIG. 5, blue).

In an effort to determine if the lower observed yields of MeTFA were a result of its instability under reaction conditions with $NaBiO_3$, MeTFA decay was studied at 80° C. for 2 h with $NaBiO_3$ in HTFA in the absence or presence of KCl (Scheme 3). The MeTFA decay observed with $NaBiO_3$ at 80° C. was greater than that under conditions at 140° C. with iodate as the oxidant where minimal loss was observed within 8 h and after 16 h approximately 85% of the starting amount of MeTFA remained. However, with $NaBiO_3$ at a lower temperature, ~85% MeTFA remained after 2 h, whether in the presence or absence of added chloride (Scheme 3). This decrease indicates that MeTFA is likely less stable under functionalization conditions with $NaBiO_3$, providing a potential rationalization for the lower yields that are observed.

Scheme 19. Stability of MeTFA with $NaBiO_3$ with or without added KCl.

Ar (300 psi) → [MeTFA (0.65 mmol), KCl (0 or 0.1 mmol), $NaBiO_3$ (1.1 mmol); HTFA, 180° C., 2 h] → MeTFA remaining: Without KCl: 83(1)%; With KCl: 89(6)%

Conditions: Ar (300 psi), MeTFA (0.65 mmol), KCl (if added, 0.1 mmol), $NaBiO_3$ (1.1. mmol), HTFA (8 mL), 80° C., 2 h. Yields and standard deviations based on three experiments are shown.

Figure 6:
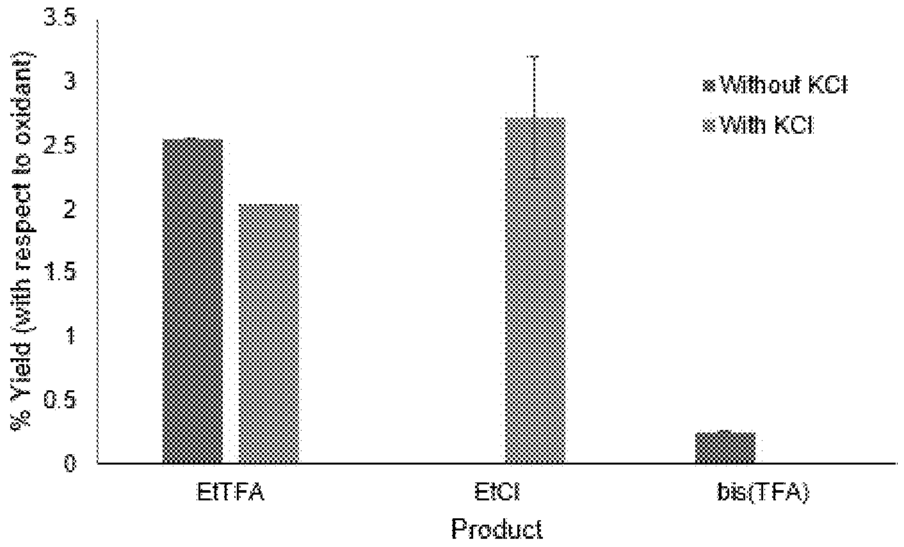
FIG. 6 shows functionalization of ethane as a function of added chloride with $NaBiO_3$. Conditions: $CH_3CH_3$ (300 psi), KCl (if added, 0.1 mmol), $NaBiO_3$ (1.1 mmol), HTFA (8 mL), 80° C., 2 h. Bis (TFA)=1,2-bis(trifluoroacetyl) ethane. Error bars denote standard deviations based on three experiments.
Figure 7:
FIG. 7 shows functionalization of propane as a function of added chloride with $NaBiO_3$. Conditions: propane (100 psi), KCl (if added, 0.1 mmol), $NaBiO_3$ (1.1 mmol), HTFA (8 mL), 80° C., 2 h. Error bars denote standard deviations based on three experiments.
Figure 7:
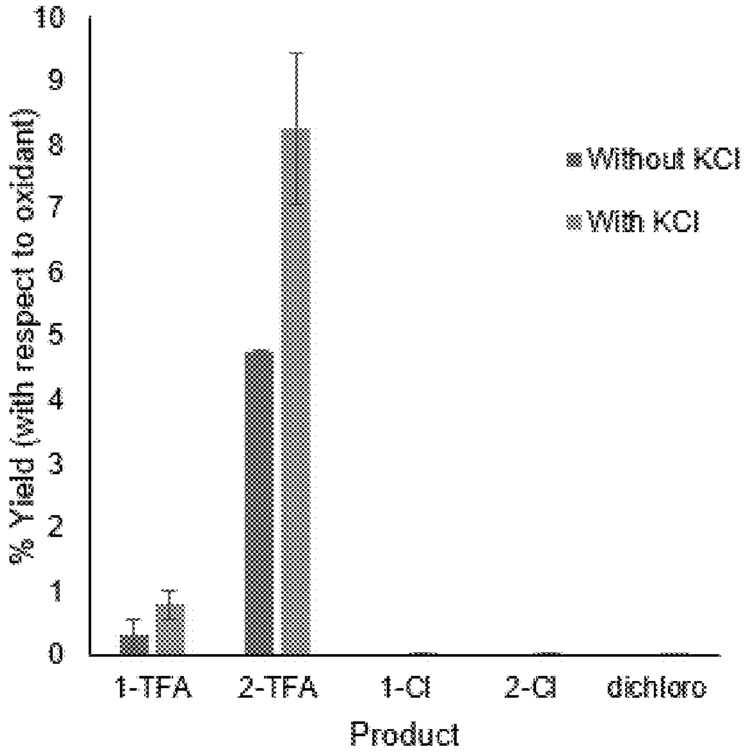

Ethane and propane were also examined as substrates for partial oxidation with $NaBiO_3$. These reactions were performed at lower temperatures to minimize product over-oxidation. Although yields with ethane are slightly higher than those with methane, the total product yields of ethane functionalization are <5%, whether or not KCl is added (FIG. 6). Increasing the temperature to 120° C. or increasing the reaction time did not improve product yields. For propane, yields are somewhat higher, particularly when chloride is added. With added chloride, ~9% total yield of functionalized product is obtained, with the formation of 1-trifluoroacetylethane (1-TFA) and 2-trifluoroacetylethane (2-TFA) highly favored over other products which are observed in trace amounts (FIG. 7).

Example 3: Cerium Oxidants

Under the standard set of conditions for screening, $CeO_2$ resulted in MeTFA formation, but in poor yield with 0.6 (2) % relative to oxidant (Scheme 4). In an effort toward optimization, the addition of 0.1 mmol of 12 was tested. However, as was observed with $NaBiO_3$, the addition of iodine did not result in improved product yields. In fact, only trace amounts of MeTFA were observed when iodine was added to the reaction mixture (Scheme 5). Increasing the chloride loading for the $KCl/CeO_2/I_2$ process similarly did not improve yields of functionalized products (Scheme 6).

Scheme 4. Methane functionalization using $KCl/CeO_2$ in HTFA.

KCl (0.1 mmol)
$CeO_2$ (1.1 mmol)
$CH_4$ (300 psi)
HTFA
180° C., 1 h
MeTFA
0.6(2)% yield
(relative to $CeO_2$)

Conditions: $CH_4$ (300 psi), KCl (0.1 mmol), $CeO_2$ (1.1 mmol), HTFA (8 mL), 180° C., 1 h. Yield and standard deviation are based on three experiments.

Scheme 5. Methane funtionalization using $KCl/CeO_2/I_2$ in HTFA.

KCl (0.1 mmol)
$CeO_2$ (1.1 mmol)
$I_2$ (0.1 mmol)
$CH_4$ (300 psi)
HTFA
180° C., 1 h
MeTFA
(trace)

Conditions: $CH_4$ (300 psi), KCl (0.1 mmol), $CeO_2$ (1.1 mmol), $I_2$ (0.1 mmol), HTFA (8 mL), 180° C., 1 h. Trace MeTFA was observed in three experiments.

Scheme 6. Methane functionalization using $KCl/CeO_2/I_2$ in HTFA.

KCl (0.3 mmol)
$CeO_2$ (1.1 mmol)
$I_2$ (0.1 mmol)
$CH_4$ (300 psi)
HTFA
180° C., 1 h
MeTFA
0.5(2)% yield
(relative to $CeO_2$)

Conditions: $CH_4$ (300 psi), KCl (0.3 mmol), $CeO_2$ (1.1 mmol), $I_2$ (0.1 mmol), HTFA (8 mL), 180° C., 1 h. Yield and standard deviation are based on three experiments.

Example 4: Manganese Oxidants

Using manganese-based oxidants for the process under the standard screening conditions tested for the nitrate-, bismuth- and cerium-based oxidants (see above), $^1H$ NMR results were difficult to interpret due to significant peak broadening. This broadening was minimized through the development of a work-up procedure involving oxidation of reduced manganese species using $NaBiO_3$ following the reaction to minimize peak shifts and broadening due to paramagnetic resonances. The $NaBiO_3$ work-up was utilized for all reactions with manganese-based oxidants. The addition of iodine at the start of the reaction was also critical.

Figure 8:
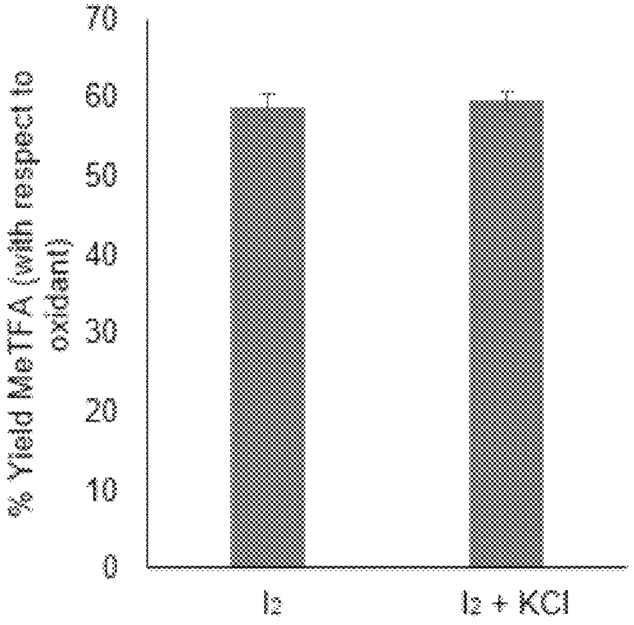
FIG. 8 shows functionalization of methane as a function of additives with $MnO_2$. Conditions: $CH_4$ (300 psi), KCl (0.1 mmol, if added), $MnO_2$ (1.1 mmol), $I_2$ (0.1 mmol), HTFA (8 mL), 180° C., 1 h. Error bars denote standard deviations based on three experiments.

Without added iodine, the resonances remain very broad and yields of MeTFA are ~20% with respect to oxidant. However, the addition of 0.1 mmol of $I_2$ to the standard conditions with $KCl/MnO_2$ resulted in a clean $^1H$ NMR spectrum (see FIG. 28) and the selective production of MeTFA, in 60 (1) % yield (FIG. 8, right). This finding prompted further investigation into the role of additives in this reaction. Chloride was subsequently excluded from the reaction, and the combination of $MnO_2$ and $I_2$ in HTFA resulted in 59 (2) % yield of MeTFA, indicating that chloride was not necessary for the reaction (FIG. 8, left). Consequently, chloride was not added to future reactions studying light alkane functionalization with $MnO_2$.

Figure 9:
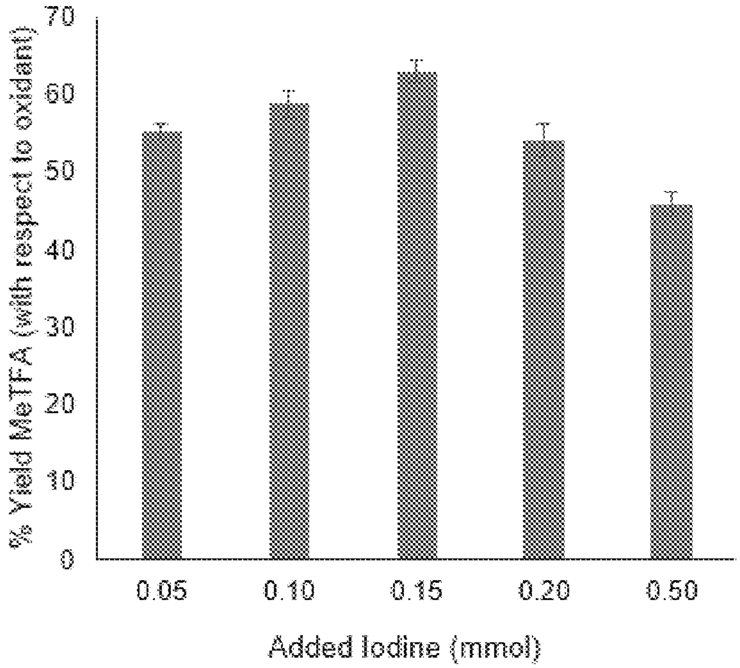
FIG. 9 shows methane functionalization with $MnO_2$ as a function of added iodine.

In contrast to chloride, the addition of iodine had a marked effect on the reaction. Thus, a screening of different iodine loadings was performed. As shown in FIG. 9, highest yields of MeTFA were obtained using 0.15 mmol of iodine, and this amount was used in additional optimization studies. The addition of >0.15 mmol of iodine resulted in lower yields of MeTFA (FIG. 9), similar to what was observed in the original process using iodate as the oxidant.

A range of manganese-based oxidants were tested under the identified optimal additive conditions with $MnO_2$ and 0.15 mmol of iodine (FIG. 10). Interestingly, $MnO_2$, $Mn_2O_3$ and $Mn_3O_4$ each gave ~63% yield of MeTFA, whereas $KMnO_4$, $K_2MnO_4$ and $Mn(OAc)_3 \cdot 2H_2O$ resulted in significantly lower yields of MeTFA of ~20-35%. The lower yields obtained using oxidants with manganese in higher oxidation states were surprising and elucidation of these results is the subject of further study. At present, these results do not appear to follow a clear trend related to the oxidation state of manganese, as Mn(III) oxidants gave the highest and lowest yields in the screening (FIG. 10). However, several manganese oxides were identified as effective oxidants for methane functionalization and gave extremely similar yields to one another, indicating that they might all funnel to the same active intermediate or follow the same mechanistic pathway.

Methane pressures were lowered to determine if higher MeTFA yields relative to methane could be obtained. With a lower pressure of methane, the yield of MeTFA relative to oxidant decreased significantly, thus the yield of MeTFA relative to methane remained statistically identical (FIG. 11). Additional studies sought to understand this effect. First, higher loadings of $MnO_2$ oxidant were examined (FIG. 12). With higher oxidant loadings, yields of MeTFA relative to methane yields increased, though not by an amount proportional to the increased amount of oxidant. Thus, an increase in MeTFA yield from 2.79 (1) % to 3.89 (6) % was observed with 1.1 and 2.2 mmol of $MnO_2$, respectively. However, the MeTFA yield relative to $MnO_2$ decreased from 63 (2) % to 46 (1) % with 1.1 and 2.2 mmol of $MnO_2$. Similarly, increasing the $MnO_2$ loading to 3.3 mmol did not result in a three-fold increase relative to reactions with 1.1 mmol, in fact, the yield of MeTFA was only 1.8 times higher with 3.3 mmol of $MnO_2$. However, this demonstrated that MeTFA yields of up to 5% with respect to methane could be obtained using the $MnO_2/I_2$ process in HTFA.

In contrast, increasing the oxidant loading with Mn $(OAc)_3 \cdot 2H_2O$ did result in proportional increases in MeTFA yields with respect to methane as the yield relative to oxidant remained constant (FIG. 13). Although the yields are lower than those observed with $MnO_2$, this effective scale-up has led to a re-evaluation of $Mn(OAc)_3 \cdot 2H_2O$ as an oxidant for the oxidation system, and additional studies to determine the differences between the reactions with $Mn(OAc)_3 \cdot 2H_2O$ and $MnO_2$ are required.

To determine if increasing the amount of iodine in proportion with the increase in oxidant would result in higher yields of MeTFA, the reaction with doubled loadings of $MnO_2$ and 12 (FIG. 14, right) was compared to the reaction wherein solely the oxidant loading was scaled up (FIG. 14, left). This alteration did not have a significant effect on MeTFA yield, which was surprising given the inhibition observed previously when excess iodine was added (FIG. 9).

One of the hallmarks of the oxidation process is its selectivity for mono-functionalized products. As the manganese-based oxidants also exhibit selectivity for MeTFA formation, the stability of MeTFA under reaction conditions was studied to compare the oxidation of MeTFA with $MnO_2/I_2$ versus iodate/chloride. Reaction conditions for methane functionalization and MeTFA decay similar to those described above were used for $MnO_2$-based functionalization and decay (FIG. 15). The reaction temperature was decreased to 140° C. to slow the rate of functionalization in order to compare it to the rate of decay over time. Methane functionalization is complete after 4 h. Although the MeTFA decay data are less consistent than was previously observed using iodate/chloride, MeTFA is also stable under the reaction conditions with $MnO_2/I_2$. After 16 h under oxidizing conditions, >80% of the starting MeTFA remains. Under identical reaction conditions with iodate/chloride, ~85% remained after that amount of time. These results demonstrate that the rate of over-oxidation of MeTFA is slow compared to the rate of methane functionalization. If using the linear fit of the MeX production data which was forced through zero (FIG. 15, dark blue), the ratio of methane functionalization to MeTFA decay with $MnO_2/I_2$ is approximately 35. Using a linear fit of the data through four hours without forcing the fit through zero (FIG. 15, light blue), the ratio of methane functionalization to MeTFA decay is higher, approximately 54. These values are significantly higher than the ratio of 13 observed using iodate/chloride. As there is significant deviation in the MeTFA decay data with $MnO_2/I_2$, the $R^2$ of the fit for the MeTFA decay data is low. This fit may not be representative of the rate of MeTFA decay, which would result in inflated ratios of methane functionalization to MeTFA decay. However, these data demonstrate that MeTFA decay is significantly slower than methane functionalization with $MnO_2/I_2$, as was also observed with iodate/chloride.

Example 5: Iron Oxidants

As an initial screening, iron (III) oxide and iron 1,3,5-benzenetricarboxylate (Fe-BTC) were examined as potential Fe-based oxidants for the process. Under the standard screening conditions used for new oxidants, Fe-BTC gave high yields of MeTFA, >60% relative to oxidant, while $Fe_2O_3$ produced only trace amounts of MeTFA (FIG. 16). Thus, initial optimization studies focused on the use of Fe-BTC. Surprisingly, varying the chloride loading, adding iodine or omitting both chloride and iodine gave nearly identical yields of MeTFA, all ~60% (FIG. 17). These results indicate that the reaction with Fe-BTC may operate by a different mechanism than the process with iodate/chloride, where the presence of chloride was essential for efficient methane functionalization. With Fe-BTC, chloride is not necessary, nor does the addition of iodine have an effect. As iodine was proposed to be a crucial intermediate in the iodate/chloride process, this is further evidence that functionalization using Fe-BTC may involve a different reaction mechanism. The operative mechanism under conditions with Fe-BTC is the subject of further studies.

Example 6: Copper Oxidants

As Fe-BTC was demonstrated to be a capable oxidant for the partial oxidation of methane, the Cu(II) derivative of the MOF (Cu-BTC) was also examined. The reactivity of Cu-BTC was first studied in the absence of KCl and $I_2$ as those additives did not affect the methane functionalization reaction with Fe-BTC. In the absence of additives, Cu-BTC mediates the conversion of methane to MeTFA in HTFA in 87 (3) % yield relative to oxidant, outperforming Fe-BTC under identical reaction conditions (FIG. 18).

Example 7: Lead Oxidants

The process has been extended to lead (IV) oxidants. $PbO_2$ in HTFA thermally oxidizes methane to MeTFA (Scheme 7). The addition of iodine and chloride increases the yield further, though a small amount of MeCl is formed as a byproduct (Scheme 8). $Pb(TFA)_4$ in HTFA also thermally facilitates methane oxidation. When $Pb(TFA)_4$ is synthesized and isolated as a solid, the hygroscopic salt is capable of thermal methane oxidation in HTFA. When $Pb(TFA)_4$ is synthesized but instead retained in HTFA and then directly used for methane oxidation, the product yield increases drastically (Scheme 10). MeCl is only observed as a byproduct in the case using the salt retained in HTFA; no detectable amount of MeCl is formed from the reaction using the isolated salt.

Scheme 7. Methane functionalization using $PbO_2$ in HTFA. Conditions: $CH_4$ (300 psi), $PbO_2$ (1 mmol), HTFA (8 mL), 180° C., 1 h. Yield and standard deviations are based on three experiments.

$CH_4$ (300 psi)

$PbO_2$ (1 mmol)

HTFA (8 mL)
180° C., 1 h 0.11(1) mmol MeTFA
10.2(9)% yield as function of $PbO_2$
0.46(5)% yield as function of $CH_4$ Scheme 8. Methane functionalization using $PbO_2$ plus additives in HTFA.

$CH_4$ (300 psi)

$PbO_2$ (1 mmol)
KCl (0.15 mmol)
$I_2$ (0.15 mmol)

HTFA (8 mL)
180° C., 1 h 0.42(2) mmol MeTFA
42(2)% yield as function of $PbO_2$
1.75(9)% yield as function of $CH_4$

+

0.012(2) mmol MeCl
1.2(2)% yield as function of $PbO_2$
0.051(9)% yield as function of $CH_4$ Conditions: $CH_4$ (300 psi), $PbO_2$ (1 mmol), KCl (0.15 mmol), $I_2$ (0.15 mmol), HTFA (8 mL), 180° C., 1 h. Yield and standard deviation are based on three experiments.

Scheme 10. Methane functionalization using different $Pb(TFA)_4$ sources plus additives in HTFA.

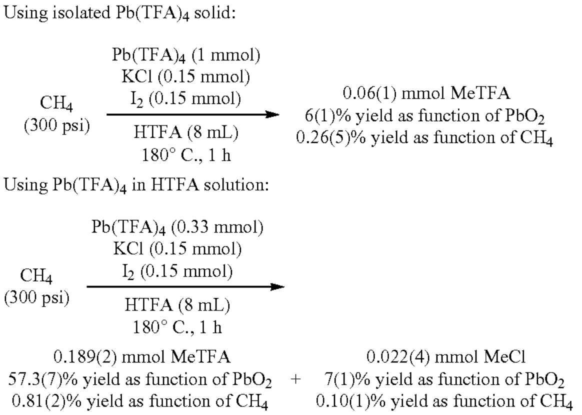

Conditions (top): $CH_4$ (300 psi), $Pb(TFA)_4$ (1 mmol), KCl (0.15 mmol), $I_2$ (0.15 mmol), HTFA (8 mL), 180° C., 1 h. Conditions (bottom): $CH_4$ (300 psi), $Pb(TFA)_4$ (0.33 mmol), KCl (0.15 mmol), $I_2$ (0.15 mmol), HTFA (8 mL), 180° C., 1 h. Yield and standard deviations are based on three experiments.

Example 8: Experimental Details and Characterization for Functionalization of Hydrocarbons Unless noted otherwise, all reactions were performed under ambient atmosphere in custom-built stainless-steel reactors unless otherwise noted. All chemicals were purchased from commercial sources and used as received with the exception of $Pb(TFA)_4$ and $Mn_2(TFA)_4(HTFA)_4$ which were synthesized according to published procedures. Gases were purchased from GTS-Welco and were used as received. NMR analysis was performed using a Varian Inova 500 or NMRS 600 spectrometer. NMR spectra of reaction mixtures were obtained using neat HTFA or HOAc with a $C_6D_6$ capillary as an internal lock reference. Nitromethane or acetic acid were added as internal standards and used to reference $^1H$ NMR spectra (δ 4.18 and 2.04, respectively).

Methane Functionalization with $KCl/NH_4IO_3$ for Comparison to Other Oxidants

A custom-built stainless-steel reactor with a Teflon liner was charged with a stir bar, KCl (0.1 mmol), $NH_4IO_3$ (1.1 mmol) and HTFA (8 mL). The reactor was sealed and pressurized with 300 psi of methane. After the mixture was stirred at 800 rpm at 180° C. for 1 h, the reactor was allowed to cool to room temperature. The reactor was then vented carefully, and HOAc was added as an internal standard. After stirring, an aliquot was removed for centrifugation. The supernatant was analyzed by $^1H$ NMR. A representative $^1H$ NMR spectrum is shown in FIG. 19. This procedure was performed in triplicate.

Methane Functionalization with Nitrate Oxidants

A custom-built stainless-steel reactor with a Teflon liner was charged with a stir bar, KCl (0-0.5 mmol), nitrate oxidant (ceric ammonium nitrate, $NH_4NO_3$ or $KNO_3$, 1.1 mmol), I2 (0-0.2 mmol) and HTFA (8 mL). The reactor was sealed and pressurized with 300 psi of methane. After the mixture was stirred at 800 rpm at 180° C. for 1-4 h, the reactor was allowed to cool to room temperature. The reactor was then vented carefully, and HOAc was added as an internal standard. After stirring, an aliquot was removed for centrifugation. The supernatant was analyzed by $^1H$ NMR. A representative $^1H$ NMR spectrum is shown in FIG. 20. Each condition was performed in triplicate.

Ethane Functionalization with $KCl/NH_4NO_3$

A custom-built stainless-steel reactor with a Teflon liner was charged with a stir bar, KCl (0.1 mmol), $NH_4NO_3$ (1.1 mmol) and HTFA (8 mL). The reactor was sealed and pressurized with 300 psi of methane. After the mixture was stirred at 800 rpm at 180° C. for 2 h, the reactor was allowed to cool to room temperature. The reactor was then vented carefully, and HOAc was added as an internal standard. After stirring, an aliquot was removed for centrifugation. The supernatant was analyzed by $^1H$ NMR. A representative $^1H$ NMR spectrum is shown in FIG. 21. Nitroethane formation was confirmed by spiking a sample with a known standard. This procedure was performed in triplicate.

Methane Functionalization with $NaBiO_3$

A custom-built stainless-steel reactor with a Teflon liner was charged with a stir bar, KCl (0.1 mmol), $NaBiO_3$ (1.1 mmol), $I_2$ (0-0.0.5 mmol) and HTFA (8 mL). The reactor was sealed and pressurized with 300 psi of methane. After the mixture was stirred at 800 rpm at 180° C. for 1 h, the reactor was allowed to cool to room temperature. The reactor was then vented carefully, and HOAc was added as an internal standard. After stirring, an aliquot was removed for centrifugation. The supernatant was analyzed by $^1H$ NMR. A representative $^1H$ NMR spectrum is shown in FIG. 22. Each condition was performed in triplicate.

MeTFA Decay in the Presence of $NaBiO_3$

A custom-built stainless-steel reactor with a Teflon liner was charged with a stir bar, MeTFA (0.65 mmol) KCl (0-0.1 mmol), $NaBiO_3$ (1.1 mmol), $I_2$ (0-0.0.5 mmol) and HTFA (8 mL). The reactor was sealed and pressurized with 300 psi of argon. After the mixture was stirred at 800 rpm at 80° C. for 2 h, the reactor was allowed to cool to room temperature. The reactor was then vented carefully, and HOAc was added as an internal standard. After stirring, an aliquot was removed for centrifugation. The supernatant was analyzed by $^1H$ NMR. A representative $^1H$ NMR spectrum is shown in FIG. 23. This procedure was performed in triplicate.

Ethane Functionalization with $NaBiO_3$

A custom-built stainless-steel reactor with a Teflon liner was charged with a stir bar, KCl (0 or 0.1 mmol), $NaBiO_3$ (1.1 mmol) and HTFA (8 mL). The reactor was sealed and pressurized with 300 psi of ethane. After the mixture was stirred at 800 rpm at 80° C. for 2 h, the reactor was allowed to cool to room temperature. The reactor was then vented carefully, and nitromethane was added as an internal standard. After stirring, an aliquot was removed for centrifugation. The supernatant was analyzed by $^1H$ NMR. A representative $^1H$ NMR spectrum is shown in FIG. 24. Each condition was performed in triplicate.

Propane Functionalization with $NaBiO_3$

A custom-built stainless-steel reactor with a Teflon liner was charged with a stir bar, KCl (0 or 0.1 mmol), $NaBiO_3$ (1.1 mmol) and HTFA (8 mL). The reactor was sealed and pressurized with 100 psi of propane. After the mixture was stirred at 800 rpm at 80° C. for 2 h, the reactor was allowed to cool to room temperature. The reactor was then vented carefully, and HOAc was added as an internal standard. After stirring, an aliquot was removed for centrifugation. The supernatant was analyzed by $^1H$ NMR. A representative $^1H$ NMR spectrum is shown in FIG. 25. Each condition was performed in triplicate.

Methane Functionalization with $CeO_2$

A custom-built stainless-steel reactor with a Teflon liner was charged with a stir bar, KCl (0.1 or 0.3 mmol), $CeO_2$ (1.1 mmol), $I_2$ (0 or 0.1 mmol) and HTFA (8 mL). The reactor was sealed and pressurized with 300 psi of methane. After the mixture was stirred at 800 rpm at 180° C. for 1 h, the reactor was allowed to cool to room temperature. The reactor was then vented carefully, and nitromethane was added as an internal standard. After stirring, an aliquot was removed for centrifugation. The supernatant was analyzed by $^1H$ NMR. A representative $^1H$ NMR spectrum is shown in FIG. 26. Each condition was performed in triplicate.

Methane Functionalization with $MnO_2$

A custom-built stainless-steel reactor with a Teflon liner was charged with a stir bar, KCl (if added, 0.1 mmol), $MnO_2$ (1.1-3.3 mmol), $I_2$ (0.05-0.5 mmol) and HTFA (8 mL). The reactor was sealed and pressurized with 100 or 300 psi of methane. After the mixture was stirred at 800 rpm at 180° C. for 1 h, the reactor was allowed to cool to room temperature. The reactor was then vented carefully, and nitromethane was added as an internal standard. After stirring, a 1 mL aliquot was added to a centrifuge tube with $NaBiO_3$. The centrifuge tube was shaken and then centrifuged. The supernatant was analyzed by $^1H$ NMR. Representative $^1H$ NMR spectra are shown in FIGS. 27-28. Each condition was performed in triplicate.

Screening Mn Oxidants for Methane Functionalization

A custom-built stainless-steel reactor with a Teflon liner was charged with a stir bar, Mn oxidant (1.1 mmol; $MnO_2$, $Mn_2O_3$, $Mn_3O_4$, $KMnO_4$, $K_2MnO_4$ or $Mn(OAc)_3 \cdot 2H_2O$), $I_2$ (0.15 mmol) and HTFA (8 mL). The reactor was sealed and pressurized with 300 psi of methane. After the mixture was stirred at 800 rpm at 180° C. for 1 h, the reactor was allowed to cool to room temperature. The reactor was then vented carefully, and nitromethane was added as an internal standard. After stirring, a 1 mL aliquot was added to a centrifuge tube with $NaBiO_3$. The centrifuge tube was shaken and then centrifuged. The supernatant was analyzed by $^1H$ NMR.

Representative $^1H$ NMR spectra are shown in FIGS. 29-34. Each condition was performed in triplicate.

Increasing $Mn(OAc)_3 \cdot 2H_2O$ Loading for Methane Functionalization

A custom-built stainless-steel reactor with a Teflon liner was charged with a stir bar, $Mn(OAc)_3 \cdot 2H_2O$ (3.3 mmol), $I_2$ (0.15 mmol) and HTFA (8 mL). The reactor was sealed and pressurized with 300 psi of methane. After the mixture was stirred at 800 rpm at 180° C. for 2 h, the reactor was allowed to cool to room temperature. The reactor was then vented carefully, and nitromethane was added as an internal standard. After stirring, a 1 mL aliquot was added to a centrifuge tube with $NaBiO_3$. The centrifuge tube was shaken and then centrifuged. The supernatant was analyzed by $^1H$ NMR. A representative $^1H$ NMR spectrum is shown in FIG. 35. This procedure was performed in triplicate.

Study of MeTFA Functionalization and Decay with $MnO_2/I_2$

Functionalization reactions were set up following the general procedure for methane functionalization listed above using $MnO_2$ (1.1 mmol), $I_2$ (0.15 mmol) and HTFA (8 mL). The reactor was pressurized with 300 psi of methane and heated at 140° C. for 1-5 h. For decay experiments, a custom-built stainless-steel reactor with a Teflon liner was charged with a stir bar, MeTFA (0.63 mmol), $MnO_2$ (1.1 mmol), $I_2$ (0.15) and HTFA (8 mL). To obtain the 0 h time point, the reactor was not pressurized or heated before following the standard work-up procedure. Otherwise, the reactor was sealed before being pressurized with 300 psi of argon and heated at 180° C. for 1-16 h. The reactor was then vented carefully, and nitromethane was added as an internal standard. After stirring, a 1 mL aliquot was added to a centrifuge tube with $NaBiO_3$. The centrifuge tube was shaken and then centrifuged. The supernatant was analyzed by $^1H$ NMR. A representative $^1H$ NMR spectrum from a MeTFA decay reaction is shown in FIG. 36. All data are given as averages of at least three experiments with standard deviations shown.

Solvent Screening for Methane Functionalization with $MnO_2/I_2$

A custom-built stainless-steel reactor with a Teflon liner was charged with a stir bar, $MnO_2$ (1.1 mmol), $I_2$ (0.15 mmol) and solvent {8 mL; HOAc or HTFA/$H_2O$ (7:1 vol/vol)}. The reactor was sealed and pressurized with 300 psi of methane. After the mixture was stirred at 800 rpm at 180° C. for 1 h, the reactor was allowed to cool to room temperature. The reactor was then vented carefully, and nitromethane was added as an internal standard. After stirring, a 1 mL aliquot was added to a centrifuge tube with $NaBiO_3$. The centrifuge tube was shaken and then centrifuged. The supernatant was analyzed by $^1H$ NMR. Representative $^1H$ NMR spectra are shown in FIGS. 37-38. Each condition was performed in triplicate.

General Procedure for Light Alkane Functionalization with Mn Species

A custom-built stainless-steel reactor with a Teflon liner was charged with a stir bar, MnOx (x=1, 2) (1.1 mmol) or a MnTFA salt (100 mg) along with either HTFA (8 mL), TfOH (8 mL) or a mixture of $C_6F_{14}$ (6 mL) and HTFA (2 mmol). The reactor was flushed with 1 atm of $N_2$, air or $O_2$, then sealed and pressurized with 300 psi of methane or ethane. After the mixture was stirred at 800 rpm at 180° C. for 3 or 4 h, the reactor was allowed to cool to room temperature. The reactor was then vented carefully, and $CH_3NO_2$ was added as internal standard. After stirring, an aliquot was removed for centrifugation.

General Procedure for the Use of Fe-Based Oxidants for Methane Functionalization General procedure for the use of Fe-based oxidants for methane functionalization. A custom-built stainless-steel reactor with a Teflon liner was charged with a stir bar, KCl (if added, 0.1-0.3 mmol), Fe oxidant (1.1 mmol; $Fe_2O_3$ or Fe-BTC), $I_2$ (if added, 0.1 mmol) and HTFA (8 mL). The reactor was sealed and pressurized with 300 psi of methane. After the mixture was stirred at 800 rpm at 180° C. for 1 h, the reactor was allowed to cool to room temperature. The reactor was then vented carefully, and nitromethane was added as an internal standard. After stirring, an aliquot was removed and centrifuged. The supernatant was analyzed by $^1H$ NMR. Representative $^1H$ NMR spectra are shown in FIGS. 39-40. Each condition was performed in triplicate.

Methane Functionalization with $PbO_2$ in HTFA

A custom-built stainless-steel reactor with a Teflon liner was charged with a stir bar, $PbO_2$ (1 mmol) and HTFA (8 mL). The reactor was sealed and pressurized with 300 psi of methane. After the mixture was stirred at 800 rpm at 180° C. for 1 h, the reactor was allowed to cool to room temperature. The reactor was then vented carefully, and $CH_3NO_2$ was added as internal standard. After stirring, an aliquot was removed for centrifugation.

Methane Functionalization with Isolated $Pb(TFA)_4/KCl/I_2$

Because of the hygroscopicity of $Pb(TFA)_4$, it is stored in a nitrogen atmosphere glovebox. Inside the glovebox, a custom-built Teflon cup was charged with a stir bar and $Pb(TFA)_4$ (1 mmol) and sealed with parafilm. The Teflon cup was removed from the glovebox and KCl (0.15 mmol), $I_2$ (0.15 mmol), and HTFA (8 mL) were quickly added. The Teflon cup was added to a custom-built stainless-steel reactor which was then sealed and pressurized with 300 psi of methane. After the mixture was stirred at 800 rpm at 180° C. for 1 h, the reactor was allowed to cool to room temperature. The reactor was then vented carefully, and $CH_3NO_2$ was added as internal standard. After stirring, an aliquot was removed for centrifugation.

Methane Functionalization with a Solution of Pb(TFA)/KCl/$I_2$ in HTFA

A custom-built stainless-steel reactor with a Teflon liner was charged with a stir bar, $Pb(TFA)_4$ solution (0.128 M, 0.33 mmol), KCl (0.15 mmol), $I_2$ (0.15 mmol), and HTFA (5.4 mL). The reactor was sealed and pressurized with 300 psi of methane. After the mixture was stirred at 800 rpm at 180° C. for 1 h, the reactor was allowed to cool to room temperature. The reactor was then vented carefully, and $CH_3NO_2$ was added as internal standard. After stirring, an aliquot was removed for centrifugation.

Example 9: In Situ Formation of Active Species from Inactive Species in the Presence of Air or Oxygen Using Mn oxidants for methane oxidation, natively inactive $Mn^{II}$ species can be made active for methane oxidation in the presence of air or pure dioxygen. This is a first step in enabling recycling of oxidants with air or pure dioxygen towards the end goal of catalytic turnover as depicted in Scheme 11.

Scheme 12 sums up experimental conditions in which MnO, inactive for methane activation under $N_2$ atmosphere, becomes active in the presence of oxygen from the air and in the absence of $I_2$.

$Mn^{II}$ and $Mn^{III}$ TFA salts were synthesized under inert atmosphere (Scheme 13). They showed no activity for methane oxidation under $N_2$, but became active under $O_2$ or air atmosphere (Scheme 14). This is of particular interest as the structure of these species is thought to be very close to that of "$MnOx_{red}$", the reduced form of Mn arising from spent oxidant (Scheme 11). These findings expand the scope of potential claims to the salts of transition metals, as well as to air/dioxygen recyclable or air/dioxygen-enabled oxidants, and to recyclable or catalytic reaction processes turning over as a function of a transition metal oxide or its salts.

Scheme 11. Proposed ideal catalytic or recycled mechanism for selective methane oxidation to methanol using manganese oxides, in which the reduced form of manganese can be reoxidized to an active form of manganese using oxygen to form water as the only byproduct. MeTFA is then hydrolyzed to yield methanol and recover HTFA.

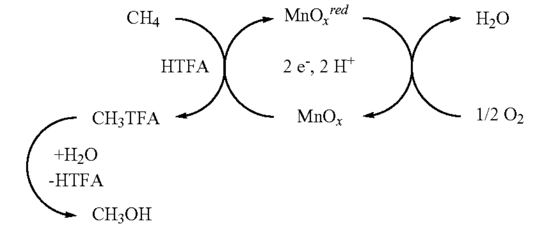

SCHEME 12

Methane functionalization using different MnO HTFA, and yields of MeTFA as a function of reaction conditions.

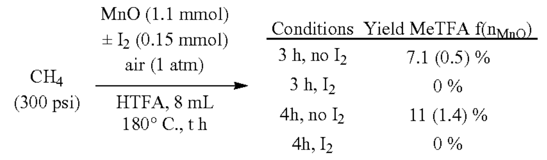

Scheme 13. Synthesis of $Mn^{II}$ and $Mn^{III}$ TFA salts. $Mn^{II}$ salt was made following a published procedure.

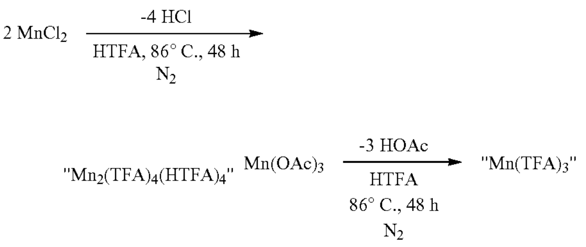

Scheme 14. Activity of $Mn^{II}$ and $Mn^{III}$ TFA salts for methane activation in HTFA in the presence of $N_2$ or $O_2$ atmospheres.

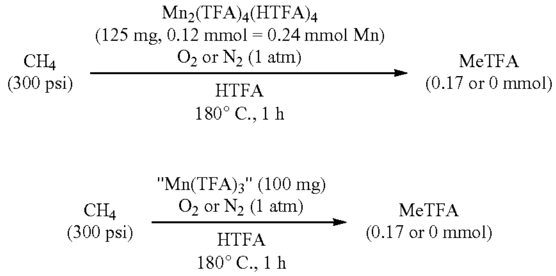

Example 10: Extension of Process to Other Solvent Systems

With ammonium iodate as oxidant in the presence of chloride, methane to TfOMe conversion is catalytic in chloride (Scheme 15).

Scheme 15. Methane functionalization using $KCl/NH_4IO_3$ in TfOH.

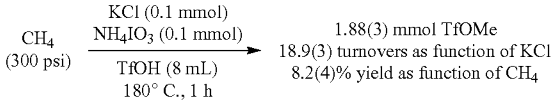

Conditions: $CH_4$ (300 psi), KCl (0.1 mmol), $NH_4IO_3$ (1.1 mmol), TfOH (8 mL), 180° C., 1 h. Yield and standard deviations are based on two experiments.

This is also true for oxidation of methane using $MnO_2$, albeit with worse yields than seen in HTFA (Scheme 16)

Scheme 16. Activity of $MnO_2$ for methane activation in HOTf.

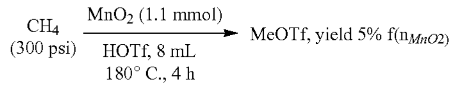

Furthermore, the process has also been shown to work in perfluorinated hexanes with added stoichiometric amounts of HTFA (Scheme 17), with a yield at 3 hours identical to $MnO_2$ driven methane oxidation run in pure HTFA. These results expand the scope of eventual patent claims to the use of the process in other solvents somewhat similar to HTFA, and to systems in which the solvent is unreactive towards methane activation in the presence of added acid.

Scheme 17. Activity of $MnO_2$ for methane activation in $C_6F_{14}$ with added stoichiometric amounts of HTFA.

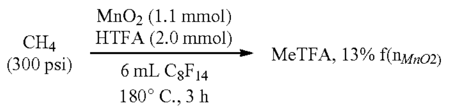

Methane Functionalization with $KCl/NH_4/O_3$ in TfOH

A custom-built stainless-steel reactor with a Teflon liner was charged with a stir bar, KCl (0.1 mmol), $NH_4IO_3$ (1.1 mmol) and TfOH (8 mL). The reactor was sealed and pressurized with 300 psi of methane. After the mixture was stirred at 800 rpm at 180° C. for 1 h, the reactor was allowed to cool to room temperature. The reactor was then vented carefully, and $CH_3NO_2$ was added as internal standard. After stirring, an aliquot was removed for centrifugation.

Example 11: High Selectivity for Mono-Functionalized Product at High Conversion of Ethane Under further optimized reaction conditions, very high conversion of ethane to EtTFA and $TFACH_2CH_2TFA$ is observed, at high selectivity for the mono-oxidized product (Scheme 18). This expands the range of selectivity and conversion of potential claims for the oxidation of other light alkanes than methane.

Scheme 18. Activity of $MnO_2$ for ethane activation in HTFA with added iodine. Yield and standard deviations are based on three experiments.

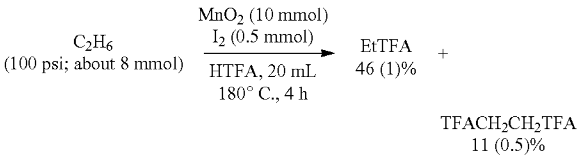

Overall conversion 57%, with 81% mono-oxidation product

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

REFERENCES

1) Aglulin, A. G. Kinet. Catal. 2009, 50, 427-434
2) Arndtsen, B. A.; Bergman, R. G.; Mobley, T. A.; Peterson, T. H. Selective Intermolecular Carbon-Hydrogen Bond Activation by Synthetic Metal Complexes in Homogeneous Solution. Acc. Chem. Res. 1995, 28, 154-162.
3) Bal'zhinimaev, B. S.; Paukshtis, E. A.; Kovalev, E. V.; Suknev, A. P.; Shalygin, A. S. (Uchrezhdenie RAN Institut Kataliza im. G. K. Boreskova S O RAN). Method of Selective Catalytic Oxychlorination of Methane to Methyl Chloride. RU U.S. Pat. No. 2,446,881C2, Apr. 10, 2012
4) Barton, D. H. R.; Martell, A. E.; Sawyer, D. T. In The Activation of Dioxygen and Homogeneous Catalytic Oxidation, Fifth International Symposium on the Activation of Dioxygen and Homogeneous Catalytic Oxidation, College Station, TX, Springer Science and Business Media, LLC: College Station, TX, 1993.
5) Bell, H. C.; Kalman, J. R.; Pinhey, J. T.; Sternhell, S. Aust. J. Chem., 1979, 32, 1521-1530.
6) Benson, S. W. III-Bond Energies. J. Chem. Ed. 1965, 42, 502.
7) Bering, L.; Antonchick, A. P. Selective Transition-Metal-Free Vicinal Cis-Dihydroxylation of Saturated Hydrocarbons. Chem. Sci. 2017, 8, 452-457.
8) Blanksby, S. J.; Ellison, G. B. Bond Dissociation Energies of Organic Molecules. Acc. Chem. Res. 2003, 36, 255-263.
9) BP Statistical Review of World Energy 2014; BP: London, 2014.
10) Breed, A.; Doherty, M. F.; Gadewar, S.; Grosso, P.; Lorkovic, I. M.; McFarland, E. W.; Weiss, M. Natural Gas Conversion to Liquid Fuels in a Zone Reactor. Catal. Today 2005, 106, 301-304.
11) Brooks, D. Shale gas revolution. New York Times, Nov. 3, 2011, p A31.
12) C. P. Guntlin, T. Zund, K. V. Kravchyk, M. Worle, M. I. Bodnarchuk, M. V. Kovalenko, J. Mater. Chem. A 2017, 5, 7383-7393.
13) Cambie, R. C.; Chambers, D.; Lindsay, B. G.; Rutledge, P. S.; Woodgate, P. D. Oxidative Displacement of Hypervalent Iodine from Alkyl Iodides. J. Chem. Soc., Perkin Trans. 1 1980, 0, 822-827
14) Carroll, R. T.; De Witt, E. J.; Trapasso, L. E. Oxychlorination of lower alkanes. 3, 173,962, 1965.
15) Chan, B.; Easton, C. J.; Radom, L. Outcome-Changing Effect of Polarity Reversal in Hydrogen-Atom-Abstraction Reactions. J. Phys. Chem. A 2015, 119, 3843-3847.
16) Chapter 15.7: Fossil Fuels. In General Chemistry for Engineering; Halpern, J.; Sinex, S.; Johnson, S.; Eds.; Prince George's Community College: Largo, MD, 2016.
17) Chen, W.; Kocal, J. A.; Brandvold, T. A.; Bricker, M. L.; Bare, S. R.; Broach, R. W.; Greenlay, N.; Popp, K.; Walenga, J. T.; Yang, S. S.; Low, J. J., Manganese oxide catalyzed methane partial oxidation in trifluoroacetic acid: Catalysis and kinetic analysis. Catal. Today 2009, 140, 157-161.

18) Cheng, W.-H.; Kung, H. H. Methanol Production and Use; Marcel Dekker: New York, NY, 1994; pp 283-317.

19) Chepaikin, E. G. Russ. Chem. Rev. 2011, 80, 363-396

20) Conley, B. L.; Tenn III, W. J.; Young, K. J. H.; Ganesh, S. K.; Meier, S.; Ziatdinov, V. R.; Mironov, O.; Oxgaard, J.; Gonzales, J. M.; Goddard III, W. A.; Periana, R. A. Methane Functionalization. In Activation of Small Molecules: Organometallic and Bioinorganic Perspectives, Tolman, W. B., Ed. Wiley-VCH: Weinheim, Germany, 2006; p 235.

21) Conley, B. L.; Tenn, W. J.; Young, K. J. H.; Ganesh, S. K.; Meier, S. K.; Ziatdinov, V. R.; Mironov, O.; Oxgaard, J.; Gonzales, J.; Goddard III, W. A.; Periana, R. A. Design and Study of Homogeneous Catalysts for the Selective, Low Temperature Oxidation of Hydrocarbons. J. Mol. Catal. A: Chem. 2006, 251, 8-23.

22) Coseri, S. Phthalimide-N-Oxyl (PINO) Radical, a Powerful Catalytic Agent: Its Generation and Versatility Towards Various Organic Substrates. Catal. Rev.: Sci. Eng. 2009, 51, 218-292.

23) Crabtree, R. H. Aspects of Methane Chemistry. Chem. Rev. 1995, 95, 987-1007.

24) CRC Handbook of Chemistry and Physics. 65th ed.; CRC Press: Boca Raton, FL, 1984.

25) Davidson, R. I.; Kropp, P. J. Oxidatively Assisted Nucleophilic Substitution/Elimination of Alkyl lodides in Alcoholic Media. A Further Study. J. Org. Chem. 1982, 47, 1904-1909.

26) Day, J. C.; Lindstrom, M. J.; Skell, P. S. Succinimidyl Radical as a Chain Carrier. Mechanism of Allylic Bromination. J. Am. Chem. Soc. 1974, 96, 5616-5617.

27) Donchak, V. A.; Voronov, S. A.; Yur'ev, R. S. New Synthesis of Tert-Butyl Peroxycarboxylates. Russ. J. Org. Chem. 2006, 42, 487-490.

28) Dunn Jr., J. L.; Posey Jr., B. Fixed bed oxychlorination of hydrocarbons. U.S. Pat. No. 2,866,830 A, Dec. 30, 1958, 1958.

29) Fattahi, A.; McCarthy, R. E.; Ahmad, M. R.; Kass, S. R. Why Does Cyclopropane Have the Acidity of an Acetylene but the Bond Energy of Methane? J. Am. Chem. Soc. 2003, 125, 11746-11750.

30) Fekl, U.; Goldberg, K. I. Adv. Inorg. Chem. 2003, 54, 259-320

31) Fokin, A. A.; Schreiner, P. R. Selective Alkane Transformations via Radicals and Radical Cations: Insights into the Activation Step from Experiment and Theory. Chem. Rev. 2002, 102, 1551-1593.

32) Fortman, G. C.; Boaz, N. C.; Munz, D.; Konnick, M. M.; Periana, R. A.; Groves, J. T.; Gunnoe, T. B., Selective Monooxidation of Light Alkanes Using Chloride and lodate. J. Am. Chem. Soc. 2014, 136, 8393-8401.

33) Fu, R.; Nielsen, R. J.; Goddard, W. A. III; Fortman, G. C.; Gunnoe, T. B. ACS Catal. 2014, 4, 4455-4465.

34) Fu, R.; Nielsen, R. J.; Schwartz, N. A.; Goddard III, W. A.; Gunnoe, T. B.; Groves, J. T., DFT Mechanistic Study of Methane Monooxygenation by Hypervalent lodine Alkane Oxidation (HIAO) Process. Manuscript submitted 2018.

35) Gang, X.; Zhu, Y.; Birch, H.; Hjuler, H. A.; Bjerrum, N. J. lodine as Catalyst for the Direct Oxidation of Methane to Methyl Sulfates in Oleum. Appl. Catal., A 2004, 261, 91-98.

36) General Chemistry: An Atoms First Approach; Halpern, J., Ed.; Howard University: Washington, 2014.

37) Gerken, J. B.; Stahl, S. S., High-potential electrocatalytic 02 reduction with nitroxyl/NOx mediators: Implications for fuel cells and aerobic oxidation catalysis. ACS Cent. Sci. 2015, 1, 234-243.

38) Goldberg, K. I.; Goldman, A. S. Large-Scale Selective Functionalization of Alkanes. Acc. Chem. Res. 2017, 50, 620-626.

39) Goldshlegger, N. F.; Eskova, V. V.; Shilov, A. E.; Shteinman, A. A. Zh. Fiz. Khim. 1972, 46, 1353-1354

40) Goldshlegger, N. F.; Tyabin, M. B.; Shilov, A. E.; Shteinman, A. A. Zh. Fiz. Khim. 1969, 43, 2174-2175

41) Gunsalus, N. J.; Koppaka, A.; Park, S. H.; Bischof, S. M.; Hashiguchi, B. G.; Periana, R. A. Homogeneous Functionalization of Methane. Chem. Rev. 2017, 117, 8497-8520.

42) Hashiguchi, B. G.; Konnick, M. M.; Bischof, S. M.; Gustafson, S. J.; Devarajan, D.; Gunsalus, N.; Ess, D. H.; Periana, R. A. Main-Group Compounds Selectively Oxidize Mixtures of Methane, Ethane, and Propane to Alcohol Esters. Science 2014, 343, 1232-1237.

43) He, J.; Xu, T.; Wang, Z.; Zhang, Q.; Deng, W.; Wang, Y. Transformation of Methane to Propylene: A Two-Step Reaction Route Catalyzed by Modified $CeO_2$ Nanocrystals and Zeolites. Angew. Chem., Int. Ed. 2012, 51, 2438-2442.

44) Hermans, I.; Jacobs, P.; Peeters, J. Autoxidation Catalysis with N-Hydroxyimides: More-Reactive Radicals or Just More Radicals? Phys. Chem. Chem. Phys. 2007, 9, 686-690.

45) Hook, S. C. W.; Saville, B. The Trapping of Carbon Radicals. The Competition of Oxygen and Iodine for the 1,1-Diphenylethyl Radical. J. Chem. Soc., Perkin Trans. 2 1975, 589-593.

46) ICIS. Methanol Prices, Markets, & Analysis. http://www.icis.com/chemicals/methanol/(accessed Jan. 29, 2017).

47) Jaronsińska, M.; Lubkowski, K.; Sosnicki, J. G.; Michalkiewicz, B. Application of Halogens as Catalysts of $CH_4$ Esterification. Catal. Lett. 2008, 126, 407-412.

48) Jones, C. J.; Taube, D.; Ziatdinov, V. R.; Periana, R. A.; Nielsen, R. J.; Oxgaard, J.; Goddard III, W. A. Selective Oxidation of Methane to Methanol Catalyzed, with C—H Activation, by Homogeneous, Cationic Gold. Angew. Chem., Int. Ed. 2004, 116, 4726-4729.

49) Kalman, S. E.; Munz, D.; Fortman, G. C.; Boaz, N. C.; Groves, J. T.; Gunnoe, T. B. Partial Oxidation of Light Alkanes by Periodate and Chloride Salts. Dalton Trans. 2015, 44, 5294-5298.

50) Kao, L. C.; Hutson, A. C.; Sen, A. J. Am. Chem. Soc. 1991, 113, 700-701.

51) Keiichi, M.; Rokuo, U.; Shigeyoshi, O.; Susumu, M. Chlorination Process. U.S. Pat. No. 3,267,161A, Aug. 16, 1966.

52) Konnick, M. M.; Hashiguchi, B. G.; Devarajan, D.; Boaz, N. C.; Gunnoe, T. B.; Groves, J. T.; Ess, D. H.; Periana, R. A. Electrophilic C—H Functionalization of Methane, Ethane and Propane by a Perfluoroarene lodine (III) Complex in Carboxylic Acid Media. Angew. Chem., Int. Ed. 2014, 53, 10490-10494.

53) Koshino, N.; Cai, Y.; Espenson, J. H. Kinetic Study of the Phthalimide N-Oxyl (PINO) Radical in Acetic Acid. Hydrogen Abstraction from C—H Bonds and Evaluation of O—H Bond Dissociation Energy of N-Hydroxyphthalimide. J. Phys. Chem. A 2003, 107, 4262-4267.

54) Koval, I. V. N-Halosuccinimides in Organic Synthesis and in Chemistry of Natural Compounds. Russ. J. Org. Chem. 2002, 38, 301-337.

55) Krause, E.; Roka, K. Process for the chlorination of hydrocarbons. 1,591,984, 1926.

56) Labinger, J. A. Selective Alkane Oxidation: Hot and Cold Approaches to a Hot Problem. J. Mol. Catal. A: Chem. 2004, 220, 27-35.

57) Lee, S. Methane and Its Derivatives. Marcel Dekker, Inc.: New York, NY, 1997, p 289.

58) Lersch, M.; Tilset, M. Chem. Rev. 2005, 105, 2471-2526.

59) Leyva-Pérez, A.; Cómbita-Merchán, D.; Cabrero-Antonino, J. R.; Al-Resayes, S. A.; Corma, A., Oxyhalogenation of activated arenes with nanocrystalline ceria. ACS Catal. 2013, 3 (2), 250-258.

60) Lin, R.; Amrute, A. P.; Pérez-Ramírez, J. Halogen-Mediated Conversion of Hydrocarbons to Commodities. Chem. Rev. 2017, 117, 4182-4247.

61) Lin, R.; Ding, Y.; Gong, L.; Dong, W.; Wang, J.; Zhang, T. Efficient and Stable Silica-Supported Iron Phosphate Catalysts for Oxidative Bromination of Methane. J. Catal. 2010, 272, 65-73.

62) Lin, R.; Ding, Y.; Gong, L.; Li, J.; Chen, W.; Yan, L.; Lu, Y. Oxidative Bromination of Methane on Silica-Supported Non-Noble Metal Oxide Catalysts. Appl. Catal., A. 2009, 353, 87-92.

63) Liu, Z.; Huang, L.; Li, W. S.; Yang, F.; Au, C. T.; Zhou, X. P. Higher Hydrocarbons from Methane Condensation Mediated by HBr. J. Mol. Catal. A: Chem. 2007, 273, 14-20.

64) Macdonald, T. L.; Narasimhan, N.; Burka, L. T. Chemical and Biological Oxidation of Organohalides. J. Am. Chem. Soc. 1980, 102, 7760-7765.

65) Magistro, A. J.; Nicholas, P. P.; Carroll, R. T., Oxychlorination of ethylene at high temperatures. J. Org. Chem. 1969, 34 (2), 271-273.

66) Marchaj, A.; Kelley, D. G.; Bakac, A.; Espenson, J. H. Kinetics of the Reactions between Alkyl Radicals and Molecular Oxygen in Aqueous Solution. J. Phys. Chem. 1991, 95, 4440-4441.

67) Martens, J. A.; Bogaerts, A.; De Kimpe, N.; Jacobs, P. A.; Marin, G.; Rabaey, K.; Saeys, M.; Verhelst, S. The Chemical Route to a Carbon Dioxide Neutral World. ChemSusChem 2017, 10, 1039-1055.

68) McFarland, E. Unconventional Chemistry for Unconventional Natural Gas. Science 2012, 338, 340-342.

69) Mezyk, S. P.; Madden, K. P. Arrhenius Parameter Determination for the Reaction of Methyl Radicals with lodine Species in Aqueous Solution. J. Phys. Chem. 1996, 100, 9360-9364.

70) Michalkiewicz, B. Methane Oxidation to Methyl Bisulfate in Oleum at Ambient Pressure in the Presence of lodine as a Catalyst. Appl. Catal., A 2011, 394, 266-268.

71) Michalkiewicz, B.; Jaronsińska, M.; Łukasiewicz, I. Kinetic Study on Catalytic Methane Esterification in Oleum Catalyzed by lodine. Chem. Eng. J. 2009, 154, 156-161.

72) Mosher, M. W.; Estes, G. W. Free-Radical Halogenations. Chlorination of Alkanes by N-Chlorophthalimide. J. Am. Chem. Soc. 1977, 99, 6928-6932.

73) Munz, D.; Webster-Gardiner, M. S.; Fu, R.; Strassner, T.; Goddard, W. A. III; Gunnoe, T. B. ACS Catal. 2015, 5, 769-775

74) National Renewable Energy Laboratory. Subcontract Report NREL/SR-510-39943: Equipment Design and Cost Estimation for Small Modular Biomass Systems, Synthesis Gas Cleanup, and Oxygen Separation Equipment. http://www.nrel.gov/docs/fy06osti/39943.pdf (accessed Jan. 29, 2017)

75) O'Reilly, M. E.; Fu, R.; Nielsen, R. J.; Sabat, M.; Goddard, W. A. III; Gunnoe, T. B. J. Am. Chem. Soc. 2014, 136, 14690-14693

76) Olah, G. A.; Goeppert, A.; Prakash, G. K. S. Beyond Oil and Gas: The Methanol Economy, Wiley-VCH Verlag Gmbh & Co. KGaA, Weinheim, Germany: 2009; p 179.

77) Owen, J. S.; Labinger, J. A.; Bercaw, J. E. Kinetics and Mechanism of Methane, Methanol, and Dimethyl Ether C—H Activation with Electrophilic Platinum Complexes. J. Am. Chem. Soc. 2006, 128, 2005-2016.

78) Pachauri, R. K.; Reisinger, A. The Fourth Assessment Report of the Intergovernmental Panel on Climate Change; Working Group 1: Geneva, Switzerland, 2007, Chapter 2.

79) Paunović, V.; Zichitella, G.; Moser, M.; Amrute, A. P.; Pérez-Ramírez, Catalyst Design for Natural-Gas Upgrading through Oxybromination Chemistry. J. Nat. Chem. 2016, 8, 803-809.

80) Periana, R. A.; Mirinov, O.; Taube, D. J.; Gamble, S. High Yield Conversion of Methane to Methyl Bisulfate Catalyzed by lodine Cations. Chem Commun. 2002, 2376-2377.

81) Periana, R. A.; Taube, D. J.; Evitt, E. R.; Löffler, D. G.; Wentrcek, P. R.; Voss, G.; Masuda, T. A Mercury-Catalyzed, High-Yield System for the Oxidation of Methane to Methanol. Science 1993, 259, 340-343.

82) Periana, R. A.; Taube, D. J.; Gamble, S.; Taube, H.; Satoh, T.; Fujii, H. Platinum Catalysts for the High-Yield Oxidation of Methane to a Methanol Derivative. Science 1988, 280, 560-564.

83) Periana, R. A.; Taube, D. J.; Taube, H.; Evitt, E. R. (Catalytica, Inc.). Catalytic Process for Converting Lower Alkanes to Esters, Alcohols, and to Hydrocarbons. U.S. Pat. No. 5,306,855A, Apr. 26, 1994

84) Pieters, W. J. M.; Conner, W. C.; Carlson, E. J. The Oxyhydrochlorination of Methane on Fumed Silica-Based Cu(I), K, La Catalysts: I. Catalyst Synthesis. Appl. Catal. 1984, 11, 35-48.

85) Podkolzin, S. G.; Stangland, E. E.; Jones, M. E.; Peringer, E.; Lercher, J. A. Methyl Chloride Production from Methane over Lanthanum-Based Catalysts. J. Am. Chem. Soc. 2007, 129, 2569-2576.

86) Riegel, H.; Schindler, H. D.; Sze, M. C. (CE Lummus). Oxychlorination of Methane. U.S. Pat. No. 4,207,268A, Jun. 10, 1980.

87) Rosen, M. A.; Scott, D. S. Energy and Exergy Analyses of a Production Process for Methanol from Natural Gas. Int. J. Hydrogen Energy 1988, 13, 617-623.

88) Rozanov, V. N.; Gvozd, E. V.; Kernerman, V. A.; Svetlanov, E. B.; Trushechkina, M. A.; Treger, Y. A. Kinet. Catal. 1989, 30, 148-154

89) Rueda-Becerril, M.; Chatalova Sazepin, C.; Leung, J. C. T.; Okbinoglu, T.; Kennepohl, P.; Paquin, J.-F.; Sammis, G. M. Fluorine Transfer to Alkyl Radicals. J. Am. Chem. Soc. 2012, 134, 4026-4029.

90) Sakakura, A.; Kawajiri, K.; Ohkubo, T.; Kosugi, Y.; Ishihara, K. Widely Useful DMAP-Catalyzed Esterification under Auxiliary Base-and Solvent-Free Conditions. J. Am. Chem. Soc. 2007, 129, 14775-14779.

91) Scharfe, M.; Capdevila-Cortada, M.; Kondratenko, V. A.; Kontratenko, E. V.; Colussi, S.; Trovarelli, A.; López, N.; Pérez-Ramírez, J., Mechanism of ethylene oxychlorination on ceria. ACS Catal. 2018, 8 (4), 2651-2663.

92) Scharfe, M.; Lira-Parada, P. A.; Paunović, V.; Moser, M.; Amrute, A. P.; Pérez-Ramírez, J., Oxychlorination-dehydrochlorination chemistry on bifunctional ceria catalysts for intensified vinyl chloride production. Angew. Chem. Int. Ed. 2016, 55 (9), 3068-3072.
93) Schnoor, J. L. Shale Gas and Hydrofracturing. Environ. Sci. Tech. 2012, 46, 4686.
94) Schwach, P.; Pan, X.; Bao, X. Direct Conversion of Methane to Value-Added Chemicals over Heterogeneous Catalysts: Challenges and Prospects. Chem. Rev. 2017, 117, 8497-8520.
95) Schwartz, N. A.; Boaz, N. C.; Kalman, S. E.; Zhuang, T.; Goldberg, J. M.; Fu, R.; Nielsen, R. J.; Goddard III, W. A.; Groves, J. T.; Gunnoe, T. B., Mechanism of Hydrocarbon Functionalization by and lodate/Chloride System: The Role of Ester Protection. ACS Catal. 2018, 8, 3138-3149.
96) Schweizer, A. E.; Jones, M. E.; Hickman, D. A. Oxidative halogenation of C1 hydrocarbons to halogenated C1 hydrocarbons and integrated processes related thereto. U.S. Pat. No. 6,452,058B1, Sep. 17, 2002.
97) Sen, A. Catalytic Functionalization of Carbon-Hydrogen and Carbon-Carbon Bonds in Protic Media. Acc. Chem. Res. 1998, 31, 550-557.
98) Shalygin, A.; Paukshtis, E.; Kovalyov, E.; Bal'zhinimaev, B. Light Olefins Synthesis from C1-C2 Paraffins via Oxychlorination Processes. Front. Sci. Eng. 2013, 7, 279-288.
99) Shilov, A. E.; Shul'pin, G. B. Activation and Catalytic Reactions of Alkanes in Solutions of Metal Complexes. Russ. Chem. Rev. 1987, 56, 442-464.
100) Shilov, A. E.; Shul'pin, G. B. Activation and Catalytic Reactions of Saturated Hydrocarbons in the Presence of Metal Complexes; Kluwer Academic Publishers: Dordrecht, 2000; pp 259-317.
101) Smith, G. W.; Williams, H. D. Some Reactions of Adamantane and Adamantane Derivatives. J. Org. Chem. 1961, 26, 2207-2212.
102) Solymosi, F.; Jáky, K. Stability of Ammonium Halates in the Solid State: Kinetic Study of the Thermal Decomposition of Ammonium lodate. J. Inorg. Nucl. Chem. 1971, 33, 2829-2838.
103) Stauffer, J. E. Process for the Chlorination of Methane. World U.S. Pat. No. 9,008,117A1, Jul. 26, 1990
104) Strassner, T.; Ahrens, S.; Muehlhofer, M.; Munz, D.; Zeller, A., Cobalt-Catalyzed Oxidation of Methane to Methyl Trifluoroacetate by Dioxygen. Eur. J. Inorg. Chem. 2013, 2013 (21), 3659-3663.
105) Sze, M. C.; Riegel, H.; Schindler, H. D. Oxychlorination of methane. U.S. Pat. No. 4,207,268A, Jun. 10, 1980.
106) Tabushi, I.; Hamuro, J.; Oda, R. Free-Radical Substitution on Adamantane. J. Am. Chem. Soc. 1967, 89, 7127-7129.
107) Taylor, C. E.; Noceti, R. P.; Schehl, R. R. Direct Conversion of Methane to Liquid Hydrocarbons through Chlorocarbon Intermediates. Stud. Surf. Sci. Catal. 1988, 36, 483-489.
108) Tedder, J. M. Which Factors Determine the Reactivity and Regioselectivity of Free Radical Substitution and Addition Reactions? Angew. Chem., Int. Ed. 1982, 21, 401-410.
109) The World Bank. Global Gas Flaring Reduction Partnership (GGFR). http://www.worldbank.org/en/programs/gasflaringreduction (accessed Jan. 29, 2017).
110) Tschuikow-Roux, E.; Paddison, S. Bond Dissociation Energies and Radical Heats of Formation in CH3Cl, CH2Cl2, CH3Br, CH2Br2, CH2FCl, and $CHFCl_2$. Int. J. Chem. Kinet. 1987, 19, 15-24.
111) U.S. Energy Information Administration. Independent Statistics & Analysis: Natural Gas. https://www.eia.gov/dnav/ng/hist/rngwhhdm.htm (accessed Jan. 29, 2017).
112) Walling, C.; Mayahi, M. F. Some Solvent and Structural Effects in Free Radical Chlorination. J. Am. Chem. Soc. 1959, 81, 1485-1489.
113) Wang, K. X.; Xu, H. F.; Li, W. S.; Zhou, X. P. Acetic Acid Synthesis from Methane by Non-Synthetic Gas Process. J. Mol. Catal. A: Chem. 2005, 225, 65-69.
114) Wang, Q.; Chen, X.; Jha, A. N.; Rogers, H. Natural Gas from Shale Formation—The Evolution, Evidences and Challenges of Shale Gas Revolution in United States. Renewable Sustainable Energy Rev. 2014, 30, 1-28.
115) Wang, R.; Lin, R.; Ding, Y.; Liu, J. Model Iron Phosphate Catalysts for the Oxy-Bromination of Methane. Catal. Lett. 2014, 144, 1384-1392.
116) Wang, R.; Lin, R.; Ding, Y.; Liu, J.; Wang, J.; Zhang, T. Structure and Phase Analysis of One-Pot Hydrothermally Synthesized FePO4-SBA-15 as an Extremely Stable Catalyst for Harsh Oxy-Bromination of Methane. Appl. Catal., A. 2013, 453, 235-243.
117) Wang, X.; Liu, Y.; Zhang, Y.; Zhang, T.; Chang, H.; Zhang, Y.; Jiang, L., Structural requirements of manganese oxides for methane oxidation: XAS spectroscopy and transition state studies. Appl. Catal. B 2018, 229, 52-62.
118) Webb, J. R.; Bolaño, T.; Gunnoe, T. B. Catalytic Oxy-Functionalization of Methane and Other Hydrocarbons: Fundamental Advancements and New Strategies. ChemSusChem 2011, 4, 37-49.
119) Webster-Gardiner, M. S.; Fu, R.; Fortman, G. C.; Nielsen, R. J.; Gunnoe, T. B.; Goddard, W. A. III. Catal. Sci. Technol. 2015, 5, 96-100; d. Fu, R.; O'Reilly, M. E.; Nielsen, R. J.; Goddard, W. A. III; Gunnoe, T. B. Chem. Eur. J. 2015, 21, 1286-1293
120) Webster-Gardiner, M. S.; Piszel, P. E.; Fu, R.; Chen, J.; Mckeown, B. A.; Nielsen, R. J.; Goddard, W. A. III; Gunnoe, T. B. J. Mol. Catal. A: Chem. 2017, 426B, 381-388.
121) Wittcoff, H. A.; Reuben, B. G.; Plotkin, J. S. Industrial Organic Chemicals. John Wiley & Sons: Hoboken, NJ, 2012, p 459.
122) Zakaria, Z.; Kamarudin, S. K. Direct Conversion Technologies of Methane to Methanol: An Overview. Renewable Sustainable Energy Rev. 2016, 65, 250-261.
123) Zefirov, N. S.; Zhdankin, V. V.; Makhon'kova, G. V.; Dan'kov, Y. V.; Koz'min, A. S. Oxidatively Assisted Nucleophilic Substitution of lodine in Alkyl lodides by Nucleofugic Anions. J. Org. Chem. 1985, 50, 1872-1876.
124) Zhdankin, V. V. Hypervalent lodine (III) Reagents in Organic Synthesis. Arkivoc 2009, 1-62.
125) Zhdankin, V. V.; Stang, P. J. Chemistry of Polyvalent lodine. Chem. Rev. 2008, 108, 5299-5358.
126) Zhou, K.; Wang, W.; Zhao, Z.; Luo, G.; Miller, J. T.; Wong, M. S.; Wei, F., Synergistic gold-bismuth catalysis for non-mercury hydrochlorination of acetylene to vinyl chloride monomer. ACS Catal. 2014, 4 (9), 3112-3116.
127) Zichitella, G.; Paunović, V.; Amrute, A. P.; Pérez-Ramírez, J. Catalytic Oxychlorination versus Oxybromination for Methane Functionalization. ACS Catal. 2017, 7, 1805-1817.

What is claimed is:

1. A method comprising mixing a hydrocarbon with a composition comprising an acid and an oxidant comprising a manganese compound, to produce a functionalized hydrocarbon, wherein the acid is selected from the group consisting of trifluoroacetic acid, triflic acid, trifluoromethyl phosphonic acid, hexafluorobutyric acid, sulfuric acid, acetic acid, methanesulfonic acid, phosphoric acid, and any combination thereof, and the manganese compound is not $Mn_2O_3$, wherein the manganese compound comprises $Mn_2(TFA)_4(HTFA)_4$.

2. The method of claim 1, wherein the composition further comprises iodine, an iodine-based compound, or a combination thereof.

3. The method of claim 2, wherein the iodine-based compound comprises iodate, periodate, iodine oxide, iodosyl ($IO^+$), trivalent iodine compound, or any combination thereof.

4. The method of claim 2, wherein the iodine-based compound is $Q(IO_3)_p$, wherein Q is hydrogen, lithium, sodium, potassium, beryllium, magnesium, calcium, strontium, barium, transition metals, aluminum, gallium, thallium, indium, tin, sulfur, ammonium ($NH_4^+$), alkylammonium, phosphonium ($PH_4^+$), alkylphosphonium, arylphosphonium, or trimethyl sulfonium ($[S(CH_3)_3]^+$), wherein p is from 1 to 5.

5. The method of claim 2, wherein the iodine-based compound is selected from the group consisting of: $KIO_3$, $Ca(IO_3)_2$, $Ba(IO_3)_2$, $Cu(IO_3)_2$, $NH_4IO_3$, $H_5IO_6$, $KIO_4$, $NaIO_4$, $NH_4IO_4$, $I(TFA)_3$, $I_2O_5$, $[IO]^+$, $[IO_2]^+$, and any combination thereof.

6. The method of claim 2, wherein the molar ratio of the oxidant to the iodine or iodine-based compound is from 1:1 to 30:1.

7. The method of claim 1, wherein the acid comprises trifluoroacetic acid.

8. The method of claim 1, wherein the hydrocarbon and composition are heated at a temperature of from about 100° C. to about 300° C.

9. The method of claim 1, wherein the hydrocarbon comprises a linear or branched alkane or a cycloalkane.

10. The method of claim 1, wherein the hydrocarbon comprises methane, ethane, or propane.

11. The method of claim 1, wherein the hydrocarbon is monofunctionalized.

12. A method comprising mixing a hydrocarbon with a composition comprising an acid and an oxidant comprising $Mn_2(TFA)_4(HTFA)_4$ to produce a functionalized hydrocarbon.

13. The method of claim 12, wherein the acid comprises trifluoroacetic acid, triflic acid, trifluoromethyl phosphonic acid, hexafluorobutyric acid, sulfuric acid, acetic acid, methanesulfonic acid, phosphoric acid, or any combination thereof.

14. The method of claim 12, wherein the hydrocarbon comprises a linear or branched alkane or a cycloalkane.

15. The method of claim 12, wherein the hydrocarbon comprises methane, ethane, or propane.

16. The method of claim 12, wherein the composition further comprises iodine, an iodine-based compound, or a combination thereof.

17. The method of claim 16, wherein the iodine-based compound comprises iodate, periodate, iodine oxide, iodosyl ($IO^+$), trivalent iodine compound, or any combination thereof.

18. The method of claim 16, wherein the iodine-based compound is $Q(IO_3)_p$, wherein Q is hydrogen, lithium, sodium, potassium, beryllium, magnesium, calcium, strontium, barium, transition metals, aluminum, gallium, thallium, indium, tin, sulfur, ammonium ($NH_4^+$), alkylammonium, phosphonium ($PH_4^+$), alkylphosphonium, arylphosphonium, or trimethyl sulfonium ($[S(CH_3)_3]^+$), wherein p is from 1 to 5.

19. The method of claim 16, wherein the iodine-based compound is selected from the group consisting of: $KIO_3$, $Ca(IO_3)_2$, $Ba(IO_3)_2$, $Cu(IO_3)_2$, $NH_4IO_3$, $H_5IO_6$, $KIO_4$, $NaIO_4$, $NH_4IO_4$, $I(TFA)_3$, $I_2O_5$, $[IO]^+$, $[IO_2]^+$, and any combination thereof.

20. The method of claim 12, wherein the composition further comprises $A_aX_n$, wherein A is hydrogen, lithium, sodium, potassium, beryllium, magnesium, calcium, strontium, barium, transition metals, aluminum, gallium, thallium, indium, tin, sulfur, ammonium ($NH_4^+$), alkylammonium, phosphonium ($PH_4^+$), alkylphosphonium, arylphosphonium, trimethyl sulfonium ($[S(CH_3)_3]^+$) or a combination thereof, wherein X is chlorine, wherein subscript "a" is an oxidation state of X and subscript "n" is an oxidation state of A.

21. The method of claim 20, wherein AX is HCl, NaCl, KCl, $CaCl_2$), LiCl, $ZnCl_2$, $BeCl_2$, $MgCl_2$, $NH_4Cl$, transition metal chlorides, or any combination thereof.

* * * * *